US011655471B2

(12) United States Patent
Tripp

(10) Patent No.: US 11,655,471 B2
(45) Date of Patent: May 23, 2023

(54) ENGINEERED CELLS WITH DECREASED GENE EXPRESSION RESULTING IN INCREASED VIRAL PRODUCTION

(71) Applicant: UNIVERSITY OF GEORGIA RESEARCH FOUNDATION, INC., Athens, GA (US)

(72) Inventor: Ralph A Tripp, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/490,919

(22) PCT Filed: Mar. 8, 2018

(86) PCT No.: PCT/US2018/021465

§ 371 (c)(1),
(2) Date: Sep. 4, 2019

(87) PCT Pub. No.: WO2018/165373

PCT Pub. Date: Sep. 13, 2018

(65) Prior Publication Data

US 2020/0010830 A1 Jan. 9, 2020

Related U.S. Application Data

(60) Provisional application No. 62/468,430, filed on Mar. 8, 2017.

(51) Int. Cl.
*C12N 5/10* (2006.01)
*C12N 15/113* (2010.01)
*C12N 7/00* (2006.01)

(52) U.S. Cl.
CPC .............. *C12N 15/113* (2013.01); *C12N 7/00* (2013.01); *C12N 5/10* (2013.01); *C12N 2310/14* (2013.01); *C12N 2710/16752* (2013.01); *C12N 2760/16152* (2013.01); *C12N 2760/16252* (2013.01); *C12N 2760/18752* (2013.01); *C12N 2770/24152* (2013.01); *C12N 2770/32052* (2013.01); *C12N 2770/32352* (2013.01); *C12N 2770/32452* (2013.01); *C12N 2770/32652* (2013.01); *C12N 2770/36252* (2013.01)

(58) Field of Classification Search
None
See application file for complete search history.

(56) References Cited

U.S. PATENT DOCUMENTS

2007/0087015 A1 4/2007 Eckels et al.
2010/0233703 A1* 9/2010 He .................. G01N 33/57423 435/6.12
2010/0291624 A1* 11/2010 Zhang .................. C12N 9/2402 435/363
2011/0183014 A1* 7/2011 Huang .................. A61K 36/758 435/375
2015/0374812 A1* 12/2015 Karpilow .................. C12N 7/00 424/217.1
2016/0373636 A1 12/2016 Hamada

FOREIGN PATENT DOCUMENTS

WO WO-2014123967 A2 * 8/2014 .............. A61P 35/00
WO 2017007784 A1 12/2017

OTHER PUBLICATIONS

Partial Supplementary European Search Report issued in EP18763588.3, dated Dec. 1, 2020, 10 pages.
Murray et al., A universal mammalian vaccine cell line substrate,; PLOS One, vol. 12, No. 11, Nov. 27, 2017.
International Search Report and Written Opinion issued for Application No. PCT/US2018/021465, dated Jul. 10, 2018, 11 pages.
Phanthanawiboon, et al. Isolation and Propagation of Dengue Virus In Vero and BHK-21 Cells Expressing Human DC-SIGN Stably. J ViroJ Methods, 2014, vol. 209, pp. 55-61.
Abraham, R., et al., High throughput proteomic analysis and a comparative review identify the nuclear chaperone, Nucleophosmin among the common set of proteins modulated in Chikungunya virus infection. J Proteomics, 2015. 120: p. 126-41.
Agbulos DS, Barelli L, Giordano BV, Hunter FF (2016) Zika Virus: Quantification, Propagation, Detection, and Storage. Curr Protoc Microbiol 43: 15D 14 11-15D 14 16.
Agrawal S, Kandimalla ER (2004) Role of Toll-like receptors in antisense and siRNA [corrected]. Nat Biotechnol 22: 1533-1537.
An, S., et al., Induction of apoptosis in murine coronavirus-infected cultured cells and demonstration of E protein as an apoptosis inducer. J Virol, 1999. 73(9): p. 7853-9.
Andrei, G., et al., Evaluating phenotype and genotype of drug-resistant strains in herpesviruses. Mol Biotechnol, 2001. 18(2): p. 155-67.
Andzhaparidze OG, Bogomolova NN, Boriskin Yu S, Drynov ID (1983) Chronic non-cytopathic infection of human continuous cell lines with mumps virus. Acta Virol 27:318-328.
Arvin, A.M., Varicella-zoster virus. Clin Microbiol Rev, 1996. 9(3): p. 361-81.
Audsley JM, Tannock GA (2005) The growth of attenuated influenza vaccine donor strains in continuous cell lines. J Virol Methods 123: 187-193.
Bagga, S. and M.J. Bouchard, Cell cycle regulation during viral infection. Methods Mol Biol, 2014. 1170: p. 165-227.
Bakre A, Andersen LE, Meliopoulos V, Coleman K, Yan X, et al. (2013) Identification of Host Kinase Genes Required for Influenza Virus Replication and the Regulatory Role of MicroRNAs. PLoS One 8: e66796.

(Continued)

*Primary Examiner* — Nicole Kinsey White
(74) *Attorney, Agent, or Firm* — Meunier Carlin & Curfman LLC

(57) ABSTRACT

Disclosed are compositions and methods for increasing virus production. In particular, disclosed herein are cell or cell line comprises reduced expression of one or more cellular genes selected from the group comprising COQ9, FGF2, NAT9, NDUFA9, NEU2, PLA2G1B, PYCR1, RAD51AP1, STRADA, SVOPL, and/or ZFYVE9 for use in increasing viral production.

5 Claims, 21 Drawing Sheets

(56) References Cited

OTHER PUBLICATIONS

Barrett, P.N., D. Portsmouth, and H.J. Ehrlich, Vero cell culture-derived pandemic influenza vaccines: preclinical and clinical development. Expert Rev Vaccines, 2013. 12(4): p. 395-413.
Barrett, P.N., et al., Vero cell platform in vaccine production: moving towards cell culture-based viral vaccines. Expert Rev Vaccines, 2009. 8(5): p. 607-18.
Calvet, G.A., F.B. Santos, and P.C. Sequeira, Zika virus infection: epidemiology, clinical manifestations and diagnosis. Curr Opin Infect Dis, 2016. 29(5): p. 459-66.
Cassone A, Rappuoli R (2010) Universal vaccines: shifting to one for many. MBio 1.
Cavaletto M, Giuffrida MG, Fortunato D, Gardano L, Dellavalle G, et al. (2002) A proteomic approach to evaluate the butyrophilin gene family expression in human milk fat globule membrane. Proteomics 2: 850-856.
Chavas LM, Tringali C, Fusi P, Venerando B, Tettamanti G, et al. (2005) Crystal structure of the human cytosolic sialidase Neu2. Evidence for the dynamic nature of substrate recognition. J Biol Chem 280: 469-475.
Choumet, V. and P. Despres, Dengue and other flavivirus infections. Rev Sci Tech, 2015. 34(2): p. 473-8.
Clarke, B.D., et al., Functional non-coding RNAs derived from the flavivirus 3' untranslated region. Virus Res, 2015. 206: p. 53-61.
Clementi, N., et al., A human monoclonal antibody with neutralizing activity against highly divergent influenza subtypes. PLoS One, 2011. 6(12): p. e28001.
Cunningham, A.L., The herpes zoster subunit vaccine. Expert Opin Biol Ther, 2016. 16(2): p. 265-71.
De Filette, M., et al., Antiserum against the conserved nine amino acid N-terminal peptide of influenza A virus matrix protein 2 is not immunoprotective. J Gen Virol, 2011. 92(Pt 2): p. 301-6.
Desmyter J, Melnick JL, Rawls WE (1968) Defectiveness of interferon production and of rubella virus interference in a line of African green monkey kidney cells (Vero). J Virol 2: 955-961.
Dormitzer PR, Galli G, Castellino F, Golding H, Khurana S, et al. (2011) Influenza vaccine immunology. Immunol Rev 239: 167-177.
Dyson, H.J. and P.E. Wright, Role of Intrinsic Protein Disorder in the Function and Interactions of the Transcriptional Coactivators CREB-binding Protein (CBP) and p300. J Biol Chem, 2016. 291(13): p. 6714-22.
Engelich, G., M. White, and K.L. Hartshorn, Neutrophil survival is markedly reduced by incubation with influenza virus and *Streptococcus pneumoniae*: role of respiratory burst. J Leukoc Biol, 2001. 69(1): p. 50-6.
Feinstone SM, Daemer RJ, Gust ID, Purcell RH (1983) Live attenuated vaccine for hepatitis A. Dev Biol Stand 54: 429-432.
Feldman, S.A., et al., Use of the piggyBac transposon to create stable packaging cell lines for the production of clinical-grade self-inactivating gamma-retroviral vectors. Hum Gene Ther Methods, 2014. 25(4): p. 253-60.
Fiorucci G., et al., MicroRNAs in virus-induced tumorigenesis and IFN system. Cytokine Growth Factor Rev, 2015. 26(2): p. 183-94.
Fletcher, M.A., L. Hessel, and S.A. Plotkin, Human diploid cell strains (HDCS) viral vaccines. Dev Biol Stand, 1998. 93: p. 97-107.
Genzel, Y., Designing cell lines for viral vaccine production: Where do we stand? Biotechnol J, 2015. 10(5): p. 728-40.
Goebel S, Snyder B, Sellati T, Saeed M, Ptak R, et al. (2016) A sensitive virus yield assay for evaluation of Antivirals against Zika Virus. J Virol Methods 238: 13-20.
Gordy JT, Jones CA, Rue J, Crawford PC, Levy JK, et al. (2012) Surveillance of feral cats for influenza A virus in north central Florida. Influenza Other Respir Viruses 6: 341-347.
Grahn A, Studahi M (2015) Varicella-zoster virus infections of the central nervous system—Prognosis, diagnostics and treatment. J Infect 71: 281-293.
Grimwood K, Lambert SB, Milne RJ (2010) Rotavirus infections and vaccines burden of illness and potential impact of vaccination. Paediatr Drugs 12: 235-256.
Hallauer, P.L. and K.E. Hastings, Human cytomegalovirus IE1 promoter/enhancer drives variable gene expression in all fiber types in transgenic mouse skeletal muscle. BMC Genet, 2000. 1: p. 1.
Holmes K, Williams CM, Chapman EA, Cross MJ (2010) Detection of siRNA induced mRNA silencing by RT-qPCR: considerations for experimental design. BMC Res Notes 3: 53.
Huang YJ, Higgs S, Horne KM, Vanlandingham DL (2014) Flavivirus-mosquito interactions. Viruses 6: 4703-4730.
Hughes JH (1993) Physical and chemical methods for enhancing rapid detection of viruses and other agents. Clin Microbiol Rev 6: 150-175.
Jacobsson JA, Haitina T, Lindblom J, Fredriksson R (2007) Identification of six putative human transporters with structural similarity to the drug transporter SLC22 family. Genomics 90: 595-609.
Jang, Y.H., et al., Host defense mechanism-based rational design of live vaccine. PLoS One, 2013. 8(10): p. e75043.
Jazi, M.H., et al., In vivo electroporation enhances immunogenicity and protection against influenza A virus challenge of an M2e-HSP70c DNA vaccine. Virus Res, 2012. 167(2): p. 219-25.
Jeang, K.T., RNAi in the regulation of mammalian viral infections. BMC Biol, 2012. 10: p. 58.
Kaiser, W.J., J.W. Upton, and E.S. Mocarski, Viral modulation of programmed necrosis. Curr Opin Virol, 2013. 3(3): p. 296-306.
Keating GM (2016) Shingles (*Herpes zoster*) Vaccine (Zostavax((R))): A Review in the Prevention of Herpes Zoster and Postherpetic Neuralgia. BioDrugs 30: 243-254.
Keating, R., et al., The kinase mTOR modulates the antibody response to provide cross-protective immunity to lethal infection with influenza virus. Nat Immunol, 2013. 14(12): p. 1266-76.
Kennedy, P.G., Issues in the Treatment of Neurological Conditions Caused by Reactivation of Varicella Zoster Virus (VZV). Neurotherapeutics, 2016. 13(3): p. 509-13.
Kirkwood CD, Bishop RF, Coulson BS (1998) Attachment and growth of human rotaviruses RV-3 and S12/85 in Caco-2 cells depend on VP4. J Virol 72: 9348-9352.
Kramer, M.J., et al., Cell and virus sensitivity studies with recombinant human alpha interferons. J Interferon Res, 1983. 3(4): p. 425-35.
Kularatne, S.A., Dengue fever. BMJ, 2015. 351: p. h4661.
Kuo ML, Lee MB, Tang M, den Besten W, Hu S, et al. (2016) PYCR1 and PYCR2 Interact and Collaborate with RRM2B to Protect Cells from Overt Oxidative Stress. Sci Rep 6: 18846.
Lambert N, Strebel P, Orenstein W, Icenogle J, Poland GA (2015) Rubella. Lancet 385: 2297-2307.
Lavender, H., et al., In vitro characterization of the activity of PF-05095808, a novel biological agent for hepatitis C virus therapy. Antimicrob Agents Chemother, 2012. 56(3): p. 1364-75.
Lee JH, Lee GC, Kim JI, Yi HA, Lee CH (2013) Development of a new cell culture-based method and optimized protocol for the detection of enteric viruses. J Virol Methods 191: 16-23.
Lessler J, Chaisson LH, Kucirka LM, Bi Q, Grantz K, et al. (2016) Assessing the global threat from Zika virus. Science 353: aaf8160.
Li ML, Weng KF, Shih SR, Brewer G (2016) The evolving world of small RNAs from RNA viruses. Wiley Interdiscip Rev RNA 7: 575-588.
Liebhaber H, Riordan JT, Horstmann DM (1967) Replication of rubella virus in a continuous line of African green monkey kidney cells (Vero). Proc Soc Exp Biol Med 125: 636-643.
Liu, X., et al., [Establishment of a stable and inducible mammalian cell line expressing influenza virus A M2 protein]. Sheng Wu Gong Cheng Xue Bao, 2011. 27(5): p. 747-54. English Abstract.
Lohman DC, Forouhar F, Beebe ET, Stefely MS, Minogue CE, et al. (2014) Mitochondrial COQ9 is a lipid-binding protein that associates with COQ7 to enable coenzyme Q biosynthesis. Proc Natl Acad Sci U S A 111: E4697-4705.
Lyons, S.F., et al., An indirect radioimmunoassay for interferon. J Virol Methods, 1982. 5(2): p. 93-100.
Mackinnon AL, Paavilainen VO, Sharma A, Hegde RS, Taunton J (2014) An allosteric Sec61 inhibitor traps nascent transmembrane helices at the lateral gate. Elife 3: e01483.

(56) References Cited

OTHER PUBLICATIONS

Man, S.M., R. Karki, and T.D. Kanneganti, AIM2 inflammasome in infection, cancer, and autoimmunity: Role in DNA sensing, inflammation, and innate immunity. Eur J Immunol, 2016. 46(2): p. 269-80.
Martin A, Lemon SM (2006) Hepatitis A virus: from discovery to vaccines. Hepatology 43: S164-172.
Meliopoulos VA, Andersen LE, Birrer KF, Simpson KJ, Lowenthal JW, et al. (2012) Host gene targets for novel influenza therapies elucidated by high-throughput RNA interference screens. FASEB J 26: 1372-1386.
Meliopoulos VA, Andersen LE, Brooks P, Yan X, Bakre A, et al. (2012) MicroRNA regulation of human protease genes essential for influenza virus replication. PLoS One 7: e37169.
Milstien J, Grachev V, Padilla A, Griffiths E (1996) WHO activities towards the three Rs in the development and control of biological products. Dev Biol Stand 86: 31-39.
Modlin J, Wenger J (2014) Achieving and maintaining polio eradication—new strategies. N Engl J Med 371: 1476-1479.
Montagnon, B.J. and J.C. Vincent-Falquet, Experience with the Vero cell line. Dev Biol Stand, 1998. 93: p. 119-23.
Moore AE, Sabachewsky L, Toolan HW (1955) Culture characteristics of four permanent lines of human cancer cells. Cancer Res 15: 598-602.
Music S (2010) Governments, off-patent vaccines, smallpox and universal childhood vaccination. Vaccine 28: 869-872.
Nagarajan MM, Kibenge FS (1998) A novel technique for in-vivo assay of viral regulatory regions in genomes of animal RNA viruses. J Virol Methods 72: 51-58.
Nagy, P.D. and J. Pogany, The dependence of viral RNA replication on co-opted host factors. Nat Rev Microbiol, 2011. 10(2): p. 137-49.
Nakai, Y., et al., Apoptosis and microglial activation in influenza encephalopathy. Acta Neuropathol, 2003. 105(3): p. 233-9.
Ojha CR, Rodriguez M, Dever SM, Mukhopadhyay R, El-Hage N (2016) Mammalian microRNA: an important modulator of host-pathogen interactions in human viral infections. J Biomed Sci 23: 74.
Park, M.S., et al., Newcastle disease virus V protein is a determinant of host range restriction. J Virol, 2003. 77(17): p. 9522-32.
Pizzuto, M.S., et al., An engineered avian-origin influenza A virus for pancreatic ductal adenocarcinoma virotherapy. J Gen Virol, 2016. 97(9): p. 2166-79.
Poltronieri P, Sun B, Mallardo M (2015) RNA Viruses: RNA Roles in Pathogenesis, Coreplication and Viral Load. Curr Genomics 16: 327-335.
Rao CD, Reddy H, Naidu JR, Raghavendra A, Radhika NS, et al. (2015) An enzyme-linked immuno focus assay for rapid detection and enumeration, and a newborn mouse model for human non-polio enteroviruses associated with acute diarrhea. J Virol Methods 224: 47-52.
Reemers, S.S., et al., Cellular host transcriptional responses to influenza A virus in chicken tracheal organ cultures differ from responses in in vivo infected trachea. Vet Immunol Immunopathol, 2009. 132(2-4): p. 91-100.
Saito, T. and M. Gale, Jr., Principles of intracellular viral recognition. Curr Opin Immunol, 2007. 19(1): p. 17-23.
Santak M, Markusic M, Balija ML, Kopac SK, Jug R, et al. (2015) Accumulation of defective interfering viral particles in only a few passages in Vero cells attenuates mumps virus neurovirulence. Microbes Infect 17: 228-236.
Scott LJ (2016) Tetravalent Dengue Vaccine: A Review in the Prevention of Dengue Disease. Drugs 76: 1301-1312.
Shaw, M.L., et al., Nipah virus V and W proteins have a common STAT1-binding domain yet inhibit STAT1 activation from the cytoplasmic and nuclear compartments, respectively. J Virol, 2004. 78(11): p. 5633-41.
Sim, S. and M.L. Hibberd, Genomic approaches for understanding dengue: insights from the virus, vector, and host. Genome Biol, 2016. 17: p. 38.
Sloop, K.W., M.D. Michael, and J.S. Moyers, Glucagon as a target for the treatment of Type 2 diabetes. Expert Opin Ther Targets, 2005. 9(3): p. 593-600.
Smith DR (2016) Waiting in the wings: The potential of mosquito transmitted flaviviruses to emerge. Crit Rev Microbiol: 1-18.
Stroud DA, Formosa LE, Wijeyeratne XW, Nguyen TN, Ryan MT (2013) Gene knockout using transcription activator-like effector nucleases (TALENs) reveals that human NDUFA9 protein is essential for stabilizing the junction between membrane and matrix arms of complex I. J Biol Chem 288: 1685-1690.
Suzuki R, de Borba L, Duarte dos Santos CN, Mason PW (2007) Construction of an infectious cDNA clone for a Brazilian prototype strain of dengue virus type 1: characterization of a temperature-sensitive mutation in NS1. Virology 362: 374-383.
Takizawa, T., et al., Recruitment of apoptotic cysteine proteases (caspases) in influenza virus-induced cell death. Microbiol Immunol, 1999. 43(3): p. 245-52.
Trigg, B.J. and B.J. Ferguson, Functions of DNA damage machinery in the innate immune response to DNA virus infection. Curr Opin Virol, 2015. 15: p. 56-62.
Tripp RA, Mark Tompkins S (2015) Antiviral effects of inhibiting host gene expression. Curr Top Microbiol Immunol 386: 459-477.
Tripp RA, Tompkins SM (2009) Therapeutic applications of RNAi for silencing virus replication. Methods Mol Biol 555: 43-61.
Van der Sanden SM, Wu W, Dybdahl-Sissoko N, Weldon WC, Brooks P, et al. (2015) Engineering Enhanced Vaccine Cell Lines to Eradicate Vaccine-Preventable Diseases: the Polio End Game. J Virol 90: 1694-1704.
Vincent-Falquet JC, Peyron L, Souvras M, Moulin JC, Tektoff J, et al. (1989) Qualification of working cell banks for the Vero cell line to produce licensed human vaccines. Dev Biol Stand 70: 153-156.
Virk RK, Gunalan V, Tambyah PA (2016) Influenza infection in human host: challenges in making a better influenza vaccine. Expert Rev Anti Infect Ther 14: 365-375.
Wang L, Zhu L, Zhu H (2016) Efficacy of varicella (VZV) vaccination: an update for the clinician. Ther Adv Vaccines 4: 20-31.
Wearing HJ, Robert MA, Christofferson RC (2016) Dengue and chikungunya: modelling the expansion of mosquito-borne viruses into naive populations. Parasitology, 143, 860-873.
Weir JP, Gruber MF (2016) An overview of the regulation of influenza vaccines in the United States. Influenza Other Respir Viruses 10: 354-360.
Westenfeld FW, Winn WC, Jr. (1994) Use of rhesus monkey kidney cells for isolation of varicella-zoster virus. Am J Clin Pathol 102: 733-735.
Worschech, A., et al., Systemic treatment of xenografts with vaccinia virus GLV-1h68 reveals the immunologic facet of oncolytic therapy. BMC Genomics, 2009. 10: p. 301.
Wu W, Orr-Burks N, Karpilow J, Tripp RA (2017) Development of improved vaccine cell lines against rotavirus. Sci Data 4: 170021.
Zamarin, D., et al., Influenza virus PB1-F2 protein induces cell death through mitochondrial ANT3 and VDAC1. PLoS Pathog, 2005. 1(1): p. e4.
Zhou H, Huang Y, Yuan S, Li Y, Wu S, et al. (2017) Sequential immunization with consensus influenza hemagglutinins raises cross-reactive neutralizing antibodies against various heterologous HA strains. Vaccine 35: 305-312.
Zhou Y, Li JX, Jin PF, Wang YX, Zhu FC (2016) Enterovirus 71: a whole virion inactivated enterovirus 71 vaccine. Expert Rev Vaccines 15: 803-813.
International Preliminary Report on Patentability issued for Application No. PCT/US2018/021465, dated Sep. 19, 2019.
Extended European Search Report issued in corresponding application No. 18763588.3, dated Mar. 5, 2021, 10 pages.

* cited by examiner

Coxsackie Virus KO cell lines Plaque assay

Fold change over the Vero P (x-axis): 0 to 35

KO cell lines: Vero P, Vero E6, CNTD2, EP300, ZNF205, Neg cont

ENGINEERED CELLS WITH DECREASED GENE EXPRESSION RESULTING IN INCREASED VIRAL PRODUCTION

This application is a national stage application filed under 35 U.S.C. § 371 of International Application No. PCT/US2018/021465, filed on Mar. 8, 2018, which claims the benefit of U.S. Provisional Application No. 62/468,430, filed on Mar. 8, 2017, applications which are incorporated herein by reference in their entirety.

I. BACKGROUND

Vaccines are one of the most important defenses in the fight against infectious disease. The greater numbers of these vaccines are produced in cell culture. To achieve this, well characterized cell lines (e.g., Vero Cells) are (for example) grown in defined media formulations and then infected with live or live-attenuated viruses. Subsequently, the supernatant containing progeny of the original viral particles is collected and processed to create highly immunogenic doses of vaccine that can then be distributed amongst the population.

Currently, a complex set of factors (population dynamics, bioproduction, costs, etc.) limit the ability to provide adequate immunization coverage worldwide. In particular, bioproduction of vaccines can be expensive and the time required to provide needed quantities of a vaccine can significantly impact the medical benefit to society. Thus, a new technologies are needed that increase vaccine production at greatly reduced costs.

II. SUMMARY

In one aspect, disclosed herein are methods of increasing viral production comprising infecting a cell or cell line with a virus; wherein the cell or cell line comprises reduced expression of one or more cellular genes selected from the group comprising BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205.

Also disclosed are methods of increasing viral production comprising infecting a cell or cell line with a virus; incubating the cell or cell line under conditions suitable for production of the virus by the cell, cells, or cell line; wherein the medium comprises an RNA polynucleotide or small molecule that inhibits the expression of one or more cellular genes selected from the group comprising BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205.

In one aspect, disclosed herein are cells or cell lines comprising decreased expression of one or more of the genes comprising BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 10A:
Figure 10B:
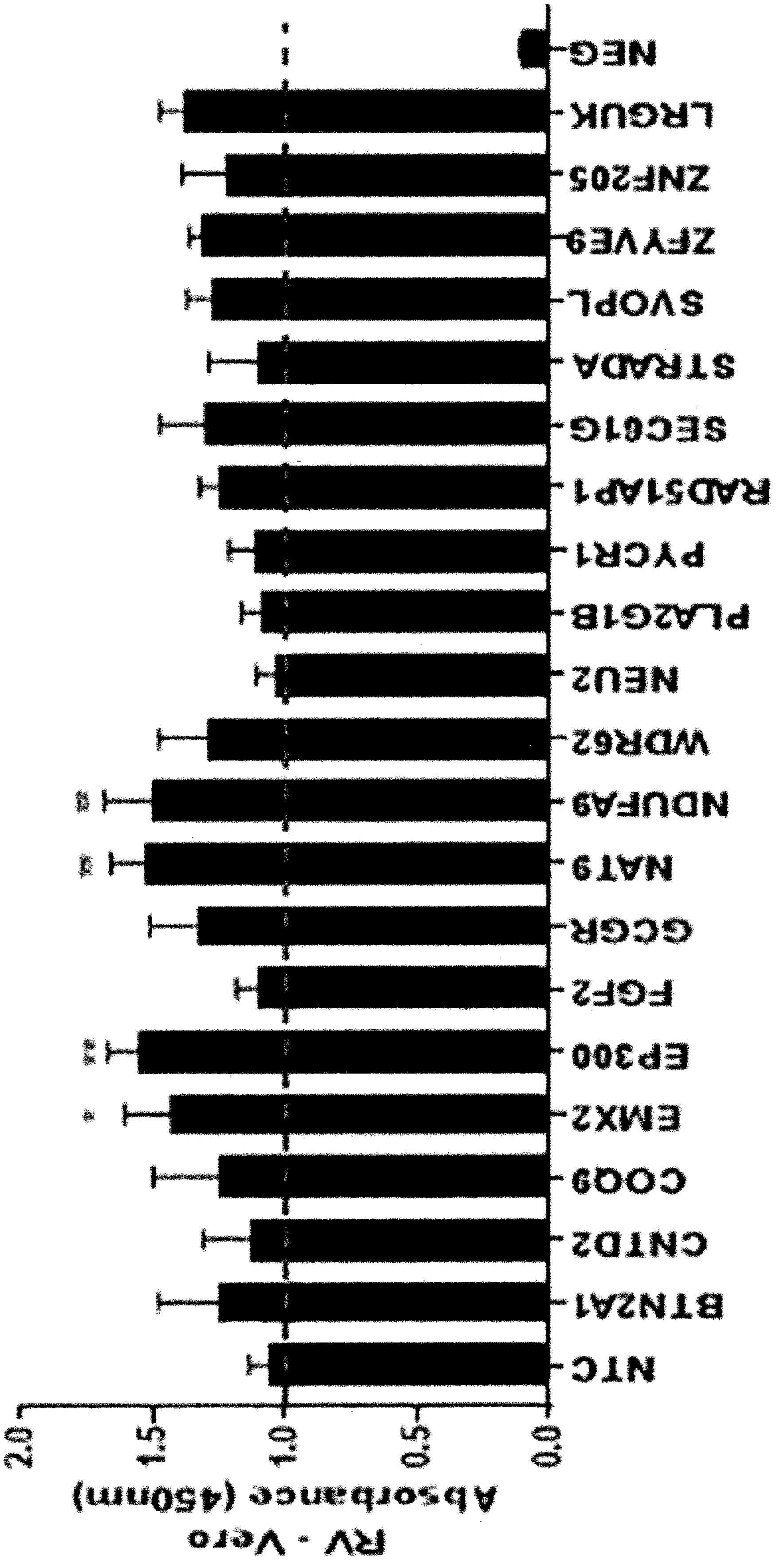
Figure 10C:
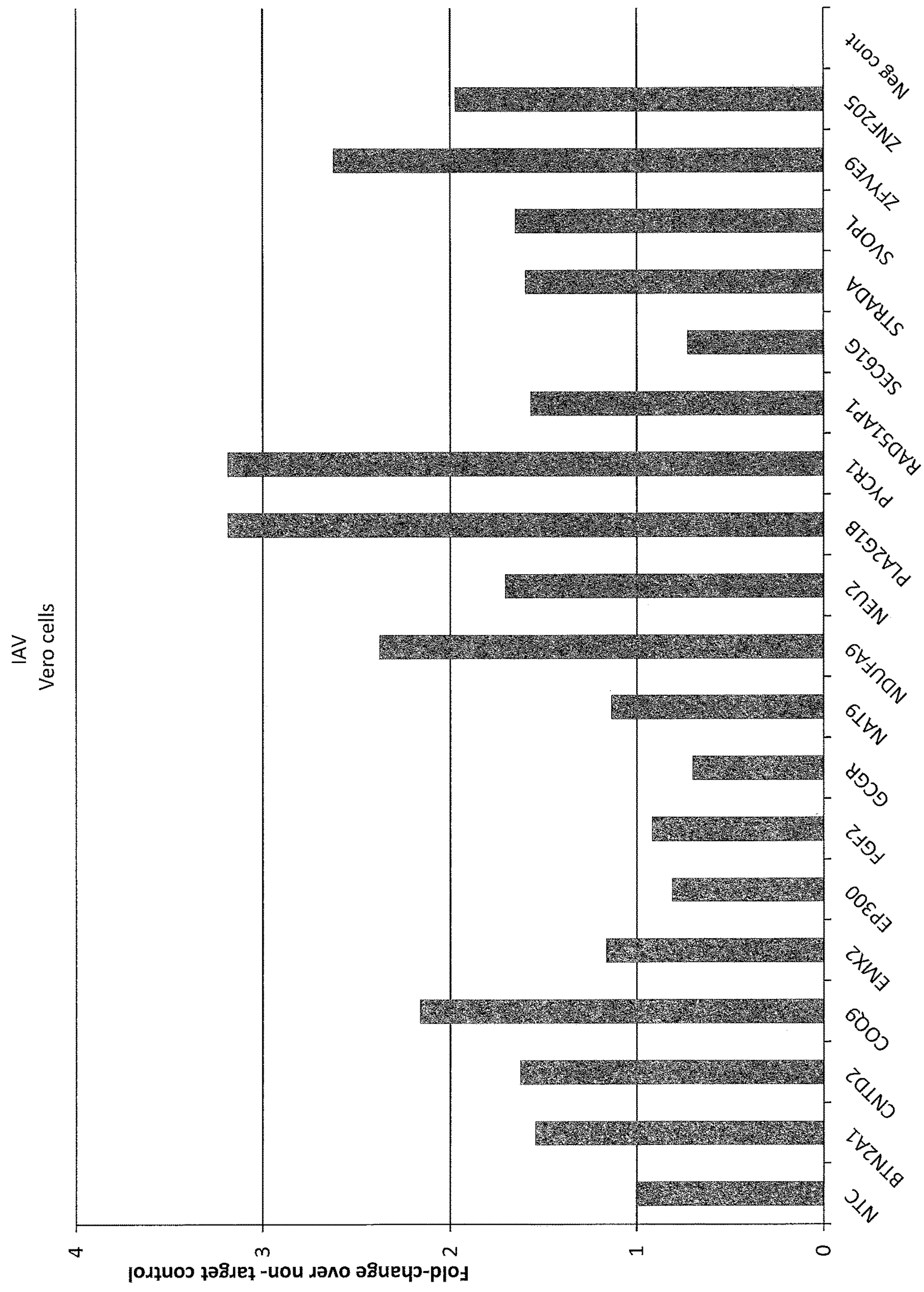

FIGS. 10A, 10B, and 10C show Genome-wide siRNA screening identifies 18 genes that modulate replication of poliovirus (PV), rotavirus (RV) or influenza A virus (JAY). Vero cells were reverse transfected with non-targeting control (NTC)/gene specific on-target plus (OTP) siRNAs (50 nM) for 48 h followed by infection with PV (10A), RV (10B) or IAV (10C). Effect of gene knockdown on viral replication is shown as fold-change relative to NTC from pooled samples. Data represent plaque numbers (10A and 10C) and absorbance (λ=450 nm) for (10B). Error bars represent ±SEM from three independent experiments. * $p<0.05$  $p<0.01$ * $p<0.001$ **** $p<0.0001$.

Figure 11:
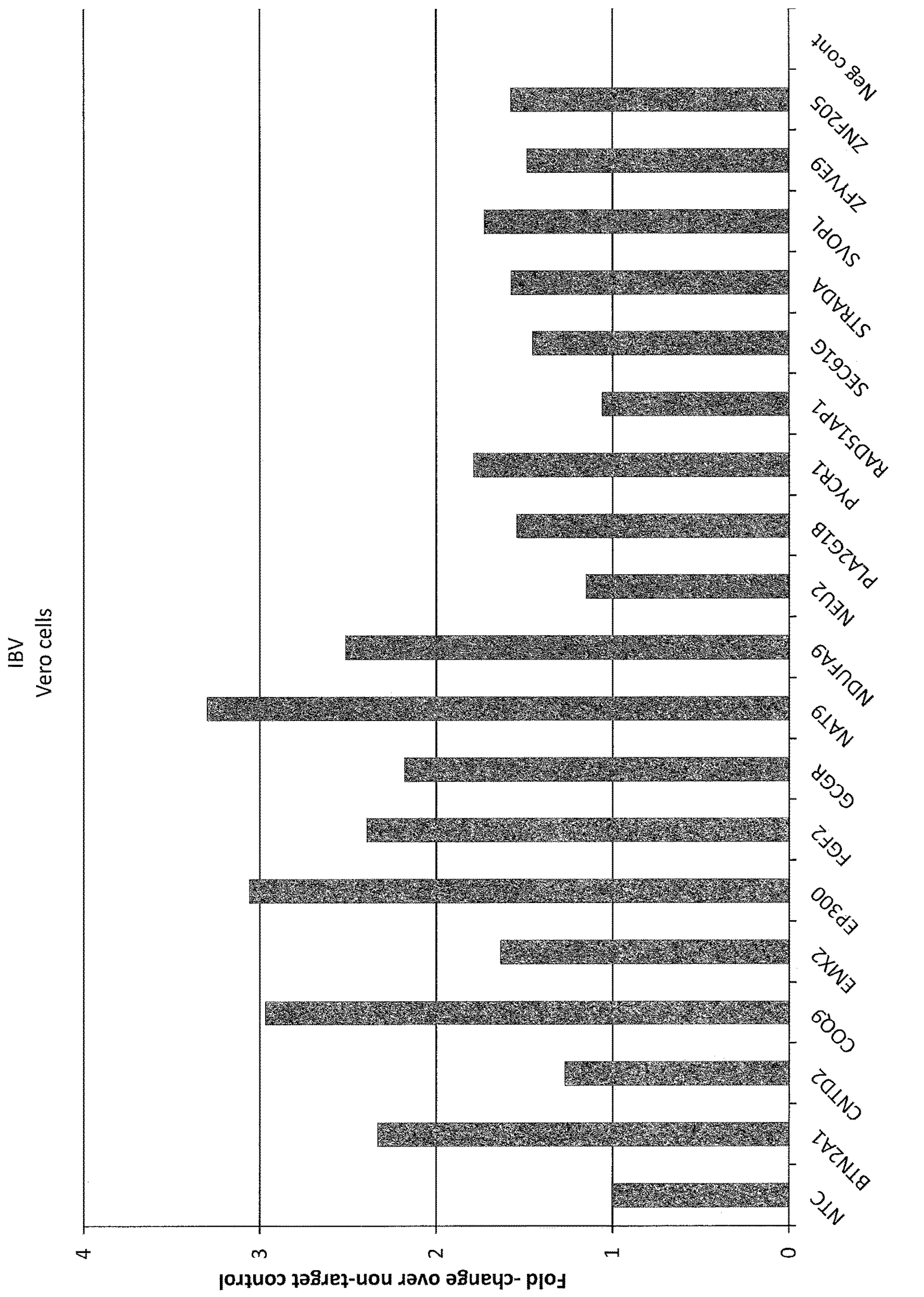

FIG. 11 shows siRNA identifies genes that modulate replication of influenza B virus (IBV). Vero cells were reverse transfected with non-targeting control (NTC)/gene specific on-target plus (OTP) siRNAs (50 nM) for 48 h followed by infection with IBV

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

In the context of this document, the term "target" or "target gene" or "hit" refers to any gene, including protein-encoding genes and non-coding RNAs (e.g., a miRNA) that (when modulated) positively or negatively alters some aspect of virus or biomolecule production. Target genes include endogenous host genes, pathogen (e.g., viral) genes, and transgenes.

The term "modulates" or "modulation" refers to the alteration of the regulation, expression or activity of a gene. In general, it is understood by those in the field that the term "modulation" includes increasing the expression or activity of a gene, decreasing the expression or activity of a gene, as well as altering the specificity or function of a gene. Modulating the expression or activity of a gene can be achieved by a number of means including altering one or more of the following: 1) gene copy number, 2) transcription or translation of a gene, 3) the transcript stability or longevity, 4) the number of copies of an mRNA or miRNA, 5) the availability of a non-coding RNA or non-coding RNA target site, 6) the position or degree of post-translational modifications on a protein, 7) the activity of a protein, and other mechanisms. Modulation can result in a significant reduction in target gene activity (e.g., at least 5%, at least 10%, at least 20% or greater reduction) or an increase in target gene activity (e.g., at least 10%, at least 20%, or greater increase). Furthermore, it is understood by those in the field that modulation of one or more genes can subsequently lead to the modulation of multiple genes (e.g., miRNAs).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods of Increasing Virus Production

Viral vaccines are used to protect human health and ensure food security. Unfortunately, current manufacturing capabilities are limited and costly, thereby placing significant portions of the human and agricultural animal populations at risk. To address this problem, what are needed are methods of increasing viral titers to enhance viral vaccine production. Accordingly, in one aspect, disclosed herein are methods of increasing viral production of one or more viruses and/or virus strains.

In the context of this document the term "vaccine" refers to an agent, including but not limited to a peptide or modified peptide, a protein or modified protein, a live virus, a live attenuated virus, an inactivated or killed virus, a virus-like particle (VLP), or any combination thereof, that is used to stimulate the immune system of an animal or human in order to provide protection against e.g., an infectious agent. Vaccines frequently act by stimulating the production of an antibody, an antibody-like molecule, or a cellular immune response in the subject(s) that receive such treatments.

The term "virus production" can refer to production of a live virus, or an attenuated virus, and/or a VLP. Production can occur by a multitude of methods including 1) production in an organism (e.g., an egg), a cultured cell (e.g., Vero cells), or in vitro (e.g., via a cell lysate).

Vaccines can be generated by a variety of means. In one instance, cells from any number of sources including but not limited to human, non-human primate, canine, and avian are first cultured in an appropriate environment (e.g., a cell or tissue culture plate or flask) to a desired density. Subsequently, viral seed stocks (e.g., Flavivirus (e.g., Dengue, Yellow Fever, or West Nile), Togavirus (e.g., Rubella), Picornavirus (e.g., Coxsackievirus), Paramyxovirus (e.g., Mumps) and/or Herpesvirus (e.g., Varicella Zoster virus)) are added to the culture where they infect cells. Infected cells are then transferred to a bioreactor (e.g., a single use bioreactor) where the virus replicates and expands in number. After a suitable period of time, the cells and cell particulate are separated from newly released viral particles and additional steps (e.g., purification, deactivation, concentration) are performed to further prepare the material for use as a vaccine.

With regard to the growth of the virus, the host cell makes a critical contribution to viral replication, contributing functions related to viral entry, and genome replication, and more.

Accordingly, and in one aspect, disclosed herein are methods of increasing virus production disclosed herein comprise infecting a cell with a virus; wherein the infected cell comprises reduced expression of at least one or more genes from Table 1 whose expression represses viral production. In other words, disclosed herein are methods of increasing virus production comprise infecting a cell with a virus; wherein the infected cell comprises genes that when modulated (individually or in combinations) enhance the production of virus or viral antigen in a cell or cell line (Table I). For example, disclosed herein, expression of butyrophilin subfamily 2 member A1 (BTN2A1), cyclin N-terminal domain containing 2 (CNTD2), coenzyme Q9 (COQ9), empty spiracles homeobox 2 (EMX2), E1A binding protein p300 (EP300), fibroblast growth factor 2 (FGF2), fibroblast growth factor receptor (FGFR), glucagon receptor (GCGR), N-acetyltransferase 9 (NAT9), NADH:ubiquinone oxidoreductase subunit A9 (NDUFA9), neuraminidase 2 (NEU2), phospholipase A2 group IB (PLA2G1B), pyrroline-5-carboxylate reductase 1 (PYCR1), RAD51 associated protein 1 (RAD51AP1), Sec61 translocon gamma subunit (SEC61G), STE20-related kinase adaptor alpha (STRADA) also known as lysin motif receptor kinase 5 (LYKS), SV2 related protein like (SVOPL), zinc finger, FYVE domain containing 9 (ZFYVE9), and/or zinc finger protein 205 (ZNF205) negatively impact viral production. Accordingly, disclosed herein are methods of increasing virus production disclosed herein comprise infecting a cell with a virus (e.g., Flavivirus (e.g., Dengue, Yellow Fever, West Nile, or Zika), Togavirus (e.g., Rubella), Reovirus (e.g., Rotavirus), Picornavirus (e.g., Coxsackievirus, Enterovirus, Poliovirus, or Hepatitis A virus), Paramyxovirus (e.g., Mumps), Orthomyxovirus (e.g., Influenza A or Influenza B), and/or Herpesvirus (e.g., Varicella Zoster virus)); wherein the infected cell comprises reduced expression of at least one gene selected from BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 genes.

It is understood and herein contemplated that the disclosed methods can increase production for a double stranded DNA virus, double stranded RNA virus, a positive sense single stranded RNA virus, or a negative sense single stranded RNA virus. For example, in one aspect, disclosed herein are methods of increasing virus production, wherein the virus is a double stranded DNA virus such as a virus from the viral family Herpesviridae including, but not limited to varicella-zoster virus. In one aspect, disclosed herein are methods of increasing virus production, wherein the virus is a double stranded RNA virus such as a virus from the viral family Reoviridae, such as, for example rotavirus. Also disclosed are methods of increasing virus production, wherein the virus is a positive sense single stranded RNA virus such as a virus from the viral family Picornaviridae, Flaviviridae, or Togaviridae. In one aspect, the positive sense single stranded RNA virus can be a Flavivirus including but not limited to Dengue virus, Yellow fever virus, West Nile virus, Zika virus (including strains PRVABC59 and IbH30656), or St. Louis encephalitis virus or a Togavirus, such as, Rubella. In one aspect, the positive sense single stranded RNA virus can be from the viral family picornaviridae, and the virus is selected from the group comprising Hepatitis A virus, poliovirus, or Coxsackievirus. Also disclosed are methods wherein the virus is a negative sense single stranded RNA virus, wherein the negative sense single stranded RNA virus is from the viral family orthomyxoviridae or paramyxoviridae, such as, for example, Influenza A virus, Influenza B virus or Mumps virus.

As disclosed herein, the disclosed methods can comprise the reduced expression of any combination of one, two, three, four, five, six, seven, eight, nine, 10, 11, 12, 13, 14, 15, 16, 17, or all 18 of the disclosed genes (i.e., BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 genes). For example, the cell can comprise reduced expression of GCGR alone or in combination with any one, two, three, four, five, six, seven, eight, nine, 10, 11, 12, 13, 14, 15, 16, or 17 other of the selected genes. Thus, for example, in one aspect, disclosed herein are method of increasing virus production comprising infecting a cell with virus; wherein the cell comprises reduced expression of BTN2A1; CNTD2; COQ9; EMX2; EP300; FGF2, GCGR; NAT9; NDUFA9; NEU2; PLA2G1B; PYCR1; RAD51AP1; SEC61G; STRADA; SVOPL; ZFYVE9; ZNF205; GCGR and BTN2A1; GCGR and CNTD2; GCGR and COQ9; GCGR and EMX2; GCGR and EP300; GCGR and FGF2; GCGR and NAT9; GCGR and NDUFA9; GCGR and NEU2; GCGR and PLA2G1B; GCGR and PYCR1; GCGR and RAD51AP1; GCGR and SEC61G; GCGR and STRADA; GCGR and SVOPL; GCGR and ZFYVE9; GCGR and ZNF205; GCGR, BTNA21, and CNTD2; GCGR, BTNA21, and COQ9; GCGR, BTNA21, and EMX2; GCGR, BTNA21, and EP300; GCGR, BTNA21, and FGF2; GCGR, BTNA21, and NAT9; GCGR, BTNA21, and NDUFA9; GCGR, BTNA21, and NEU2; GCGR, BTNA21, and PLA2G1B; GCGR, BTNA21, and PYCR1; GCGR, BTNA21, and RAD51AP1; GCGR, BTNA21, and SEC61G; GCGR, BTNA21, and STRADA; GCGR, BTNA21, and SVOPL; GCGR, BTNA21, and ZFYVE9; GCGR, BTNA21, and ZNF205; GCGR, CNTD2, and COQ9; GCGR, CNTD2, and EMX2; GCGR, CNTD2, and EP300; GCGR, CNTD2, and FGF2; GCGR, CNTD2, and NAT9; GCGR, CNTD2, and NDUFA9; GCGR, CNTD2, and NEU2; GCGR, CNTD2, and PLA2G1B; GCGR, CNTD2, and PYCR1; GCGR, CNTD2, and RAD51AP1; GCGR, CNTD2, and SEC61G; GCGR, CNTD2, and STRADA; GCGR, CNTD2, and SVOPL; GCGR, CNTD2, and ZFYVE9; GCGR, CNTD2, and ZNF205; GCGR, COQ9, and EMX2; GCGR, COQ9, and EP300; GCGR, COQ9, and FGF2; GCGR, COQ9, and NAT9; GCGR, COQ9, and NDUFA9; GCGR, COQ9, and NEU2; GCGR, COQ9, and PLA2G1B; GCGR, COQ9, and PYCR1; GCGR, COQ9, and RAD51AP1; GCGR, COQ9, and SEC61G; GCGR, COQ9, and STRADA; GCGR, COQ9, and SVOPL; GCGR, COQ9, and ZFYVE9; GCGR, COQ9, and ZNF205; GCGR, EMX2, and EP300; GCGR, EMX2, and FGF2; GCGR, EMX2, and NAT9; GCGR, EMX2, and NDUFA9; GCGR, EMX2, and NEU2; GCGR, EMX2, and PLA2G1B; GCGR, EMX2, and PYCR1; GCGR, EMX2, and RAD51AP1; GCGR, EMX2, and SEC61G; GCGR, EMX2, and STRADA; GCGR, EMX2, and SVOPL; GCGR, EMX2, and ZFYVE9; GCGR, EMX2, and ZNF205; GCGR, EP300, and FGF2; GCGR, EP300, and NAT9; GCGR, EP300, and NDUFA9; GCGR, EP300, and NEU2; GCGR, EP300, and PLA2G1B; GCGR, EP300, and PYCR1; GCGR, EP300, and RAD51AP1; GCGR, EP300, and SEC61G; GCGR, EP300, and STRADA; GCGR, EP300, and SVOPL; GCGR, EP300, and ZFYVE9; GCGR, EP300, and ZNF205; GCGR, FGF2, and NAT9; GCGR, FGF2, and NDUFA9; GCGR, FGF2, and NEU2; GCGR, FGF2, and PLA2G1B; GCGR, FGF2, and PYCR1; GCGR, FGF2, and RAD51AP1; GCGR, FGF2, and SEC61G; GCGR, FGF2, and STRADA; GCGR, FGF2, and SVOPL; GCGR, FGF2, and ZFYVE9; GCGR, FGF2, and ZNF205; GCGR, NAT9, and NDUFA9; GCGR, NAT9, and NEU2; GCGR, NAT9, and PLA2G1B; GCGR, NAT9, and PYCR1; GCGR, NAT9, and RAD51AP1; GCGR, NAT9, and SEC61G; GCGR, NAT9, and STRADA; GCGR, NAT9, and SVOPL; GCGR, NAT9, and ZFYVE9; GCGR, NAT9, and ZNF205; GCGR, NDUFA9, and NEU2; GCGR, NDUFA9, and PLA2G1B; GCGR, NDUFA9, and PYCR1; GCGR, NDUFA9, and RAD51AP1; GCGR, NDUFA9, and SEC61G; GCGR, NDUFA9, and STRADA; GCGR, NDUFA9, and SVOPL; GCGR, NDUFA9, and ZFYVE9; GCGR, NDUFA9, and ZNF205; GCGR, NEU2, and PLA2G1B; GCGR, NEU2, and PYCR1; GCGR, NEU2, and RAD51AP1; GCGR, NEU2, and SEC61G; GCGR, NEU2, and STRADA; GCGR, NEU2, and SVOPL; GCGR, NEU2, and ZFYVE9; GCGR, NEU2, and ZNF205; GCGR, PLA2G1B, and PYCR1; GCGR, PLA2G1B, and RAD51AP1; GCGR, PLA2G1B, and SEC61G; GCGR, PLA2G1B, and STRADA; GCGR, PLA2G1B, and SVOPL; GCGR, PLA2G1B, and ZFYVE9; GCGR, PLA2G1B, and ZNF205; GCGR, PYCR1, and RAD51AP1; GCGR, PYCR1, and SEC61G; GCGR, PYCR1, and STRADA; GCGR, PYCR1, and SVOPL; GCGR, PYCR1, and ZFYVE9; GCGR, PYCR1, and ZNF205; GCGR, RAD51AP1, and SEC61G; GCGR, RAD51AP1, and STRADA; GCGR, RAD51AP1, and SVOPL; GCGR, RAD51AP1, and ZFYVE9; GCGR, RAD51AP1, and ZNF205; GCGR, SEC61G, and STRADA; GCGR, SEC61G, and SVOPL; GCGR, SEC61G, and ZFYVE9; GCGR, SEC61G, and ZNF205; GCGR, STRADA, and SVOPL; GCGR, STRADA, and ZFYVE9; GCGR, STRADA, and ZNF205; GCGR, SVOPL, and ZFYVE9; GCGR, SVOPL, and ZNF205; GCGR, ZFYVE9, and ZNF205; GCGR, BTN2A1, CNTD2, and COQ9; GCGR, BTN2A1, CNTD2, and EMX2; GCGR, BTN2A1, CNTD2, and EP300; GCGR, BTN2A1, CNTD2, and FGF2; GCGR, BTN2A1, CNTD2, and NAT9; GCGR, BTN2A1, CNTD2, and NDUFA9; GCGR, BTN2A1, CNTD2, and NEU2; GCGR, BTN2A1, CNTD2, and PLA2G1B; GCGR, BTN2A1, CNTD2, and PYCR1; GCGR, BTN2A1, CNTD2, and RAD51AP1; GCGR, BTN2A1, CNTD2, and SEC61G; GCGR, BTN2A1, CNTD2, and STRADA; GCGR, BTN2A1, CNTD2, and SVOPL; GCGR, BTN2A1, CNTD2, and ZFYVE9; GCGR, BTN2A1, CNTD2, and ZNF205; GCGR, BTN2A1, COQ9, and EMX2; GCGR, BTN2A1, COQ9, and EP300; GCGR, BTN2A1, COQ9, and FGF2; GCGR, BTN2A1, COQ9, and NAT9; GCGR, BTN2A1, COQ9, and NDUFA9; GCGR, BTN2A1, COQ9, and NEU2; GCGR, BTN2A1, COQ9, and PLA2G1B; GCGR, BTN2A1, COQ9, and PYCR1; GCGR, BTN2A1, COQ9, and RAD51AP1; GCGR, BTN2A1, COQ9, and SEC61G; GCGR, BTN2A1, COQ9, and STRADA; GCGR, BTN2A1, COQ9, and SVOPL; GCGR, BTN2A1, COQ9, and ZFYVE9; GCGR, BTN2A1, COQ9, and ZNF205; GCGR, BTN2A1, EMX2, and EP300; GCGR, BTN2A1, EMX2, and FGF2; GCGR, BTN2A1, EMX2, and NAT9; GCGR, BTN2A1, EMX2, and NDUFA9; GCGR, BTN2A1, EMX2, and NEU2; GCGR, BTN2A1, EMX2, and PLA2G1B; GCGR, BTN2A1, EMX2, and PYCR1; GCGR, BTN2A1, EMX2, and RAD51AP1; GCGR, BTN2A1, EMX2, and SEC61G; GCGR, BTN2A1, EMX2, and STRADA; GCGR, BTN2A1, EMX2, and SVOPL; GCGR, BTN2A1, EMX2, and ZFYVE9; GCGR, BTN2A1, EMX2, and ZNF205; GCGR, BTN2A1, EP300, and FGF2; GCGR, BTN2A1, EP300, and NAT9; GCGR, BTN2A1, EP300, and NDUFA9; GCGR, BTN2A1, EP300, and NEU2; GCGR, BTN2A1, EP300, and PLA2G1B; GCGR, BTN2A1, EP300, and PYCR1; GCGR, BTN2A1, EP300, and RAD51AP1; GCGR, BTN2A1, EP300, and SEC61G; GCGR, BTN2A1, EP300, and STRADA; GCGR, BTN2A1, EP300, and SVOPL; GCGR, BTN2A1, EP300, and ZFYVE9; GCGR, BTN2A1, EP300, and ZNF205; GCGR, BTN2A1, FGF2, and NAT9; GCGR, BTN2A1, FGF2, and NDUFA9; GCGR, BTN2A1, FGF2, and NEU2; GCGR, BTN2A1, FGF2, and PLA2G1B; GCGR, BTN2A1, FGF2, and PYCR1; GCGR, BTN2A1, FGF2, and RAD51AP1; GCGR, BTN2A1, FGF2, and SEC61G; GCGR, BTN2A1, FGF2, and STRADA; GCGR, BTN2A1, FGF2, and SVOPL; GCGR, BTN2A1, FGF2, and ZFYVE9; GCGR, BTN2A1, FGF2, and ZNF205; GCGR, BTN2A1, NAT9, and NDUFA9; GCGR, BTN2A1, NAT9, and NEU2; GCGR, BTN2A1, NAT9, and PLA2G1B; GCGR, BTN2A1, NAT9, and PYCR1; GCGR, BTN2A1, NAT9, and RAD51AP1; GCGR, BTN2A1, NAT9, and SEC61G; GCGR, BTN2A1, NAT9, and STRADA; GCGR, BTN2A1, NAT9, and SVOPL; GCGR, BTN2A1, NAT9, and ZFYVE9; GCGR, BTN2A1, NAT9, and ZNF205; GCGR, BTN2A1, NDUFA9, and NEU2; GCGR, BTN2A1, NDUFA9, and PLA2G1B; GCGR, BTN2A1, NDUFA9, and PYCR1; GCGR, BTN2A1, NDUFA9, and RAD51AP1; GCGR, BTN2A1, NDUFA9, and SEC61G; GCGR, BTN2A1, NDUFA9, and STRADA; GCGR, BTN2A1, NDUFA9, and SVOPL; GCGR, BTN2A1, NDUFA9, and ZFYVE9; GCGR, BTN2A1, NDUFA9, and ZNF205; GCGR, BTN2A1, NEU2, and PLA2G1B; GCGR, BTN2A1, NEU2, and PYCR1; GCGR, BTN2A1, NEU2, and RAD51AP1; GCGR, BTN2A1, NEU2, and SEC61G; GCGR, BTN2A1, NEU2, and STRADA; GCGR, BTN2A1, NEU2, and SVOPL; GCGR, BTN2A1, NEU2, and ZFYVE9; GCGR, BTN2A1, NEU2, and ZNF205; GCGR, BTN2A1, PLA2G1B, and PYCR1; GCGR, BTN2A1, PLA2G1B, and RAD51AP1; GCGR, BTN2A1, PLA2G1B, and SEC61G; GCGR, BTN2A1, PLA2G1B, and STRADA; GCGR, BTN2A1, PLA2G1B, and SVOPL; GCGR, BTN2A1, PLA2G1B, and ZFYVE9; GCGR, BTN2A1, PLA2G1B, and ZNF205; GCGR, BTN2A1, PYCR1, and RAD51AP1; GCGR, BTN2A1, PYCR1, and SEC61G; GCGR, BTN2A1, PYCR1, and STRADA; GCGR, BTN2A1, PYCR1, and SVOPL; GCGR, BTN2A1, PYCR1, and ZFYVE9; GCGR, BTN2A1, PYCR1, and ZNF205; GCGR, BTN2A1, RAD51AP1, and SEC61G; GCGR, BTN2A1, RAD51AP1, and STRADA; GCGR, BTN2A1, RAD51AP1, and SVOPL; GCGR, BTN2A1, RAD51AP1, and ZFYVE9; GCGR, BTN2A1, RAD51AP1, and ZNF205; GCGR, BTN2A1, SEC61G, and STRADA; GCGR, BTN2A1, SEC61G, and SVOPL; GCGR, BTN2A1, SEC61G, and ZFYVE9; GCGR, BTN2A1, SEC61G, and ZNF205; GCGR, BTN2A1, STRADA, and SVOPL; GCGR, BTN2A1, STRADA, and ZFYVE9; GCGR, BTN2A1, STRADA, and ZNF205; GCGR, BTN2A1, SVOPL, and ZFYVE9; GCGR, BTN2A1, SVOPL, and ZNF205; GCGR, BTN2A1, ZFYVE9, and ZNF205; GCGR, CNTD2, COQ9, and EMX2; GCGR, CNTD2, COQ9, and EP300; GCGR, CNTD2, COQ9, and FGF2; GCGR, CNTD2, COQ9, and NAT9; GCGR, CNTD2, COQ9, and NDUFA9; GCGR, CNTD2, COQ9, and NEU2; GCGR, CNTD2, COQ9, and PLA2G1B; GCGR, CNTD2, COQ9, and PYCR1; GCGR, CNTD2, COQ9, and RAD51AP1; GCGR, CNTD2, COQ9, and SEC61G; GCGR, CNTD2, COQ9, and STRADA; GCGR, CNTD2, COQ9, and SVOPL; GCGR, CNTD2, COQ9, and ZFYVE9; GCGR, CNTD2, COQ9, and ZNF205; GCGR, CNTD2, EMX2, and EP300; GCGR, CNTD2, EMX2, and FGF2; GCGR, CNTD2, EMX2, and NAT9; GCGR, CNTD2, EMX2, and NDUFA9; GCGR, CNTD2, EMX2, and NEU2; GCGR, CNTD2, EMX2, and PLA2G1B; GCGR, CNTD2, EMX2, and PYCR1; GCGR, CNTD2, EMX2, and RAD51AP1; GCGR, CNTD2, EMX2, and SEC61G; GCGR, CNTD2, EMX2, and STRADA; GCGR, CNTD2, EMX2, and SVOPL; GCGR, CNTD2, EMX2, and ZFYVE9; GCGR, CNTD2, EMX2, and ZNF205; GCGR, CNTD2, EP300, and FGF2; GCGR, CNTD2, EP300, and NAT9; GCGR, CNTD2, EP300, and NDUFA9; GCGR, CNTD2, EP300, and NEU2; GCGR, CNTD2, EP300, and PLA2G1B; GCGR, CNTD2, EP300, and PYCR1; GCGR, CNTD2, EP300, and RAD51AP1; GCGR, CNTD2, EP300, and SEC61G; GCGR, CNTD2, EP300, and STRADA; GCGR, CNTD2, EP300, and SVOPL; GCGR, CNTD2, EP300, and ZFYVE9; GCGR, CNTD2, EP300, and ZNF205; GCGR, CNTD2, FGF2, and NAT9; GCGR, CNTD2, FGF2, and NDUFA9; GCGR, CNTD2, FGF2, and NEU2; GCGR, CNTD2, FGF2, and PLA2G1B; GCGR, CNTD2, FGF2, and PYCR1; GCGR, CNTD2, FGF2, and RAD51AP1; GCGR, CNTD2, FGF2, and SEC61G; GCGR, CNTD2, FGF2, and STRADA; GCGR, CNTD2, FGF2, and SVOPL; GCGR, CNTD2, FGF2, and ZFYVE9; GCGR, CNTD2, FGF2, and ZNF205; GCGR, CNTD2, NAT9, and NDUFA9; GCGR, CNTD2, NAT9, and NEU2; GCGR, CNTD2, NAT9, and PLA2G1B; GCGR, CNTD2, NAT9, and PYCR1; GCGR, CNTD2, NAT9, and RAD51AP1; GCGR, CNTD2, NAT9, and SEC61G; GCGR, CNTD2, NAT9, and STRADA; GCGR, CNTD2, NAT9, and SVOPL; GCGR, CNTD2, NAT9, and ZFYVE9; GCGR, CNTD2, NAT9, and ZNF205; GCGR, CNTD2, NDUFA9, and NEU2; GCGR, CNTD2, NDUFA9, and PLA2G1B; GCGR, CNTD2, NDUFA9, and PYCR1; GCGR, CNTD2, NDUFA9, and RAD51AP1; GCGR, CNTD2, NDUFA9, and SEC61G; GCGR, CNTD2, NDUFA9, and STRADA; GCGR, CNTD2, NDUFA9, and SVOPL; GCGR, CNTD2, NDUFA9, and ZFYVE9; GCGR, CNTD2, NDUFA9, and ZNF205; GCGR, CNTD2, NEU2, and PLA2G1B; GCGR, CNTD2, NEU2, and PYCR1; GCGR, CNTD2, NEU2, and RAD51AP1; GCGR, CNTD2, NEU2, and SEC61G; GCGR, CNTD2, NEU2, and STRADA; GCGR, CNTD2, NEU2, and SVOPL; GCGR, CNTD2, NEU2, and ZFYVE9; GCGR, CNTD2, NEU2, and ZNF205; GCGR, CNTD2, PLA2G1B, and PYCR1; GCGR, CNTD2, PLA2G1B, and RAD51AP1; GCGR, CNTD2, PLA2G1B, and SEC61G; GCGR, CNTD2, PLA2G1B, and STRADA; GCGR, CNTD2, PLA2G1B, and SVOPL; GCGR, CNTD2, PLA2G1B, and ZFYVE9; GCGR, CNTD2, PLA2G1B, and ZNF205; GCGR, CNTD2, PYCR1, and RAD51AP1; GCGR, CNTD2, PYCR1, and SEC61G; GCGR, CNTD2, PYCR1, and STRADA; GCGR, CNTD2, PYCR1, and SVOPL; GCGR, CNTD2, PYCR1, and ZFYVE9; GCGR, CNTD2, PYCR1, and ZNF205; GCGR, CNTD2, RAD51AP1, and SEC61G; GCGR, CNTD2, RAD51AP1, and STRADA; GCGR, CNTD2, RAD51AP1, and SVOPL; GCGR, CNTD2, RAD51AP1, and ZFYVE9; GCGR, CNTD2, RAD51AP1, and ZNF205; GCGR, CNTD2, SEC61G, and STRADA; GCGR, CNTD2, SEC61G, and SVOPL; GCGR, CNTD2, SEC61G, and ZFYVE9; GCGR, CNTD2, SEC61G, and ZNF205; GCGR, CNTD2, STRADA, and SVOPL; GCGR, CNTD2, STRADA, and ZFYVE9; GCGR, CNTD2, STRADA, and ZNF205; GCGR, CNTD2, SVOPL, and ZFYVE9; GCGR, CNTD2, SVOPL, and ZNF205; GCGR, CNTD2, ZFYVE9, and ZNF205; GCGR, COQ9, EMX2, and EP300; GCGR, COQ9, EMX2, and FGF2; GCGR, COQ9, EMX2, and NAT9; GCGR, COQ9, EMX2, and NDUFA9; GCGR, COQ9, EMX2, and NEU2; GCGR, COQ9, EMX2, and PLA2G1B; GCGR, COQ9, EMX2, and PYCR1; GCGR, COQ9, EMX2, and RAD51AP1; GCGR, COQ9, EMX2, and SEC61G; GCGR, COQ9, EMX2, and STRADA; GCGR, COQ9, EMX2, and SVOPL; GCGR, COQ9, EMX2, and ZFYVE9; GCGR, COQ9, EMX2, and ZNF205; GCGR, COQ9, EP300, and FGF2; GCGR, COQ9, EP300, and NAT9; GCGR, COQ9, EP300, and NDUFA9; GCGR, COQ9, EP300, and NEU2; GCGR, COQ9, EP300, and PLA2G1B; GCGR, COQ9, EP300, and PYCR1; GCGR, COQ9, EP300, and RAD51AP1; GCGR, COQ9, EP300, and SEC61G; GCGR, COQ9, EP300, and STRADA; GCGR, COQ9, EP300, and SVOPL; GCGR, COQ9, EP300, and ZFYVE9; GCGR, COQ9, EP300, and ZNF205; GCGR, COQ9, FGF2, and NAT9; GCGR, COQ9, FGF2, and NDUFA9; GCGR, COQ9, FGF2, and NEU2; GCGR, COQ9, FGF2, and PLA2G1B; GCGR, COQ9, FGF2, and PYCR1; GCGR, COQ9, FGF2, and RAD51AP1; GCGR, COQ9, FGF2, and SEC61G; GCGR, COQ9, FGF2, and STRADA; GCGR, COQ9, FGF2, and SVOPL; GCGR, COQ9, FGF2, and ZFYVE9; GCGR, COQ9, FGF2, and ZNF205; GCGR, COQ9, NAT9, and NDUFA9; GCGR, COQ9, NAT9, and NEU2; GCGR, COQ9, NAT9, and PLA2G1B; GCGR, COQ9, NAT9, and PYCR1; GCGR, COQ9, NAT9, and RAD51AP1; GCGR, COQ9, NAT9, and SEC61G; GCGR, COQ9, NAT9, and STRADA; GCGR, COQ9, NAT9, and SVOPL; GCGR, COQ9, NAT9, and ZFYVE9; GCGR, COQ9, NAT9, and ZNF205; GCGR, COQ9, NDUFA9, and NEU2; GCGR, COQ9, NDUFA9, and PLA2G1B; GCGR, COQ9, NDUFA9, and PYCR1; GCGR, COQ9, NDUFA9, and RAD51AP1; GCGR, COQ9, NDUFA9, and SEC61G; GCGR, COQ9, NDUFA9, and STRADA; GCGR, COQ9, NDUFA9, and SVOPL; GCGR, COQ9, NDUFA9, and ZFYVE9; GCGR, COQ9, NDUFA9, and ZNF205; GCGR, COQ9, NEU2, and PLA2G1B; GCGR, COQ9, NEU2, and PYCR1; GCGR, COQ9, NEU2, and RAD51AP1; GCGR, COQ9, NEU2, and SEC61G; GCGR, COQ9, NEU2, and STRADA; GCGR, COQ9, NEU2, and SVOPL; GCGR, COQ9, NEU2, and ZFYVE9; GCGR, COQ9, NEU2, and ZNF205; GCGR, COQ9, PLA2G1B, and PYCR1; GCGR, COQ9, PLA2G1B, and RAD51AP1; GCGR, COQ9, PLA2G1B, and SEC61G; GCGR, COQ9, PLA2G1B, and STRADA; GCGR, COQ9, PLA2G1B, and SVOPL; GCGR, COQ9, PLA2G1B, and ZFYVE9; GCGR, COQ9, PLA2G1B, and ZNF205; GCGR, COQ9, PYCR1, and RAD51AP1; GCGR, COQ9, PYCR1, and SEC61G; GCGR, COQ9, PYCR1, and STRADA; GCGR, COQ9, PYCR1, and SVOPL; GCGR, COQ9, PYCR1, and ZFYVE9; GCGR, COQ9, PYCR1, and ZNF205; GCGR, COQ9, RAD51AP1, and SEC61G; GCGR, COQ9, RAD51AP1, and STRADA; GCGR, COQ9, RAD51AP1, and SVOPL; GCGR, COQ9, RAD51AP1, and ZFYVE9; GCGR, COQ9, RAD51AP1, and ZNF205; GCGR, COQ9, SEC61G, and STRADA; GCGR, COQ9, SEC61G, and SVOPL; GCGR, COQ9, SEC61G, and ZFYVE9; GCGR, COQ9, SEC61G, and ZNF205; GCGR, COQ9, STRADA, and SVOPL; GCGR, COQ9, STRADA, and ZFYVE9; GCGR, COQ9, STRADA, and ZNF205; GCGR, COQ9, SVOPL, and ZFYVE9; GCGR, COQ9, SVOPL, and ZNF205; GCGR, COQ9, ZFYVE9, and ZNF205; GCGR, EMX2, EP300, and FGF2; GCGR, EMX2, EP300, and NAT9; GCGR, EMX2, EP300, and NDUFA9; GCGR, EMX2, EP300, and NEU2; GCGR, EMX2, EP300, and PLA2G1B; GCGR, EMX2, EP300, and PYCR1; GCGR, EMX2, EP300, and RAD51AP1; GCGR, EMX2, EP300, and SEC61G; GCGR, EMX2, EP300, and STRADA; GCGR, EMX2, EP300, and SVOPL; GCGR, EMX2, EP300, and ZFYVE9; GCGR, EMX2, EP300, and ZNF205; GCGR, EMX2, FGF2, and NAT9; GCGR, EMX2, FGF2, and NDUFA9; GCGR, EMX2, FGF2, and NEU2; GCGR, EMX2, FGF2, and PLA2G1B; GCGR, EMX2, FGF2, and PYCR1; GCGR, EMX2, FGF2, and RAD51AP1; GCGR, EMX2, FGF2, and SEC61G; GCGR, EMX2, FGF2, and STRADA; GCGR, EMX2, FGF2, and SVOPL; GCGR, EMX2, FGF2, and ZFYVE9; GCGR, EMX2, FGF2, and ZNF205; GCGR, EMX2, NAT9, and NDUFA9; GCGR, EMX2, NAT9, and NEU2; GCGR, EMX2, NAT9, and PLA2G1B; GCGR, EMX2, NAT9, and PYCR1; GCGR, EMX2, NAT9, and RAD51AP1; GCGR, EMX2, NAT9, and SEC61G; GCGR, EMX2, NAT9, and STRADA; GCGR, EMX2, NAT9, and SVOPL; GCGR, EMX2, NAT9, and ZFYVE9; GCGR, EMX2, NAT9, and ZNF205; GCGR, EMX2, NDUFA9, and NEU2; GCGR, EMX2, NDUFA9, and PLA2G1B; GCGR, EMX2, NDUFA9, and PYCR1; GCGR, EMX2, NDUFA9, and RAD51AP1; GCGR, EMX2, NDUFA9, and SEC61G; GCGR, EMX2, NDUFA9, and STRADA; GCGR, EMX2, NDUFA9, and SVOPL; GCGR, EMX2, NDUFA9, and ZFYVE9; GCGR, EMX2, NDUFA9, and ZNF205; GCGR, EMX2, NEU2, and PLA2G1B; GCGR, EMX2, NEU2, and PYCR1; GCGR, EMX2, NEU2, and RAD51AP1; GCGR, EMX2, NEU2, and SEC61G; GCGR, EMX2, NEU2, and STRADA; GCGR, EMX2, NEU2, and SVOPL; GCGR, EMX2, NEU2, and ZFYVE9; GCGR, EMX2, NEU2, and ZNF205; GCGR, EMX2, PLA2G1B, and PYCR1; GCGR, EMX2, PLA2G1B, and RAD51AP1; GCGR, EMX2, PLA2G1B, and SEC61G; GCGR, EMX2, PLA2G1B, and STRADA; GCGR, EMX2, PLA2G1B, and SVOPL; GCGR, EMX2, PLA2G1B, and ZFYVE9; GCGR, EMX2, PLA2G1B, and ZNF205; GCGR, EMX2, PYCR1, and RAD51AP1; GCGR, EMX2, PYCR1, and SEC61G; GCGR, EMX2, PYCR1, and STRADA; GCGR, EMX2, PYCR1, and SVOPL; GCGR, EMX2, PYCR1, and ZFYVE9; GCGR, EMX2, PYCR1, and ZNF205; GCGR, EMX2, RAD51AP1, and SEC61G; GCGR, EMX2, RAD51AP1, and STRADA; GCGR, EMX2, RAD51AP1, and SVOPL; GCGR, EMX2, RAD51AP1, and ZFYVE9; GCGR, EMX2, RAD51AP1, and ZNF205; GCGR, EMX2, SEC61G, and STRADA; GCGR, EMX2, SEC61G, and SVOPL; GCGR, EMX2, SEC61G, and ZFYVE9; GCGR, EMX2, SEC61G, and ZNF205; GCGR, EMX2, STRADA, and SVOPL; GCGR, EMX2, STRADA, and ZFYVE9; GCGR, EMX2, STRADA, and ZNF205; GCGR, EMX2, SVOPL, and ZFYVE9; GCGR, EMX2, SVOPL, and ZNF205; GCGR, EMX2, ZFYVE9, and ZNF205; GCGR, EP300, FGF2, and NAT9; GCGR, EP300, FGF2, and NDUFA9; GCGR, EP300, FGF2, and NEU2; GCGR, EP300, FGF2, and PLA2G1B; GCGR, EP300, FGF2, and PYCR1; GCGR, EP300, FGF2, and RAD51AP1; GCGR, EP300, FGF2, and SEC61G; GCGR, EP300, FGF2, and STRADA; GCGR, EP300, FGF2, and SVOPL; GCGR, EP300, FGF2, and ZFYVE9; GCGR, EP300, FGF2, and ZNF205; GCGR, EP300, NAT9, and NDUFA9; GCGR, EP300, NAT9, and NEU2; GCGR, EP300, NAT9, and PLA2G1B; GCGR, EP300, NAT9, and PYCR1; GCGR, EP300, NAT9, and RAD51AP1; GCGR, EP300, NAT9, and SEC61G; GCGR, EP300, NAT9, and STRADA; GCGR, EP300, NAT9, and SVOPL; GCGR, EP300, NAT9, and ZFYVE9; GCGR, EP300, NAT9, and ZNF205; GCGR, EP300, NDUFA9, and NEU2; GCGR, EP300, NDUFA9, and PLA2G1B; GCGR, EP300, NDUFA9, and PYCR1; GCGR, EP300, NDUFA9, and RAD51AP1; GCGR, EP300, NDUFA9, and SEC61G; GCGR, EP300, NDUFA9, and STRADA; GCGR, EP300, NDUFA9, and SVOPL; GCGR, EP300, NDUFA9, and ZFYVE9; GCGR, EP300, NDUFA9, and ZNF205; GCGR, EP300, NEU2, and PLA2G1B; GCGR, EP300, NEU2, and PYCR1; GCGR, EP300, NEU2, and RAD51AP1; GCGR, EP300, NEU2, and SEC61G; GCGR, EP300, NEU2, and STRADA; GCGR, EP300, NEU2, and SVOPL; GCGR, EP300, NEU2, and ZFYVE9; GCGR, EP300, NEU2, and ZNF205; GCGR, EP300, PLA2G1B, and PYCR1; GCGR, EP300, PLA2G1B, and RAD51AP1; GCGR, EP300, PLA2G1B, and SEC61G; GCGR, EP300, PLA2G1B, and STRADA; GCGR, EP300, PLA2G1B, and SVOPL; GCGR, EP300, PLA2G1B, and ZFYVE9; GCGR, EP300, PLA2G1B, and ZNF205; GCGR, EP300, PYCR1, and RAD51AP1; GCGR, EP300, PYCR1, and SEC61G; GCGR, EP300, PYCR1, and STRADA; GCGR, EP300, PYCR1, and SVOPL; GCGR, EP300, PYCR1, and ZFYVE9; GCGR, EP300, PYCR1, and ZNF205; GCGR, EP300, RAD51AP1, and SEC61G; GCGR, EP300, RAD51AP1, and STRADA; GCGR, EP300, RAD51AP1, and SVOPL; GCGR, EP300, RAD51AP1, and ZFYVE9; GCGR, EP300, RAD51AP1, and ZNF205; GCGR, EP300, SEC61G, and STRADA; GCGR, EP300, SEC61G, and SVOPL; GCGR, EP300, SEC61G, and ZFYVE9; GCGR, EP300, SEC61G, and ZNF205; GCGR, EP300, STRADA, and SVOPL; GCGR, EP300, STRADA, and ZFYVE9; GCGR, EP300, STRADA, and ZNF205; GCGR, EP300, SVOPL, and ZFYVE9; GCGR, EP300, SVOPL, and ZNF205; GCGR, EP300, ZFYVE9, and ZNF205; GCGR, FGF2, NAT9, and NDUFA9; GCGR, FGF2, NAT9, and NEU2; GCGR, FGF2, NAT9, and PLA2G1B; GCGR, FGF2, NAT9, and PYCR1; GCGR, FGF2, NAT9, and RAD51AP1; GCGR, FGF2, NAT9, and SEC61G; GCGR, FGF2, NAT9, and STRADA; GCGR, FGF2, NAT9, and SVOPL; GCGR, FGF2, NAT9, and ZFYVE9; GCGR, FGF2, NAT9, and ZNF205; GCGR, FGF2, NDUFA9, and NEU2; GCGR, FGF2, NDUFA9, and PLA2G1B; GCGR, FGF2, NDUFA9, and PYCR1; GCGR, FGF2, NDUFA9, and RAD51AP1; GCGR, FGF2, NDUFA9, and SEC61G; GCGR, FGF2, NDUFA9, and STRADA; GCGR, FGF2, NDUFA9, and SVOPL; GCGR, FGF2, NDUFA9, and ZFYVE9; GCGR, FGF2, NDUFA9, and ZNF205; GCGR, FGF2, NEU2, and PLA2G1B; GCGR, FGF2, NEU2, and PYCR1; GCGR, FGF2, NEU2, and RAD51AP1; GCGR, FGF2, NEU2, and SEC61G; GCGR, FGF2, NEU2, and STRADA; GCGR, FGF2, NEU2, and SVOPL; GCGR, FGF2, NEU2, and ZFYVE9; GCGR, FGF2, NEU2, and ZNF205; GCGR, FGF2, PLA2G1B, and PYCR1; GCGR, FGF2, PLA2G1B, and RAD51AP1; GCGR, FGF2, PLA2G1B, and SEC61G; GCGR, FGF2, PLA2G1B, and STRADA; GCGR, FGF2, PLA2G1B, and SVOPL; GCGR, FGF2, PLA2G1B, and ZFYVE9; GCGR, FGF2, PLA2G1B, and ZNF205; GCGR, FGF2, PYCR1, and RAD51AP1; GCGR, FGF2, PYCR1, and SEC61G; GCGR, FGF2, PYCR1, and STRADA; GCGR, FGF2, PYCR1, and SVOPL; GCGR, FGF2, PYCR1, and ZFYVE9; GCGR, FGF2, PYCR1, and ZNF205; GCGR, FGF2, RAD51AP1, and SEC61G; GCGR, FGF2, RAD51AP1, and STRADA; GCGR, FGF2, RAD51AP1, and SVOPL; GCGR, FGF2, RAD51AP1, and ZFYVE9; GCGR, FGF2, RAD51AP1, and ZNF205; GCGR, FGF2, SEC61G, and STRADA; GCGR, FGF2, SEC61G, and SVOPL; GCGR, FGF2, SEC61G, and ZFYVE9; GCGR, FGF2, SEC61G, and ZNF205; GCGR, FGF2, STRADA, and SVOPL; GCGR, FGF2, STRADA, and ZFYVE9; GCGR, FGF2, STRADA, and ZNF205; GCGR, FGF2, SVOPL, and ZFYVE9; GCGR, FGF2, SVOPL, and ZNF205; GCGR, FGF2, ZFYVE9, and ZNF205; GCGR, NAT9, NDUFA9, and NEU2; GCGR, NAT9, NDUFA9, and PLA2G1B; GCGR, NAT9, NDUFA9, and PYCR1; GCGR, NAT9, NDUFA9, and RAD51AP1; GCGR, NAT9, NDUFA9, and SEC61G; GCGR, NAT9, NDUFA9, and STRADA; GCGR, NAT9, NDUFA9, and SVOPL; GCGR, NAT9, NDUFA9, and ZFYVE9; GCGR, NAT9, NDUFA9, and ZNF205; GCGR, NAT9, NEU2, and PLA2G1B; GCGR, NAT9, NEU2, and PYCR1; GCGR, NAT9, NEU2, and RAD51AP1; GCGR, NAT9, NEU2, and SEC61G;

GCGR, NAT9, NEU2, and STRADA; GCGR, NAT9, NEU2, and SVOPL; GCGR, NAT9, NEU2, and ZFYVE9; GCGR, NAT9, NEU2, and ZNF205; GCGR, NAT9, PLA2G1B, and PYCR1; GCGR, NAT9, PLA2G1B, and RAD51AP1; GCGR, NAT9, PLA2G1B, and SEC61G; GCGR, NAT9, PLA2G1B, and STRADA; GCGR, NAT9, PLA2G1B, and SVOPL; GCGR, NAT9, PLA2G1B, and ZFYVE9; GCGR, NAT9, PLA2G1B, and ZNF205; GCGR, NAT9, PYCR1, and RAD51AP1; GCGR, NAT9, PYCR1, and SEC61G; GCGR, NAT9, PYCR1, and STRADA; GCGR, NAT9, PYCR1, and SVOPL; GCGR, NAT9, PYCR1, and ZFYVE9; GCGR, NAT9, PYCR1, and ZNF205; GCGR, NAT9, RAD51AP1, and SEC61G; GCGR, NAT9, RAD51AP1, and STRADA; GCGR, NAT9, RAD51AP1, and SVOPL; GCGR, NAT9, RAD51AP1, and ZFYVE9; GCGR, NAT9, RAD51AP1, and ZNF205; GCGR, NAT9, SEC61G, and STRADA; GCGR, NAT9, SEC61G, and SVOPL; GCGR, NAT9, SEC61G, and ZFYVE9; GCGR, NAT9, SEC61G, and ZNF205; GCGR, NAT9, STRADA, and SVOPL; GCGR, NAT9, STRADA, and ZFYVE9; GCGR, NAT9, STRADA, and ZNF205; GCGR, NAT9, SVOPL, and ZFYVE9; GCGR, NAT9, SVOPL, and ZNF205; GCGR, NAT9, ZFYVE9, and ZNF205; GCGR, NDUFA9, NEU2, and PLA2G1B; GCGR, NDUFA9, NEU2, and PYCR1; GCGR, NDUFA9, NEU2, and RAD51AP1; GCGR, NDUFA9, NEU2, and SEC61G; GCGR, NDUFA9, NEU2, and STRADA; GCGR, NDUFA9, NEU2, and SVOPL; GCGR, NDUFA9, NEU2, and ZFYVE9; GCGR, NDUFA9, NEU2, and ZNF205; GCGR, NDUFA9, PLA2G1B, and PYCR1; GCGR, NDUFA9, PLA2G1B, and RAD51AP1; GCGR, NDUFA9, PLA2G1B, and SEC61G; GCGR, NDUFA9, PLA2G1B, and STRADA; GCGR, NDUFA9, PLA2G1B, and SVOPL; GCGR, NDUFA9, PLA2G1B, and ZFYVE9; GCGR, NDUFA9, PLA2G1B, and ZNF205; GCGR, NDUFA9, PYCR1, and RAD51AP1; GCGR, NDUFA9, PYCR1, and SEC61G; GCGR, NDUFA9, PYCR1, and STRADA; GCGR, NDUFA9, PYCR1, and SVOPL; GCGR, NDUFA9, PYCR1, and ZFYVE9; GCGR, NDUFA9, PYCR1, and ZNF205; GCGR, NDUFA9, RAD51AP1, and SEC61G; GCGR, NDUFA9, RAD51AP1, and STRADA; GCGR, NDUFA9, RAD51AP1, and SVOPL; GCGR, NDUFA9, RAD51AP1, and ZFYVE9; GCGR, NDUFA9, RAD51AP1, and ZNF205; GCGR, NDUFA9, SEC61G, and STRADA; GCGR, NDUFA9, SEC61G, and SVOPL; GCGR, NDUFA9, SEC61G, and ZFYVE9; GCGR, NDUFA9, SEC61G, and ZNF205; GCGR, NDUFA9, STRADA, and SVOPL; GCGR, NDUFA9, STRADA, and ZFYVE9; GCGR, NDUFA9, STRADA, and ZNF205; GCGR, NDUFA9, SVOPL, and ZFYVE9; GCGR, NDUFA9, SVOPL, and ZNF205; GCGR, NDUFA9, ZFYVE9, and ZNF205; GCGR, NEU2, PLA2G1B, and PYCR1; GCGR, NEU2, PLA2G1B, and RAD51AP1; GCGR, NEU2, PLA2G1B, and SEC61G; GCGR, NEU2, PLA2G1B, and STRADA; GCGR, NEU2, PLA2G1B, and SVOPL; GCGR, NEU2, PLA2G1B, and ZFYVE9; GCGR, NEU2, PLA2G1B, and ZNF205; GCGR, NEU2, PYCR1, and RAD51AP1; GCGR, NEU2, PYCR1, and SEC61G; GCGR, NEU2, PYCR1, and STRADA; GCGR, NEU2, PYCR1, and SVOPL; GCGR, NEU2, PYCR1, and ZFYVE9; GCGR, NEU2, PYCR1, and ZNF205; GCGR, NEU2, RAD51AP1, and SEC61G; GCGR, NEU2, RAD51AP1, and STRADA; GCGR, NEU2, RAD51AP1, and SVOPL; GCGR, NEU2, RAD51AP1, and ZFYVE9; GCGR, NEU2, RAD51AP1, and ZNF205; GCGR, NEU2, SEC61G, and STRADA; GCGR, NEU2, SEC61G, and SVOPL; GCGR, NEU2, SEC61G, and ZFYVE9; GCGR, NEU2, SEC61G, and ZNF205; GCGR, NEU2, STRADA, and SVOPL; GCGR, NEU2, STRADA, and ZFYVE9; GCGR, NEU2, STRADA, and ZNF205; GCGR, NEU2, SVOPL, and ZFYVE9; GCGR, NEU2, SVOPL, and ZNF205; GCGR, NEU2, ZFYVE9, and ZNF205; GCGR, PLA2G1B, PYCR1, and RAD51AP1; GCGR, PLA2G1B, PYCR1, and SEC61G; GCGR, PLA2G1B, PYCR1, and STRADA; GCGR, PLA2G1B, PYCR1, and SVOPL; GCGR, PLA2G1B, PYCR1, and ZFYVE9; GCGR, PLA2G1B, PYCR1, and ZNF205; GCGR, PLA2G1B, RAD51AP1, and SEC61G; GCGR, PLA2G1B, RAD51AP1, and STRADA; GCGR, PLA2G1B, RAD51AP1, and SVOPL; GCGR, PLA2G1B, RAD51AP1, and ZFYVE9; GCGR, PLA2G1B, RAD51AP1, and ZNF205; GCGR, PLA2G1B, SEC61G, and STRADA; GCGR, PLA2G1B, SEC61G, and SVOPL; GCGR, PLA2G1B, SEC61G, and ZFYVE9; GCGR, PLA2G1B, SEC61G, and ZNF205; GCGR, PLA2G1B, STRADA, and SVOPL; GCGR, PLA2G1B, STRADA, and ZFYVE9; GCGR, PLA2G1B, STRADA, and ZNF205; GCGR, PLA2G1B, SVOPL, and ZFYVE9; GCGR, PLA2G1B, SVOPL, and ZNF205; GCGR, PLA2G1B, ZFYVE9, and ZNF205; GCGR, PYCR1, RAD51AP1, and SEC61G; GCGR, PYCR1, RAD51AP1, and STRADA; GCGR, PYCR1, RAD51AP1, and SVOPL; GCGR, PYCR1, RAD51AP1, and ZFYVE9; GCGR, PYCR1, RAD51AP1, and ZNF205; GCGR, PYCR1, SEC61G, and STRADA; GCGR, PYCR1, SEC61G, and SVOPL; GCGR, PYCR1, SEC61G, and ZFYVE9; GCGR, PYCR1, SEC61G, and ZNF205; GCGR, PYCR1, STRADA, and SVOPL; GCGR, PYCR1, STRADA, and ZFYVE9; GCGR, PYCR1, STRADA, and ZNF205; GCGR, PYCR1, SVOPL, and ZFYVE9; GCGR, PYCR1, SVOPL, and ZNF205; GCGR, PYCR1, ZFYVE9, and ZNF205; GCGR, RAD51AP1, SEC61G, and STRADA; GCGR, RAD51AP1, SEC61G, and SVOPL; GCGR, RAD51AP1, SEC61G, and ZFYVE9; GCGR, RAD51AP1, SEC61G, and ZNF205; GCGR, RAD51AP1, STRADA, and SVOPL; GCGR, RAD51AP1, STRADA, and ZFYVE9; GCGR, RAD51AP1, STRADA, and ZNF205; GCGR, RAD51AP1, SVOPL, and ZFYVE9; GCGR, RAD51AP1, SVOPL, and ZNF205; GCGR, RAD51AP1, ZFYVE9, and ZNF205; GCGR, SEC61G, STRADA, and SVOPL; GCGR, SEC61G, STRADA, and ZFYVE9; GCGR, SEC61G, STRADA, and ZNF205; GCGR, SEC61G, SVOPL, and ZFYVE9; GCGR, SEC61G, SVOPL, and ZNF205; GCGR, SEC61G, ZFYVE9, and ZNF205; GCGR, STRADA, SVOPL, and ZFYVE9; GCGR, STRADA, SVOPL, and ZNF205; GCGR, STRADA, ZFYVE9, and ZNF205; GCGR, SVOPL, ZFYVE9, and ZNF205; GCGR, BTN2A1, CNTD2, COQ9, and EMX2; GCGR, BTN2A1, CNTD2, COQ9, and EP300; GCGR, BTN2A1, CNTD2, COQ9, and FGF2; GCGR, BTN2A1, CNTD2, COQ9, and NAT9; GCGR, BTN2A1, CNTD2, COQ9, and NDUFA9; GCGR, BTN2A1, CNTD2, COQ9, and NEU2; GCGR, BTN2A1, CNTD2, COQ9, and PLA2G1B; GCGR, BTN2A1, CNTD2, COQ9, and PYCR1; GCGR, BTN2A1, CNTD2, COQ9, and RAD51AP1; GCGR, BTN2A1, CNTD2, COQ9, and SEC61G; GCGR, BTN2A1, CNTD2, COQ9, and STRADA; GCGR, BTN2A1, CNTD2, COQ9, and SVOPL; GCGR, BTN2A1, CNTD2, COQ9, and ZFYVE9; GCGR, BTN2A1, CNTD2, COQ9, and ZNF205; GCGR, BTN2A1, CNTD2, EMX2, and EP300; GCGR, BTN2A1, CNTD2, EMX2, and FGF2; GCGR, BTN2A1, CNTD2, EMX2, and NAT9; GCGR, BTN2A1, CNTD2, EMX2, and NDUFA9; GCGR, BTN2A1, CNTD2, EMX2, and NEU2; GCGR, BTN2A1, CNTD2, EMX2, and PLA2G1B; GCGR, BTN2A1, CNTD2, EMX2, and PYCR1; GCGR, BTN2A1, CNTD2, EMX2, and RAD51AP1; GCGR, BTN2A1, CNTD2, EMX2, and SEC61G; GCGR, BTN2A1, CNTD2, EMX2, and STRADA; GCGR, BTN2A1, CNTD2, EMX2, and SVOPL; GCGR, BTN2A1, CNTD2, EMX2, and ZFYVE9; GCGR, BTN2A1, CNTD2, EMX2, and ZNF205; GCGR, BTN2A1, CNTD2, EP300, and FGF2; GCGR, BTN2A1, CNTD2, EP300, and NAT9; GCGR, BTN2A1, CNTD2, EP300, and NDUFA9; GCGR, BTN2A1, CNTD2, EP300, and NEU2; GCGR, BTN2A1, CNTD2, EP300, and PLA2G1B; GCGR, BTN2A1, CNTD2, EP300, and PYCR1; GCGR, BTN2A1, CNTD2, EP300, and RAD51AP1; GCGR, BTN2A1, CNTD2, EP300, and SEC61G; GCGR, BTN2A1, CNTD2, EP300, and STRADA; GCGR, BTN2A1, CNTD2, EP300, and SVOPL; GCGR, BTN2A1, CNTD2, EP300, and ZFYVE9; GCGR, BTN2A1, CNTD2, EP300, and ZNF205; GCGR, BTN2A1, CNTD2, FGF2, and NAT9; GCGR, BTN2A1, CNTD2, FGF2, and NDUFA9; GCGR, BTN2A1, CNTD2, FGF2, and NEU2; GCGR, BTN2A1, CNTD2, FGF2, and PLA2G1B; GCGR, BTN2A1, CNTD2, FGF2, and PYCR1; GCGR, BTN2A1, CNTD2, FGF2, and RAD51AP1; GCGR, BTN2A1, CNTD2, FGF2, and SEC61G; GCGR, BTN2A1, CNTD2, FGF2, and STRADA; GCGR, BTN2A1, CNTD2, FGF2, and SVOPL; GCGR, BTN2A1, CNTD2, FGF2, and ZFYVE9; GCGR, BTN2A1, CNTD2, FGF2, and ZNF205; GCGR, BTN2A1, CNTD2, NAT9, and NDUFA9; GCGR, BTN2A1, CNTD2, NAT9, and NEU2; GCGR, BTN2A1, CNTD2, NAT9, and PLA2G1B; GCGR, BTN2A1, CNTD2, NAT9, and PYCR1; GCGR, BTN2A1, CNTD2, NAT9, and RAD51AP1; GCGR, BTN2A1, CNTD2, NAT9, and SEC61G; GCGR, BTN2A1, CNTD2, NAT9, and STRADA; GCGR, BTN2A1, CNTD2, NAT9, and SVOPL; GCGR, BTN2A1, CNTD2, NAT9, and ZFYVE9; GCGR, BTN2A1, CNTD2, NAT9, and ZNF205; GCGR, BTN2A1, CNTD2, NDUFA9, and NEU2; GCGR, BTN2A1, CNTD2, NDUFA9, and PLA2G1B; GCGR, BTN2A1, CNTD2, NDUFA9, and PYCR1; GCGR, BTN2A1, CNTD2, NDUFA9, and RAD51AP1; GCGR, BTN2A1, CNTD2, NDUFA9, and SEC61G; GCGR, BTN2A1, CNTD2, NDUFA9, and STRADA; GCGR, BTN2A1, CNTD2, NDUFA9, and SVOPL; GCGR, BTN2A1, CNTD2, NDUFA9, and ZFYVE9; GCGR, BTN2A1, CNTD2, NDUFA9, and ZNF205; GCGR, BTN2A1, CNTD2, NEU2, and PLA2G1B; GCGR, BTN2A1, CNTD2, NEU2, and PYCR1; GCGR, BTN2A1, CNTD2, NEU2, and RAD51AP1; GCGR, BTN2A1, CNTD2, NEU2, and SEC61G; GCGR, BTN2A1, CNTD2, NEU2, and STRADA; GCGR, BTN2A1, CNTD2, NEU2, and SVOPL; GCGR, BTN2A1, CNTD2, NEU2, and ZFYVE9; GCGR, BTN2A1, CNTD2, NEU2, and ZNF205; GCGR, BTN2A1, CNTD2, PLA2G1B, and PYCR1; GCGR, BTN2A1, CNTD2, PLA2G1B, and RAD51AP1; GCGR, BTN2A1, CNTD2, PLA2G1B, and SEC61G; GCGR, BTN2A1, CNTD2, PLA2G1B, and STRADA; GCGR, BTN2A1, CNTD2, PLA2G1B, and SVOPL; GCGR, BTN2A1, CNTD2, PLA2G1B, and ZFYVE9; GCGR, BTN2A1, CNTD2, PLA2G1B, and ZNF205; GCGR, BTN2A1, CNTD2, PYCR1, and RAD51AP1; GCGR, BTN2A1, CNTD2, PYCR1, and SEC61G; GCGR, BTN2A1, CNTD2, PYCR1, and STRADA; GCGR, BTN2A1, CNTD2, PYCR1, and SVOPL; GCGR, BTN2A1, CNTD2, PYCR1, and ZFYVE9; GCGR, BTN2A1, CNTD2, PYCR1, and ZNF205; GCGR, BTN2A1, CNTD2, RAD51AP1, and SEC61G; GCGR, BTN2A1, CNTD2, RAD51AP1, and STRADA; GCGR, BTN2A1, CNTD2, RAD51AP1, and SVOPL; GCGR, BTN2A1, CNTD2, RAD51AP1, and ZFYVE9; GCGR, BTN2A1, CNTD2, RAD51AP1, and ZNF205; GCGR, BTN2A1, CNTD2, SEC61G, and STRADA; GCGR, BTN2A1, CNTD2, SEC61G, and SVOPL; GCGR, BTN2A1, CNTD2, SEC61G, and ZFYVE9; GCGR, BTN2A1, CNTD2, SEC61G, and ZNF205; GCGR, BTN2A1, CNTD2, STRADA, and SVOPL; GCGR, BTN2A1, CNTD2, STRADA, and ZFYVE9; GCGR, BTN2A1, CNTD2, STRADA, and ZNF205; GCGR, BTN2A1, CNTD2, SVOPL, and ZFYVE9; GCGR, BTN2A1, CNTD2, SVOPL, and ZNF205; GCGR, BTN2A1, CNTD2, ZFYVE9, and ZNF205; GCGR, BTN2A1, COQ9, EMX2, and EP300; GCGR, BTN2A1, COQ9, EMX2, and FGF2; GCGR, BTN2A1, COQ9, EMX2, and NAT9; GCGR, BTN2A1, COQ9, EMX2, and NDUFA9; GCGR, BTN2A1, COQ9, EMX2, and NEU2; GCGR, BTN2A1, COQ9, EMX2, and PLA2G1B; GCGR, BTN2A1, COQ9, EMX2, and PYCR1; GCGR, BTN2A1, COQ9, EMX2, and RAD51AP1; GCGR, BTN2A1, COQ9, EMX2, and SEC61G; GCGR, BTN2A1, COQ9, EMX2, and STRADA; GCGR, BTN2A1, COQ9, EMX2, and SVOPL; GCGR, BTN2A1, COQ9, EMX2, and ZFYVE9; GCGR, BTN2A1, COQ9, EMX2, and ZNF205; GCGR, BTN2A1, COQ9, EP300, and FGF2; GCGR, BTN2A1, COQ9, EP300, and NAT9; GCGR, BTN2A1, COQ9, EP300, and NDUFA9; GCGR, BTN2A1, COQ9, EP300, and NEU2; GCGR, BTN2A1, COQ9, EP300, and PLA2G1B; GCGR, BTN2A1, COQ9, EP300, and PYCR1; GCGR, BTN2A1, COQ9, EP300, and RAD51AP1; GCGR, BTN2A1, COQ9, EP300, and SEC61G; GCGR, BTN2A1, COQ9, EP300, and STRADA; GCGR, BTN2A1, COQ9, EP300, and SVOPL; GCGR, BTN2A1, COQ9, EP300, and ZFYVE9; GCGR, BTN2A1, COQ9, EP300, and ZNF205; GCGR, BTN2A1, COQ9, FGF2, and NAT9; GCGR, BTN2A1, COQ9, FGF2, and NDUFA9; GCGR, BTN2A1, COQ9, FGF2, and NEU2; GCGR, BTN2A1, COQ9, FGF2, and PLA2G1B; GCGR, BTN2A1, COQ9, FGF2, and PYCR1; GCGR, BTN2A1, COQ9, FGF2, and RAD51AP1; GCGR, BTN2A1, COQ9, FGF2, and SEC61G; GCGR, BTN2A1, COQ9, FGF2, and STRADA; GCGR, BTN2A1, COQ9, FGF2, and SVOPL; GCGR, BTN2A1, COQ9, FGF2, and ZFYVE9; GCGR, BTN2A1, COQ9, FGF2, and ZNF205; GCGR, BTN2A1, COQ9, NAT9, and NDUFA9; GCGR, BTN2A1, COQ9, NAT9, and NEU2; GCGR, BTN2A1, COQ9, NAT9, and PLA2G1B; GCGR, BTN2A1, COQ9, NAT9, and PYCR1; GCGR, BTN2A1, COQ9, NAT9, and RAD51AP1; GCGR, BTN2A1, COQ9, NAT9, and SEC61G; GCGR, BTN2A1, COQ9, NAT9, and STRADA; GCGR, BTN2A1, COQ9, NAT9, and SVOPL; GCGR, BTN2A1, COQ9, NAT9, and ZFYVE9; GCGR, BTN2A1, COQ9, NAT9, and ZNF205; GCGR, BTN2A1, COQ9, NDUFA9, and NEU2; GCGR, BTN2A1, COQ9, NDUFA9, and PLA2G1B; GCGR, BTN2A1, COQ9, NDUFA9, and PYCR1; GCGR, BTN2A1, COQ9, NDUFA9, and RAD51AP1; GCGR, BTN2A1, COQ9, NDUFA9, and SEC61G; GCGR, BTN2A1, COQ9, NDUFA9, and STRADA; GCGR, BTN2A1, COQ9, NDUFA9, and SVOPL; GCGR, BTN2A1, COQ9, NDUFA9, and ZFYVE9; GCGR, BTN2A1, COQ9, NDUFA9, and ZNF205; GCGR, BTN2A1, COQ9, NEU2, and PLA2G1B; GCGR, BTN2A1, COQ9, NEU2, and PYCR1; GCGR, BTN2A1, COQ9, NEU2, and RAD51AP1; GCGR, BTN2A1, COQ9, NEU2, and SEC61G; GCGR, BTN2A1, COQ9, NEU2, and STRADA; GCGR, BTN2A1, COQ9, NEU2, and SVOPL; GCGR, BTN2A1, COQ9, NEU2, and ZFYVE9; GCGR, BTN2A1, COQ9, NEU2, and ZNF205; GCGR, BTN2A1, COQ9, PLA2G1B, and PYCR1; GCGR, BTN2A1, COQ9, PLA2G1B, and RAD51AP1; GCGR, BTN2A1, COQ9, PLA2G1B, and SEC61G; GCGR, BTN2A1, COQ9, PLA2G1B, and STRADA; GCGR, BTN2A1, COQ9, PLA2G1B, and SVOPL; GCGR, BTN2A1, COQ9, PLA2G1B, and ZFYVE9; GCGR, BTN2A1, COQ9, PLA2G1B, and ZNF205; GCGR, BTN2A1, COQ9, PYCR1, and RAD51AP1; GCGR, BTN2A1, COQ9, PYCR1, and SEC61G; GCGR, BTN2A1, COQ9, PYCR1, and STRADA; GCGR, BTN2A1, COQ9, PYCR1, and SVOPL; GCGR, BTN2A1, COQ9, PYCR1, and ZFYVE9; GCGR, BTN2A1, COQ9, PYCR1, and ZNF205; GCGR, BTN2A1, COQ9, RAD51AP1, and SEC61G; GCGR, BTN2A1, COQ9, RAD51AP1, and STRADA; GCGR, BTN2A1, COQ9, RAD51AP1, and SVOPL; GCGR, BTN2A1, COQ9, RAD51AP1, and ZFYVE9; GCGR, BTN2A1, COQ9, RAD51AP1, and ZNF205; GCGR, BTN2A1, COQ9, SEC61G, and STRADA; GCGR, BTN2A1, COQ9, SEC61G, and SVOPL; GCGR, BTN2A1, COQ9, SEC61G, and ZFYVE9; GCGR, BTN2A1, COQ9, SEC61G, and ZNF205; GCGR, BTN2A1, COQ9, STRADA, and SVOPL; GCGR, BTN2A1, COQ9, STRADA, and ZFYVE9; GCGR, BTN2A1, COQ9, STRADA, and ZNF205; GCGR, BTN2A1, COQ9, SVOPL, and ZFYVE9; GCGR, BTN2A1, COQ9, SVOPL, and ZNF205; GCGR, BTN2A1, COQ9, ZFYVE9, and ZNF205; GCGR, BTN2A1, EMX2, EP300, and FGF2; GCGR, BTN2A1, EMX2, EP300, and NAT9; GCGR, BTN2A1, EMX2, EP300, and NDUFA9; GCGR, BTN2A1, EMX2, EP300, and NEU2; GCGR, BTN2A1, EMX2, EP300, and PLA2G1B; GCGR, BTN2A1, EMX2, EP300, and PYCR1; GCGR, BTN2A1, EMX2, EP300, and RAD51AP1; GCGR, BTN2A1, EMX2, EP300, and SEC61G; GCGR, BTN2A1, EMX2, EP300, and STRADA; GCGR, BTN2A1, EMX2, EP300, and SVOPL; GCGR, BTN2A1, EMX2, EP300, and ZFYVE9; GCGR, BTN2A1, EMX2, EP300, and ZNF205; GCGR, BTN2A1, EMX2, FGF2, and NAT9; GCGR, BTN2A1, EMX2, FGF2, and NDUFA9; GCGR, BTN2A1, EMX2, FGF2, and NEU2; GCGR, BTN2A1, EMX2, FGF2, and PLA2G1B; GCGR, BTN2A1, EMX2, FGF2, and PYCR1; GCGR, BTN2A1, EMX2, FGF2, and RAD51AP1; GCGR, BTN2A1, EMX2, FGF2, and SEC61G; GCGR, BTN2A1, EMX2, FGF2, and STRADA; GCGR, BTN2A1, EMX2, FGF2, and SVOPL; GCGR, BTN2A1, EMX2, FGF2, and ZFYVE9; GCGR, BTN2A1, EMX2, FGF2, and ZNF205; GCGR, BTN2A1, EMX2, NAT9, and NDUFA9; GCGR, BTN2A1, EMX2, NAT9, and NEU2; GCGR, BTN2A1, EMX2, NAT9, and PLA2G1B; GCGR, BTN2A1, EMX2, NAT9, and PYCR1; GCGR, BTN2A1, EMX2, NAT9, and RAD51AP1; GCGR, BTN2A1, EMX2, NAT9, and SEC61G; GCGR, BTN2A1, EMX2, NAT9, and STRADA; GCGR, BTN2A1, EMX2, NAT9, and SVOPL; GCGR, BTN2A1, EMX2, NAT9, and ZFYVE9; GCGR, BTN2A1, EMX2, NAT9, and ZNF205; GCGR, BTN2A1, EMX2, NDUFA9, and NEU2; GCGR, BTN2A1, EMX2, NDUFA9, and PLA2G1B; GCGR, BTN2A1, EMX2, NDUFA9, and PYCR1; GCGR, BTN2A1, EMX2, NDUFA9, and RAD51AP1; GCGR, BTN2A1, EMX2, NDUFA9, and SEC61G; GCGR, BTN2A1, EMX2, NDUFA9, and STRADA; GCGR, BTN2A1, EMX2, NDUFA9, and SVOPL; GCGR, BTN2A1, EMX2, NDUFA9, and ZFYVE9; GCGR, BTN2A1, EMX2, NDUFA9, and ZNF205; GCGR, BTN2A1, EMX2, NEU2, and PLA2G1B; GCGR, BTN2A1, EMX2, NEU2, and PYCR1; GCGR, BTN2A1, EMX2, NEU2, and RAD51AP1; GCGR, BTN2A1, EMX2, NEU2, and SEC61G; GCGR, BTN2A1, EMX2, NEU2, and STRADA; GCGR, BTN2A1, EMX2, NEU2, and SVOPL; GCGR, BTN2A1, EMX2, NEU2, and ZFYVE9; GCGR, BTN2A1, EMX2, NEU2, and ZNF205; GCGR, BTN2A1, EMX2, PLA2G1B, and PYCR1; GCGR, BTN2A1, EMX2, PLA2G1B, and RAD51AP1; GCGR, BTN2A1, EMX2, PLA2G1B, and SEC61G; GCGR, BTN2A1, EMX2, PLA2G1B, and STRADA; GCGR, BTN2A1, EMX2, PLA2G1B, and SVOPL; GCGR, BTN2A1, EMX2, PLA2G1B, and ZFYVE9; GCGR, BTN2A1, EMX2, PLA2G1B, and ZNF205; GCGR, BTN2A1, EMX2, PYCR1, and RAD51AP1; GCGR, BTN2A1, EMX2, PYCR1, and SEC61G; GCGR, BTN2A1, EMX2, PYCR1, and STRADA; GCGR, BTN2A1, EMX2, PYCR1, and SVOPL; GCGR, BTN2A1, EMX2, PYCR1, and ZFYVE9; GCGR, BTN2A1, EMX2, PYCR1, and ZNF205; GCGR, BTN2A1, EMX2, RAD51AP1, and SEC61G; GCGR, BTN2A1, EMX2, RAD51AP1, and STRADA; GCGR, BTN2A1, EMX2, RAD51AP1, and SVOPL; GCGR, BTN2A1, EMX2, RAD51AP1, and ZFYVE9; GCGR, BTN2A1, EMX2, RAD51AP1, and ZNF205; GCGR, BTN2A1, EMX2, SEC61G, and STRADA; GCGR, BTN2A1, EMX2, SEC61G, and SVOPL; GCGR, BTN2A1, EMX2, SEC61G, and ZFYVE9; GCGR, BTN2A1, EMX2, SEC61G, and ZNF205; GCGR, BTN2A1, EMX2, STRADA, and SVOPL; GCGR, BTN2A1, EMX2, STRADA, and ZFYVE9; GCGR, BTN2A1, EMX2, STRADA, and ZNF205; GCGR, BTN2A1, EMX2, SVOPL, and ZFYVE9; GCGR, BTN2A1, EMX2, SVOPL, and ZNF205; GCGR, BTN2A1, EMX2, ZFYVE9, and ZNF205; GCGR, BTN2A1, EP300, FGF2, and NAT9; GCGR, BTN2A1, EP300, FGF2, and NDUFA9; GCGR, BTN2A1, EP300, FGF2, and NEU2; GCGR, BTN2A1, EP300, FGF2, and PLA2G1B; GCGR, BTN2A1, EP300, FGF2, and PYCR1; GCGR, BTN2A1, EP300, FGF2, and RAD51AP1; GCGR, BTN2A1, EP300, FGF2, and SEC61G; GCGR, BTN2A1, EP300, FGF2, and STRADA; GCGR, BTN2A1, EP300, FGF2, and SVOPL; GCGR, BTN2A1, EP300, FGF2, and ZFYVE9; GCGR, BTN2A1, EP300, FGF2, and ZNF205; GCGR, BTN2A1, EP300, NAT9, and NDUFA9; GCGR, BTN2A1, EP300, NAT9, and NEU2; GCGR, BTN2A1, EP300, NAT9, and PLA2G1B; GCGR, BTN2A1, EP300, NAT9, and PYCR1; GCGR, BTN2A1, EP300, NAT9, and RAD51AP1; GCGR, BTN2A1, EP300, NAT9, and SEC61G; GCGR, BTN2A1, EP300, NAT9, and STRADA; GCGR, BTN2A1, EP300, NAT9, and SVOPL; GCGR, BTN2A1, EP300, NAT9, and ZFYVE9; GCGR, BTN2A1, EP300, NAT9, and ZNF205; GCGR, BTN2A1, EP300, NDUFA9, and NEU2; GCGR, BTN2A1, EP300, NDUFA9, and PLA2G1B; GCGR, BTN2A1, EP300, NDUFA9, and PYCR1; GCGR, BTN2A1, EP300, NDUFA9, and RAD51AP1; GCGR, BTN2A1, EP300, NDUFA9, and SEC61G; GCGR, BTN2A1, EP300, NDUFA9, and STRADA; GCGR, BTN2A1, EP300, NDUFA9, and SVOPL; GCGR, BTN2A1, EP300, NDUFA9, and ZFYVE9; GCGR, BTN2A1, EP300, NDUFA9, and ZNF205; GCGR, BTN2A1, EP300, NEU2, and PLA2G1B; GCGR, BTN2A1, EP300, NEU2, and PYCR1; GCGR, BTN2A1, EP300, NEU2, and RAD51AP1; GCGR, BTN2A1, EP300, NEU2, and SEC61G; GCGR, BTN2A1, EP300, NEU2, and STRADA; GCGR, BTN2A1, EP300, NEU2, and SVOPL; GCGR, BTN2A1, EP300, NEU2, and ZFYVE9; GCGR, BTN2A1, EP300, NEU2, and ZNF205; GCGR, BTN2A1, EP300, PLA2G1B, and PYCR1; GCGR, BTN2A1, EP300, PLA2G1B, and RAD51AP1; GCGR, BTN2A1, EP300, PLA2G1B, and SEC61G; GCGR, BTN2A1, EP300, PLA2G1B, and STRADA; GCGR, BTN2A1, EP300, PLA2G1B, and SVOPL; GCGR, BTN2A1, EP300, PLA2G1B, and ZFYVE9; GCGR, BTN2A1, EP300, PLA2G1B, and ZNF205; GCGR, BTN2A1, EP300, PYCR1, and RAD51AP1; GCGR, BTN2A1, EP300, PYCR1, and SEC61G; GCGR, BTN2A1, EP300, PYCR1, and STRADA; GCGR, BTN2A1, EP300, PYCR1, and SVOPL; GCGR, BTN2A1, EP300, PYCR1, and ZFYVE9; GCGR, BTN2A1, EP300, PYCR1, and ZNF205; GCGR, BTN2A1, EP300, RAD51AP1, and SEC61G; GCGR, BTN2A1, EP300, RAD51AP1, and STRADA; GCGR, BTN2A1, EP300, RAD51AP1, and SVOPL; GCGR, BTN2A1, EP300, RAD51AP1, and ZFYVE9; GCGR, BTN2A1, EP300, RAD51AP1, and ZNF205; GCGR, BTN2A1, EP300, SEC61G, and STRADA; GCGR, BTN2A1, EP300, SEC61G, and SVOPL; GCGR, BTN2A1, EP300, SEC61G, and ZFYVE9; GCGR, BTN2A1, EP300, SEC61G, and ZNF205; GCGR, BTN2A1, EP300, STRADA, and SVOPL; GCGR, BTN2A1, EP300, STRADA, and ZFYVE9; GCGR, BTN2A1, EP300, STRADA, and ZNF205; GCGR, BTN2A1, EP300, SVOPL, and ZFYVE9; GCGR, BTN2A1, EP300, SVOPL, and ZNF205; GCGR, BTN2A1, EP300, ZFYVE9, and ZNF205; GCGR, BTN2A1, FGF2, NAT9, and NDUFA9; GCGR, BTN2A1, FGF2, NAT9, and NEU2; GCGR, BTN2A1, FGF2, NAT9, and PLA2G1B; GCGR, BTN2A1, FGF2, NAT9, and PYCR1; GCGR, BTN2A1, FGF2, NAT9, and RAD51AP1; GCGR, BTN2A1, FGF2, NAT9, and SEC61G; GCGR, BTN2A1, FGF2, NAT9, and STRADA; GCGR, BTN2A1, FGF2, NAT9, and SVOPL; GCGR, BTN2A1, FGF2, NAT9, and ZFYVE9; GCGR, BTN2A1, FGF2, NAT9, and ZNF205; GCGR, BTN2A1, FGF2, NDUFA9, and NEU2; GCGR, BTN2A1, FGF2, NDUFA9, and PLA2G1B; GCGR, BTN2A1, FGF2, NDUFA9, and PYCR1; GCGR, BTN2A1, FGF2, NDUFA9, and RAD51AP1; GCGR, BTN2A1, FGF2, NDUFA9, and SEC61G; GCGR, BTN2A1, FGF2, NDUFA9, and STRADA; GCGR, BTN2A1, FGF2, NDUFA9, and SVOPL; GCGR, BTN2A1, FGF2, NDUFA9, and ZFYVE9; GCGR, BTN2A1, FGF2, NDUFA9, and ZNF205; GCGR, BTN2A1, FGF2, NEU2, and PLA2G1B; GCGR, BTN2A1, FGF2, NEU2, and PYCR1; GCGR, BTN2A1, FGF2, NEU2, and RAD51AP1; GCGR, BTN2A1, FGF2, NEU2, and SEC61G; GCGR, BTN2A1, FGF2, NEU2, and STRADA; GCGR, BTN2A1, FGF2, NEU2, and SVOPL; GCGR, BTN2A1, FGF2, NEU2, and ZFYVE9; GCGR, BTN2A1, FGF2, NEU2, and ZNF205; GCGR, BTN2A1, FGF2, PLA2G1B, and PYCR1; GCGR, BTN2A1, FGF2, PLA2G1B, and RAD51AP1; GCGR, BTN2A1, FGF2, PLA2G1B, and SEC61G; GCGR, BTN2A1, FGF2, PLA2G1B, and STRADA; GCGR, BTN2A1, FGF2, PLA2G1B, and SVOPL; GCGR, BTN2A1, FGF2, PLA2G1B, and ZFYVE9; GCGR, BTN2A1, FGF2, PLA2G1B, and ZNF205; GCGR, BTN2A1, FGF2, PYCR1, and RAD51AP1; GCGR, BTN2A1, FGF2, PYCR1, and SEC61G; GCGR, BTN2A1, FGF2, PYCR1, and STRADA; GCGR, BTN2A1, FGF2, PYCR1, and SVOPL; GCGR, BTN2A1, FGF2, PYCR1, and ZFYVE9; GCGR, BTN2A1, FGF2, PYCR1, and ZNF205; GCGR, BTN2A1, FGF2, RAD51AP1, and SEC61G; GCGR, BTN2A1, FGF2, RAD51AP1, and STRADA; GCGR, BTN2A1, FGF2, RAD51AP1, and SVOPL; GCGR, BTN2A1, FGF2, RAD51AP1, and ZFYVE9; GCGR, BTN2A1, FGF2, RAD51AP1, and ZNF205; GCGR, BTN2A1, FGF2, SEC61G, and STRADA; GCGR, BTN2A1, FGF2, SEC61G, and SVOPL; GCGR, BTN2A1, FGF2, SEC61G, and ZFYVE9; GCGR, BTN2A1, FGF2, SEC61G, and ZNF205; GCGR, BTN2A1, FGF2, STRADA, and SVOPL; GCGR, BTN2A1, FGF2, STRADA, and ZFYVE9; GCGR, BTN2A1, FGF2, STRADA, and ZNF205; GCGR, BTN2A1, FGF2, SVOPL, and ZFYVE9; GCGR, BTN2A1, FGF2, SVOPL, and ZNF205; GCGR, BTN2A1, FGF2, ZFYVE9, and ZNF205; GCGR, BTN2A1, NAT9, NDUFA9, and NEU2; GCGR, BTN2A1, NAT9, NDUFA9, and PLA2G1B; GCGR, BTN2A1, NAT9, NDUFA9, and PYCR1; GCGR, BTN2A1, NAT9, NDUFA9, and RAD51AP1; GCGR, BTN2A1, NAT9, NDUFA9, and SEC61G; GCGR, BTN2A1, NAT9, NDUFA9, and STRADA; GCGR, BTN2A1, NAT9, NDUFA9, and SVOPL; GCGR, BTN2A1, NAT9, NDUFA9, and ZFYVE9; GCGR, BTN2A1, NAT9, NDUFA9, and ZNF205; GCGR, BTN2A1, NAT9, NEU2, and PLA2G1B; GCGR, BTN2A1, NAT9, NEU2, and PYCR1; GCGR, BTN2A1, NAT9, NEU2, and RAD51AP1; GCGR, BTN2A1, NAT9, NEU2, and SEC61G; GCGR, BTN2A1, NAT9, NEU2, and STRADA; GCGR, BTN2A1, NAT9, NEU2, and SVOPL; GCGR, BTN2A1, NAT9, NEU2, and ZFYVE9; GCGR, BTN2A1, NAT9, NEU2, and ZNF205; GCGR, BTN2A1, NAT9, PLA2G1B, and PYCR1; GCGR, BTN2A1, NAT9, PLA2G1B, and RAD51AP1; GCGR, BTN2A1, NAT9, PLA2G1B, and SEC61G; GCGR, BTN2A1, NAT9, PLA2G1B, and STRADA; GCGR, BTN2A1, NAT9, PLA2G1B, and SVOPL; GCGR, BTN2A1, NAT9, PLA2G1B, and ZFYVE9; GCGR, BTN2A1, NAT9, PLA2G1B, and ZNF205; GCGR, BTN2A1, NAT9, PYCR1, and RAD51AP1; GCGR, BTN2A1, NAT9, PYCR1, and SEC61G; GCGR, BTN2A1, NAT9, PYCR1, and STRADA; GCGR, BTN2A1, NAT9, PYCR1, and SVOPL; GCGR, BTN2A1, NAT9, PYCR1, and ZFYVE9; GCGR, BTN2A1, NAT9, PYCR1, and ZNF205; GCGR, BTN2A1, NAT9, RAD51AP1, and SEC61G; GCGR, BTN2A1, NAT9, RAD51AP1, and STRADA; GCGR, BTN2A1, NAT9, RAD51AP1, and SVOPL; GCGR, BTN2A1, NAT9, RAD51AP1, and ZFYVE9; GCGR, BTN2A1, NAT9, RAD51AP1, and ZNF205; GCGR, BTN2A1, NAT9, SEC61G, and STRADA; GCGR, BTN2A1, NAT9, SEC61G, and SVOPL; GCGR, BTN2A1, NAT9, SEC61G, and ZFYVE9; GCGR, BTN2A1, NAT9, SEC61G, and ZNF205; GCGR, BTN2A1, NAT9, STRADA, and SVOPL; GCGR, BTN2A1, NAT9, STRADA, and ZFYVE9; GCGR, BTN2A1, NAT9, STRADA, and ZNF205; GCGR, BTN2A1, NAT9, SVOPL, and ZFYVE9; GCGR, BTN2A1, NAT9, SVOPL, and ZNF205; GCGR, BTN2A1, NAT9, ZFYVE9, and ZNF205; GCGR, BTN2A1, NDUFA9, NEU2, and PLA2G1B; GCGR, BTN2A1, NDUFA9, NEU2, and PYCR1; GCGR, BTN2A1, NDUFA9, NEU2, and RAD51AP1; GCGR, BTN2A1, NDUFA9, NEU2, and SEC61G; GCGR, BTN2A1, NDUFA9, NEU2, and STRADA; GCGR, BTN2A1, NDUFA9, NEU2, and SVOPL; GCGR, BTN2A1, NDUFA9, NEU2, and ZFYVE9; GCGR, BTN2A1, NDUFA9, NEU2, and ZNF205; GCGR, BTN2A1, NDUFA9, PLA2G1B, and PYCR1; GCGR, BTN2A1, NDUFA9, PLA2G1B, and RAD51AP1; GCGR, BTN2A1, NDUFA9, PLA2G1B, and SEC61G; GCGR, BTN2A1, NDUFA9, PLA2G1B, and STRADA; GCGR, BTN2A1, NDUFA9, PLA2G1B, and SVOPL; GCGR, BTN2A1, NDUFA9, PLA2G1B, and ZFYVE9; GCGR, BTN2A1, NDUFA9, PLA2G1B, and ZNF205; GCGR, BTN2A1, NDUFA9, PYCR1, and RAD51AP1; GCGR, BTN2A1, NDUFA9, PYCR1, and SEC61G; GCGR, BTN2A1, NDUFA9, PYCR1, and STRADA; GCGR, BTN2A1, NDUFA9, PYCR1, and SVOPL; GCGR, BTN2A1, NDUFA9, PYCR1, and ZFYVE9; GCGR, BTN2A1, NDUFA9, PYCR1, and ZNF205; GCGR, BTN2A1, NDUFA9, RAD51AP1, and SEC61G; GCGR, BTN2A1, NDUFA9, RAD51AP1, and STRADA; GCGR, BTN2A1, NDUFA9, RAD51AP1, and SVOPL; GCGR, BTN2A1, NDUFA9, RAD51AP1, and ZFYVE9; GCGR, BTN2A1, NDUFA9, RAD51AP1, and ZNF205; GCGR, BTN2A1, NDUFA9, SEC61G, and STRADA; GCGR, BTN2A1, NDUFA9, SEC61G, and SVOPL; GCGR, BTN2A1, NDUFA9, SEC61G, and ZFYVE9; GCGR, BTN2A1, NDUFA9, SEC61G, and ZNF205; GCGR, BTN2A1, NDUFA9, STRADA, and SVOPL; GCGR, BTN2A1, NDUFA9, STRADA, and ZFYVE9; GCGR, BTN2A1, NDUFA9, STRADA, and ZNF205; GCGR, BTN2A1, NDUFA9, SVOPL, and ZFYVE9; GCGR, BTN2A1, NDUFA9, SVOPL, and ZNF205; GCGR, BTN2A1, NDUFA9, ZFYVE9, and ZNF205; GCGR, BTN2A1, NEU2, PLA2G1B, and PYCR1; GCGR, BTN2A1, NEU2, PLA2G1B, and RAD51AP1; GCGR, BTN2A1, NEU2, PLA2G1B, and SEC61G; GCGR, BTN2A1, NEU2, PLA2G1B, and STRADA; GCGR, BTN2A1, NEU2, PLA2G1B, and SVOPL; GCGR, BTN2A1, NEU2, PLA2G1B, and ZFYVE9; GCGR, BTN2A1, NEU2, PLA2G1B, and ZNF205; GCGR, BTN2A1, NEU2, PYCR1, and RAD51AP1; GCGR, BTN2A1, NEU2, PYCR1, and SEC61G; GCGR, BTN2A1, NEU2, PYCR1, and STRADA; GCGR, BTN2A1, NEU2, PYCR1, and SVOPL; GCGR, BTN2A1, NEU2, PYCR1, and ZFYVE9; GCGR, BTN2A1, NEU2, PYCR1, and ZNF205; GCGR, BTN2A1, NEU2, RAD51AP1, and SEC61G; GCGR, BTN2A1, NEU2, RAD51AP1, and STRADA; GCGR, BTN2A1, NEU2, RAD51AP1, and SVOPL; GCGR, BTN2A1, NEU2, RAD51AP1, and ZFYVE9; GCGR, BTN2A1, NEU2, RAD51AP1, and ZNF205; GCGR, BTN2A1, NEU2, SEC61G, and STRADA; GCGR, BTN2A1, NEU2, SEC61G, and SVOPL; GCGR, BTN2A1, NEU2, SEC61G, and ZFYVE9; GCGR, BTN2A1, NEU2, SEC61G, and ZNF205; GCGR, BTN2A1, NEU2, STRADA, and SVOPL; GCGR, BTN2A1, NEU2, STRADA, and ZFYVE9; GCGR, BTN2A1, NEU2, STRADA, and ZNF205; GCGR, BTN2A1, NEU2, SVOPL, and ZFYVE9; GCGR, BTN2A1, NEU2, SVOPL, and ZNF205; GCGR, BTN2A1, NEU2, ZFYVE9, and ZNF205; GCGR, BTN2A1, PLA2G1B, PYCR1, and RAD51AP1; GCGR, BTN2A1, PLA2G1B, PYCR1, and SEC61G; GCGR, BTN2A1, PLA2G1B, PYCR1, and STRADA; GCGR, BTN2A1, PLA2G1B, PYCR1, and SVOPL; GCGR, BTN2A1, PLA2G1B, PYCR1, and ZFYVE9; GCGR, BTN2A1, PLA2G1B, PYCR1, and ZNF205; GCGR, BTN2A1, PLA2G1B, RAD51AP1, and SEC61G; GCGR, BTN2A1, PLA2G1B, RAD51AP1, and STRADA; GCGR, BTN2A1, PLA2G1B, RAD51AP1, and SVOPL; GCGR, BTN2A1, PLA2G1B, RAD51AP1, and ZFYVE9; GCGR, BTN2A1, PLA2G1B, RAD51AP1, and ZNF205; GCGR, BTN2A1, PLA2G1B, SEC61G, and STRADA; GCGR, BTN2A1, PLA2G1B, SEC61G, and SVOPL; GCGR, BTN2A1, PLA2G1B, SEC61G, and ZFYVE9; GCGR, BTN2A1, PLA2G1B, SEC61G, and ZNF205; GCGR, BTN2A1, PLA2G1B, STRADA, and SVOPL; GCGR, BTN2A1, PLA2G1B, STRADA, and ZFYVE9; GCGR, BTN2A1, PLA2G1B, STRADA, and ZNF205; GCGR, BTN2A1, PLA2G1B, SVOPL, and ZFYVE9; GCGR, BTN2A1, PLA2G1B, SVOPL, and ZNF205; GCGR, BTN2A1, PLA2G1B, ZFYVE9, and ZNF205; GCGR, BTN2A1, PYCR1, RAD51AP1, and SEC61G; GCGR, BTN2A1, PYCR1, RAD51AP1, and STRADA; GCGR, BTN2A1, PYCR1, RAD51AP1, and SVOPL; GCGR, BTN2A1, PYCR1, RAD51AP1, and ZFYVE9; GCGR, BTN2A1, PYCR1, RAD51AP1, and ZNF205; GCGR, BTN2A1, PYCR1, SEC61G, and STRADA; GCGR, BTN2A1, PYCR1, SEC61G, and SVOPL; GCGR, BTN2A1, PYCR1, SEC61G, and ZFYVE9; GCGR, BTN2A1, PYCR1, SEC61G, and ZNF205; GCGR, BTN2A1, PYCR1, STRADA, and SVOPL; GCGR, BTN2A1, PYCR1, STRADA, and ZFYVE9; GCGR, BTN2A1, PYCR1, STRADA, and ZNF205; GCGR, BTN2A1, PYCR1, SVOPL, and ZFYVE9; GCGR, BTN2A1, PYCR1, SVOPL, and ZNF205; GCGR, BTN2A1, PYCR1, ZFYVE9, and ZNF205; GCGR, BTN2A1, RAD51AP1, SEC61G, and STRADA; GCGR, BTN2A1, RAD51AP1, SEC61G, and SVOPL; GCGR, BTN2A1, RAD51AP1, SEC61G, and ZFYVE9; GCGR, BTN2A1, RAD51AP1, SEC61G, and ZNF205; GCGR, BTN2A1, RAD51AP1, STRADA, and SVOPL; GCGR, BTN2A1, RAD51AP1, STRADA, and ZFYVE9; GCGR, BTN2A1, RAD51AP1, STRADA, and ZNF205; GCGR, BTN2A1, RAD51AP1, SVOPL, and ZFYVE9; GCGR, BTN2A1, RAD51AP1, SVOPL, and ZNF205; GCGR, BTN2A1, RAD51AP1, ZFYVE9, and ZNF205; GCGR, BTN2A1, SEC61G, STRADA, and SVOPL; GCGR, BTN2A1, SEC61G, STRADA, and ZFYVE9; GCGR, BTN2A1, SEC61G, STRADA, and ZNF205; GCGR, BTN2A1, SEC61G, SVOPL, and ZFYVE9; GCGR, BTN2A1, SEC61G, SVOPL, and ZNF205; GCGR, BTN2A1, SEC61G, ZFYVE9, and ZNF205; GCGR, BTN2A1, STRADA, SVOPL, and ZFYVE9; GCGR, BTN2A1, STRADA, SVOPL, and ZNF205; GCGR, BTN2A1, STRADA, ZFYVE9, and ZNF205; and GCGR, BTN2A1, SVOPL, ZFYVE9, and ZNF205. Any other combination of two or more of the disclosed genes BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 is specifically disclosed herein. For example, any combination of two or more of CNTD2, GCGR, PYCR1, RAD51AP1, ZFYVE9, and ZNF205; any combination of two or more of CNTD2, GCGR, NAT9, PYCR1, SVOPL, and ZNF205; any combination of two or more of BTN2A1, CNTD2, COQ9, EP300, GCGR, NDUFA9, PLA2G1B, RAD51AP1, SEC61G, STRADA, SVOPL, ZFYVE9, and ZNF205; any combination of two or more of BTN2A1, CNTD2, RAD51AP1, SEC61G, and SVOPL; any combination of two or more of BTN2A1, CNTD2, COQ9, EP300, GCGR, NAT9, SEC61G, and ZNF205; any combination of two or more of EMX2, EP300, FGF2, NAT9, PYCR1, SEC61G, SVOPL, and ZFYVE9; any combination of BTN2A1, CNTD2, COQ9, FGF2, GCGR, NAT9, NDUFA9, NEU2, PLA2G1B, RAD51AP1, SEC61G, STRADA, SVOPL, ZFYVE9, and ZNF205; any combination of two or more of COQ9, EMX2, EP300, FGF2, GCGR, NAT9, NDUFA9, RAD51AP1, SEC61G, STRADA, SVOPL, ZFYVE9, and ZNF205; and any combination of two or more of CNTD2, COQ9, EMX2, EP300, GCGR, NDUFA9, NEU2, PLA2G1B, PYCR1, SEC61G, SVOPL, ZFYVE9, and ZNF205.

As used herein, “increased viral production,” “increasing viral production,” “increased viral production,” and “increasing viral production,” refer to a change in viral titers resulting in more virus and/or more viral antigen being produced. In one aspect, it is understood that an increase in viral production includes an increase in live virus, viral antigen, and/or empty capsid as measured by any number of art-recognized techniques including plaque assays, TCID50 assays, ELISA, FFN, quantitative PCR, and more. Thus, the methods disclosed herein are understood to also increase viral antigen with or without a commensurate increase in viral production, but necessarily increase viral antigen production when viral production is increased.

The disclosed methods can be performed with any cell that can be infected with virus. In one aspect, the cells can be of mammalian origin (including, human, simian, porcine, bovine, equine, canine, feline, rodent (e.g., rabbit, rat, mouse, and guinea pig), and non-human primate) or avian including chicken, duck, ostrich, and turkey cells. It is further contemplated that the cell can be a cell of an established mammalian cell line including, but not limited to MA104 cells, VERO cells, Madin-Darby Canine Kidney (MDCK) cells, HEp-2 cells, HeLa cells, HEK293 cells, MRC-5 cells, WI-38 cells, EB66, and PER C6 cells. In one aspect, it is understood an herein contemplated that the cells with reduced BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 expression for use in the disclosed methods do not include any cell that naturally has reduced expression of any one or more of BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, but only includes cells where reduced expression is the result of human manipulation or genetic engineering (e.g., a recombinant cell line) to the specific cell or the cell line through any of the means for reducing gene expression disclosed herein or otherwise known in the art. In other words, reduced expression of BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 refers to a reduction in expression relative to an unmodified/unengineered cell line from which the modified cell line is derived. Accordingly, in one aspect, disclosed herein are engineered manipulated, engineered, and/or recombinant vero cells comprising reduced expression of any one or combination of two or more of BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205; more preferably, disclosed herein are manipulated, engineered, and/or recombinant vero cells comprising reduced expression of any one or combination of two or more of BTN2A1, CNTD2, EP300, GCGR, PYCR1, and/or ZNF205.

As noted above, the disclosed methods can work for any virus disclosed herein regardless of Baltimore classification group (e.g., double stranded DNA viruses, positive sense single stranded RNA viruses, and negative sense single stranded RNA virus), viral family within a Baltimore classification group (e.g., double stranded DNA virus families including, but not limited to, Herpesviridae; positive sense single stranded RNA viral families including, but not limited to, PicornaviridaeFlaviviridae, and Togaviridae; and negative sense single stranded RNA viral families including, but not limited to, orthomyxoviridae andparamyxoviridae), viral species within a viral family (e.g., Herpesviridae including, but not limited to varicella-zoster virus; Flaviviridae including, but not limited to, Dengue virus, Yellow fever virus, West Nile virus, Zika virus (including strains PRVABC59 and IbH30656), or St. Louis encephalitis virus; Togaviridae including, but not limited Rubella virus; Reoviridae including, but not limited to Rotavirus; Picornaviridae including, but not limited to Coxsackie virus, Poliovirus, and Hepatitis A virus; orthomyxoviridae including but not limited to Influenza A or Influenza B; and Paramyxoviridae including, but not limited to Mumps) and variants including, but not limited to viral reassortants.

Accordingly, in one aspect, disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, or ZNF205 wherein the virus is a double stranded DNA virus. Also disclosed are methods of increasing viral production wherein the double stranded DNA virus is a virus of the viral family herpesviridae, and wherein the virus is varicella-zoster virus. For example, disclosed herein are methods of increasing viral production comprising infecting a cell or cell line with a virus; wherein the virus is varicella-zoster virus; and wherein the cell or cell line comprises reduced expression of one or any combination of two or more cellular genes selected from the group comprising CNTD2, COQ9, EMX2, EP300, FGF2, GCGR, NAT9, NDUFA9, PYCR1, RAD51AP1, SEC61G, STRADA, SVOPL, or ZFYVE9; more preferably the cell comprises reduced expression of one or any combination of two or more cellular genes selected from the group comprising CNTD2, EMX2, EP300, FGF2, NAT9, PYCR1, SEC61G, SVOPL, or ZFYVE9.

Accordingly, in one aspect, disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, LRGUK, NAT9, NDUFA9, NEU2, PLA2G1B, PYCR1, RAD51AP1, SEC61G, STRADA, SVOPL, WDR62, ZFYVE9, or ZNF205 wherein the virus is a double stranded RNA virus. Also disclosed are methods of increasing viral production wherein the double stranded RNA virus is a virus of the viral family Reoviridae, and wherein the virus is rotavirus. For example, disclosed herein are methods of increasing viral production comprising infecting a cell or cell line with a virus; wherein the virus is rotavirus; and wherein the cell or cell line comprises reduced expression of one or any combination of two or more cellular genes selected from the group comprising BTN2A1, CNTD2, COQ9, EMX2, EP300, FGF2, GCGR, LRGUK, NAT9, NDUFA9, NEU2, PLA2G1B, PYCR1, RAD51AP1, SEC61G, STRADA, SVOPL, WDR62, ZFYVE9, or ZNF205; more preferably the cell comprises reduced expression of one or any combination of two or more cellular genes selected from the group comprising COQ9, NAT9, NDUFA9, NEU2, RAD51AP1, or SVOPL.

Also disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, or ZNF205 wherein the virus is a positive sense single stranded RNA virus. Also disclosed are methods of increasing viral production wherein the positive sense single stranded RNA virus is a virus of the viral family flaviviridae and wherein the virus is selected from the group of viruses comprising Dengue virus, Yellow fever virus, West Nile virus, Zika virus (including strains PRVABC59 and IbH30656), or St. Louis encephalitis virus. For example, disclosed herein are methods of increasing viral production comprising infecting a cell or cell line with a virus; wherein the virus is Dengue virus; and wherein the cell or cell line comprises reduced expression of one or any combination of two or more cellular genes selected from the group comprising BTN2A1, CNTD2, COQ9, FGF2, GCGR, NAT9, NDUFA9, NEU2, PLA2G1B, STRADA, SVOPL, ZFYVE9, or ZNF205; more preferably the cell comprises reduced expression of one or more cellular genes selected from the group comprising BTN2A1, CNTD2, COQ9, GCGR, STRADA, SVOPL, or ZFYVE9. Also for example, disclosed herein are methods of increasing viral production comprising infecting a cell or cell line with a virus; wherein the virus is Yellow Fever virus; and wherein the cell or cell line comprises reduced expression of one or any combination of two or more cellular genes selected from the group comprising BTN2A1, CNTD2, COQ9, EP300, GCGR, NDUFA9, PLA2G1B, PYCR1, RAD51AP1, STRADA, SVOPL, ZFYVE9, or ZNF205; more preferably the cell comprises reduced expression of one or more cellular genes selected from the group comprising BTN2A1, COQ9, EP300, GCGR, PLA2G1B, or RAD51AP1. Also for example, disclosed herein are methods of increasing viral production comprising infecting a cell or cell line with a virus; wherein the virus is West Nile virus; and wherein the cell or cell line comprises reduced expression of one or any combination of two or more cellular genes selected from the group comprising COQ9, EMX2, EP300, FGF2, GCGR, NAT9, NDUFA9, RAD51AP1, SEC61G, STRADA, SVOPL, ZFYVE9, or ZNF205. Also for example, disclosed herein are methods of increasing viral production comprising infecting a cell or cell line with a virus; wherein the virus is Zika virus (including strains PRVABC59 and IbH30656); and wherein the cell or cell line comprises reduced expression of one or any combination of two or more cellular genes selected from the group comprising BTN2A1, CNTD2, EP300, GCGR, NAT9, PYCR1, RAD51AP1, STRADA, ZFYVE9, or ZNF205; more preferably the cell comprises reduced expression of one or any combination of two or more cellular genes selected from the group comprising PYCR1, RAD51AP1, ZFYVE9, or ZNF205.

Also disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, or ZNF205 wherein the virus is a positive sense single stranded RNA virus of the viral family Togaviridae (for example, Rubella virus). For example, disclosed herein are methods of increasing viral production comprising infecting a cell or cell line with a virus; wherein the virus is Rubella virus; and wherein the cell or cell line comprises reduced expression of one or any combination of two or more cellular genes selected from the group comprising CNTD2, GCGR, NAT9, PLA2G1B, PYCR1, RAD51AP1, SVOPL, or ZNF205; more preferably the cell comprises reduced expression of one or any combination of two or more cellular genes selected from the group comprising CNTD2, GCGR, NAT9, PYCR1, SVOPL, or ZNF205.

Also disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, or ZNF205 wherein the virus is a positive sense single stranded RNA virus of the viral family Picornaviridae (for example, Hepatitis A virus, poliovirus, or Coxsackie virus). In one aspect, disclosed herein are methods for increasing viral production comprising infecting a cell or cell line with a virus; wherein the virus is from the viral family picornaviradae, and wherein the cellular gene is selected from the group comprising CNTD2, COQ9, EMX2, EP300, GCGR, NDUFA9, PLA2G1B, PYCR1, SEC61G, SVOPL, ZFYVE9, or ZNF205. For example, disclosed herein are methods of increasing viral production comprising infecting a cell or cell line with a virus; wherein the virus is a Coxsackie virus (such as, for example Coxsackie virus B5 also known as Enterovirus 71 (EV71)) and wherein the cell or cell line comprises reduced expression of one or any combination of two or more cellular genes selected from the group comprising BTN2A1, CNTD2, COQ9, EMX2, EP300, GCGR, NAT9, NDUFA9, PLA2G1B, PYCR1, SEC61G, STRADA, or ZNF205; more preferably the cell comprises reduced expression of one or any combination of two or more cellular genes selected from the group comprising CNTD2, EMX2, EP300, GCGR, NAT9, PLA2G1B, STRADA, or ZNF205. Also, for example, disclosed herein are methods of increasing viral production comprising infecting a cell or cell line with a virus; wherein the virus is Hepatitis A virus and wherein the cell or cell line comprises reduced expression of one or any combination of two or more cellular genes selected from the group comprising CNTD2, COQ9, EMX2, EP300, FGF2, FGFR, GCGR, NDUFA9, NEU2, PLA2G1B, PYCR1, SEC61G, SVOPL, ZFYVE9, or ZNF205; more preferably the cell comprises reduced expression of one or any combination of two or more cellular genes selected from the group comprising CNTD2, COQ9, GCGR, NDUFA9, NEU2, PYCR1, SEC61G, or ZNF205. Also, for example, disclosed herein are methods of increasing viral production comprising infecting a cell or cell line with a virus; wherein the virus is Poliovirus and wherein the cell or cell line comprises reduced expression of one or any combination of two or more cellular genes selected from the group comprising BTN2A1, CNTD2, COQ9, EMX2, EP300, GCGR, NAT9, NDUFA9, NEU2, PLA2G1B, PYCR1, SEC61G, STRADA, SVOPL, ZFYVE9, or ZNF205; more preferably the cell comprises reduced expression of one or any combination of two or more cellular genes selected from the group comprising BTN2A1, CNTD2, EP300, GCGR, SEC61G, or ZNF205.

Also disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, or ZNF205 wherein the virus is a negative sense single stranded RNA virus of the viral family paramyxoviridae (for example, Mumps virus). For example, disclosed herein are methods of increasing viral production comprising infecting a cell or cell line with a virus; wherein the virus is Mumps virus and wherein the cell or cell line comprises reduced expression of one or any combination of two or more cellular genes selected from the group comprising BTN2A1, CNTD2, PLA2G1B, PYCR1, RAD51AP1, SEC61G, or SVOPL; more preferably the cell comprises reduced expression of one or any combination of two or more cellular genes selected from BTN2A1 or SVOPL.

Also disclosed herein are methods of increasing viral production comprising infecting a cell or cell line with a virus; wherein the cell or cell line comprises reduced expression of one or any combination of two or more cellular genes selected from the group comprising BTN2A1, CNTD2, COQ9, EMX2, EP300, FGF2, FGFR, GCGR, LYKS, NAT9, NDUFA9, NEU2, PLA2G1B, PYCR1, RAD51AP1, SEC61G, STRADA, SVOPL, ZFYVE9, or ZNF205 wherein the virus is a negative sense single stranded RNA virus of the viral family orthomyxoviridae (for example, Influenza A virus and Influenza B virus). For example, disclosed herein are methods of increasing viral production comprising infecting a cell or cell line with a virus; wherein the virus is Influenza B virus and wherein the cell or cell line comprises reduced expression of one or any combination of two or more cellular genes selected from the group comprising BTN2A1, COQ9, EMX2, EP300, FGF2, FGFR, GCGR, NAT9, NDUFA9, PLA2G1B, PYCR1, SEC61G, ZFYVE9, or ZNF205. In one aspect, the one or any combination of two or more cellular genes can be selected from the group comprising BTN2A1, COQ9, EP300, FGF2, GCGR, NAT9, NDUFA9, PLA2G1B, or SEC61G. Also, for example, disclosed herein are methods of increasing viral production comprising infecting a cell or cell line with a virus; wherein the virus is Influenza A virus and wherein the cell or cell line comprises reduced expression of one or any combination of two or more cellular genes selected from the group comprising CNTD2, NDUFA9, NEU2, PLA2G1B, PYCR1, ZFYVE9, or ZNF205. In one aspect, the one or any combination of two or more cellular genes selected from the group comprising CNTD2, NDUFA9, PLA2G1B, PYCR1, ZFYVE9, or ZNF205.

It is further understood that the disclosed methods include superinfection (i.e., concurrent infection of multiple viral strains) of a single cell with one, two, three, four, five, six, seven, eight, nine, ten, or more species, strains, variants, reassortants, or serotypes of virus. Preferably, modulation of the gene(s) in the described list enhance the production of the RV3 vaccine strain of virus.

The methods disclosed herein utilize a reduction in expression of a gene or its encoded protein to increase viral production. As used herein "reduced" or "decreased" expression refers to a change in the transcription of a gene, translation of an mRNA, or the activity of a protein encoded by a gene that results in less of the gene, translated mRNA, encoded protein, or protein activity relative to a control. Reduction in expression can be at least a 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the gene expression, mRNA translation, protein expression, or protein activity relative to a control. For example, disclosed herein are methods of increasing virus production disclosed herein comprise infecting a cell with a virus; wherein the infected cell comprises at least 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the expression of at least one gene selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 genes relative to a control.

It is further understood that one way of referring to a reduction rather than the percentage reduction is as a percentage of the control expression or activity. For example, a cell with at least a 15% reduction in the expression of a particular gene relative to a control would also be a gene with expression that is less than or equal to 85% of the expression of the control. Accordingly, in one aspect are methods wherein the gene expression, mRNA expression, protein expression, or protein activity is less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% of a control. Thus, disclosed herein are methods of increasing virus production disclosed herein comprise infecting a cell with a virus; wherein the infected cell comprises less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% reduction of the expression of at least one gene, mRNA, protein, or protein activity selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 relative to a control. For example, disclosed herein are methods of increasing virus production disclosed herein comprise infecting a cell with a virus; wherein the infected cell comprises less than or equal to 85% reduction of the expression of at least one gene selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 relative to a control.

It is understood and herein contemplated that the reduced expression can be achieved by any means known in the art including techniques that manipulate genomic DNA, messenger and/or non-coding RNA and/or proteins including but not limited to endogenous or exognenous control elements (e.g., small interfering RNAs (siRNA), small hairpin RNAs (shRNA), small molecule inhibitor, and antisense oligonucleotide) and/or mutations are present in or directly target the coding region of the gene, mRNA, or protein or are present in or target a regulator region operably linked to the gene, mRNA, or protein. As such, the technologies or mechanisms that can be employed to modulate a gene of interest include but are not limited to 1) technologies and reagents that target genomic DNA to result in an edited genome (e.g., homologous recombination to introduce a mutation such as a deletion into a gene, zinc finger nucleases, meganucleases, transcription activator-like effectors (e.g., TALENs), triplexes, mediators of epigenetic modification, and CRISPR/cas9 and rAAV technologies), 2) technologies and reagents that target RNA (e.g. agents that act through the RNAi pathway, antisense technologies, ribozyme technologies), and 3) technologies that target proteins (e.g., small molecules, aptamers, peptides, auxin- or FKBP-mediated destabilizing domains, antibodies).

In one embodiment for targeting DNA, gene modulation is achieved using zinc finger nucleases (ZFNs). Synthetic ZFNs are composed of a custom designed zinc finger binding domain fused with e.g. a Fold DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. Meganucleases, triplexes, CRISPR, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous or exogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5 ‘ UTR, the open reading frame, the 3’ UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2) lipid-mediated delivery, 3) electroporation, or 4) vector/plasmid-based expression systems. An introduced RNA molecule may be referred to as an exogenous nucleotide sequence or polynucleotide.

Another gene targeting reagent that uses RNAi pathways includes exogenous small hairpin RNA, also referred to as shRNA. shRNAs delivered to cells via e.g., expression constructs (e.g., plasmids, lentiviruses) have the ability to provide long term gene knockdown in a constitutive or regulated manner, depending upon the type of promoter employed. In one preferred embodiment, the genome of a lentiviral particle is modified to include one or more shRNA expression cassettes that target a gene (or genes) of interest. Such lentiviruses can infect a cell intended for vaccine production, stably integrate their viral genome into the host genome, and express the shRNA(s) in a 1) constitutive, 2) regulated, or (in the case where multiple shRNA are being expressed) constitutive and regulated fashion. In this way, cell lines having enhanced virus production capabilities can be created. It is worth noting, that approaches that use siRNA or shRNA have the added benefit in that they can be designed to target individual variants of a single gene or multiple closely related gene family members. In this way, individual reagents can be used to modulate larger collections of targets having similar or redundant functions or sequence motifs. The skilled person will recognize that lentiviral constructs can also incorporate cloned DNA, or ORF expression constructs.

In another embodiment for modulating gene function, gene suppression can be achieved by large scale transfection of cells with miRNA mimics or miRNA inhibitors introduced into the cells.

In another embodiment, modulation takes place at the protein level. By example, knockdown of gene function at the protein level can be achieved by a number of means including but not limited to targeting the protein with a small molecule, a peptide, an aptamer, destabilizing domains, or other methods that can e.g., down-regulate the activity or enhance the rate of degradation of a gene product. In one preferred instance, a small molecule that binds e.g. an active site and inhibits the function of a target protein can be added to e.g., the cell culture media and thereby introduced into the cell. Alternatively, target protein function can be modulated by introducing e.g., a peptide into a cell that (for instance) prevents protein-protein interactions (see for instance, Shangary et. al., (2009) Annual Review of Pharmacology and Toxicology 49:223). Such peptides can be introduced into a cell by transfection or electroporation, or introduced via an expression construct. Alternatively, peptides can be introduced into cells by 1) adding (e.g., through conjugation) one or more moieties that facilitate cellular delivery, or 2) supercharging molecules to enhance self-delivery (Cronican, J. J. et al (2010) ACS Chem. Biol. 5(8):747-52). Techniques for expressing a peptide include, but are not limited to 1) fusion of the peptide to a scaffold, or 2) attachment of a signal sequence, to stabilize or direct the peptide to a position or compartment of interest, respectively.

It is understood and contemplated herein that some methods of increasing viral production can comprise administering siRNA, miRNA mimics, shRNA, or miRNA inhibitors to the media of a virus infected cell or cell line to produce a cell or cell line with decreased expression of a gene that inhibits viral production rather than starting the method with a cell or cell line so modified. In one aspect, disclosed herein are method of increasing viral production comprising infecting a cell or cell line with a virus and incubating the cell or cell line under conditions suitable for the production of the virus by the cells, wherein the medium comprises an RNA polynucleotide that inhibits expression of a coding region selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205. Also disclosed are method of increasing virus production wherein the RNA polynucleotide is an siRNA, miRNA mimics, shRNA, or miRNA inhibitor.

It is understood and herein contemplated that the timing of target gene modulation can vary. In some cases it is envisioned that gene modulation may occur prior to virus infection. For instance, if the gene target of choice locks the cell in a particular phase of the cell cycle that is highly productive for virus replication or RV antigen production, initiating gene modulation prior to viral infection may be beneficial. In other cases, it may be beneficial for virus infection/replication or antigen production to be initiated prior to modulating the target gene of interest. For instance, if a particular host gene modulation event is essential at the later stages of viral replication or antigen production, but deleterious at the early stages, the inventors envision that gene modulation would be initiated after infection. In cases where two or more gene modulation events are required for optimized virus or RV antigen production, some of the genes may be modified before viral infection while others are modified after viral infection. Regardless of the timing of gene modulation, multiple methods (including, for instance, applications of shRNA in conjunction with regulatable (e.g., Tet-sensitive promoter) can be employed to time the expression of gene modulation.

In one aspect, it is contemplated herein that any of the disclosed methods of increasing viral production disclosed herein can further comprise incubating the cells or cell line under conditions suitable for the production of the virus by the cells; and harvesting the virus produced by the cells.

In one aspect disclosed herein are methods of increasing virus production comprising infecting any cell or cell line disclosed herein with a virus. In another aspect disclosed are methods further comprising producing virus vaccine in which cells having one or more genes or gene products modulated, are employed.

The compositions disclosed herein and the compositions necessary to perform the disclosed methods can be made using any method known to those of skill in the art for that particular reagent or compound unless otherwise specifically noted.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 is disclosed and discussed and a number of modifications that can be made to a number of molecules including the BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 are discussed, specifically contemplated is each and every combination and permutation of BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Rather than trying to develop and manufacture new influenza vaccines seasonally, particularly to counteract the emergence of new virus strains, there is a need to create improved vaccine cell line technology for this virus and many others. Disclosed herein is a universal vaccine cell line can support growing a variety of viruses to provide protection against existing and newly emergent viral strains. Achieving this capability with new vaccine cell line technology transforms the approach to vaccinology, reduces vaccine production costs and helps with diagnostic discovery. This is particularly prudent when it comes to propagating different viral strains needed in a vaccine perhaps using Vero cells.

In one aspect the disclosed compositions can be cells or cell lines to be used in the disclosed methods of increasing viral production. In one aspect, disclosed herein are cells comprising reduced expression of at least one gene selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205.

As used herein, the term "gene" refers to a transcription unit and regulatory regions that are adjacent (e.g., located upstream and downstream), and operably linked, to the transcription unit. A transcription unit is a series of nucleotides that are transcribed into an RNA molecule. A transcription unit may include a coding region. A "coding region" is a nucleotide sequence that encodes an unprocessed preRNA (i.e., an RNA molecule that includes both exons and introns) that is subsequently processed to an mRNA. A transcription unit may encode a non-coding RNA. A non-coding RNA is an RNA molecule that is not translated into a protein. Examples of non-coding RNAs include microRNA. The boundaries of a transcription unit are generally determined by an initiation site at its 5' end and a transcription terminator at its 3' end. A "regulatory region" is a nucleotide sequence that regulates expression of a transcription unit to which it is operably linked. Nonlimiting examples of regulatory sequences include promoters, enhancers, transcription initiation sites, translation start sites, translation stop sites, transcription terminators, and poly(A) signals. A regulatory region located upstream of a transcription unit may be referred to as a 5' UTR, and a regulatory region located downstream of a transcription unit may be referred to as a 3 ' UTR. A regulatory region may be transcribed and be part of an unprocessed preRNA. The term "operably linked" refers to a juxtaposition of components such that they are in a relationship permitting them to function in their intended manner. It is understood and herein contemplated that wherein a particular gene is discussed herein, such as, for example BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205; also disclosed are any orthologs and variants of the disclosed gene for use in any composition or method disclosed herein.

It is recognized that any individual gene can be identified by any number of names and accession numbers. In many cases, genes in this document are identified by common gene names (e.g. dolichyldiphosphatase 1 (NAT9)) or accession numbers associated with the DNA sequence, mRNA sequence, or protein sequence (e.g., NM_015654). Furthermore, it is recognized that for any reported DNA, RNA, or protein sequence, multiple sequence variants, splice variants or isoforms can be included in the databases. As the siRNAs used in this study are designed to suppress the expression of all variants/isoforms of a given gene, the gene targets identified in this document are intended to comprise all such variants/isoforms/orthologs.

As disclosed herein, the disclosed cells or cell lines derived therefrom can comprise the reduced expression of any combination of one, two, three, four, five, six, seven, eight, nine, 10, 11, 12, 13, 14, 15, 16, 17, 18, or all 19 of the disclosed genes BTN2A1; CNTD2; COQ9; EMX2; EP300; FGF2, FGFR, GCGR; NAT9; NDUFA9; NEU2; PLA2G1B; PYCR1; RAD51AP1; SEC61G; STRADA; SVOPL; ZFYVE9; ZNF205. For example, the cell can comprise reduced expression of GCGR alone or in combination with any one, two, three, four, five, six, seven, eight, nine, ten, eleven, twelve, thirteen, fourteen, fifteen, sixteen, or seventeen other of the selected genes. Thus, in one aspect, disclosed herein are cells comprising reduced expression of BTN2A1; CNTD2; COQ9; EMX2; EP300; FGF2, GCGR; NAT9; NDUFA9; NEU2; PLA2G1B; PYCR1; RAD51AP1; SEC61G; STRADA; SVOPL; ZFYVE9; ZNF205; GCGR and BTN2A1; GCGR and CNTD2; GCGR and COQ9; GCGR and EMX2; GCGR and EP300; GCGR and FGF2; GCGR and NAT9; GCGR and NDUFA9; GCGR and NEU2; GCGR and PLA2G1B; GCGR and PYCR1; GCGR and RAD51AP1; GCGR and SEC61G; GCGR and STRADA; GCGR and SVOPL; GCGR and ZFYVE9; GCGR and ZNF205; GCGR, BTNA21, and CNTD2; GCGR, BTNA21, and COQ9; GCGR, BTNA21, and EMX2; GCGR, BTNA21, and EP300; GCGR, BTNA21, and FGF2; GCGR, BTNA21, and NAT9; GCGR, BTNA21, and NDUFA9; GCGR, BTNA21, and NEU2; GCGR, BTNA21, and PLA2G1B; GCGR, BTNA21, and PYCR1; GCGR, BTNA21, and RAD51AP1; GCGR, BTNA21, and SEC61G; GCGR, BTNA21, and STRADA; GCGR, BTNA21, and SVOPL; GCGR, BTNA21, and ZFYVE9; GCGR, BTNA21, and ZNF205; GCGR, CNTD2, and COQ9; GCGR, CNTD2, and EMX2; GCGR, CNTD2, and EP300; GCGR, CNTD2, and FGF2; GCGR, CNTD2, and NAT9; GCGR, CNTD2, and NDUFA9; GCGR, CNTD2, and NEU2; GCGR, CNTD2, and PLA2G1B; GCGR, CNTD2, and PYCR1; GCGR, CNTD2, and RAD51AP1; GCGR, CNTD2, and SEC61G; GCGR, CNTD2, and STRADA; GCGR, CNTD2, and SVOPL; GCGR, CNTD2, and ZFYVE9; GCGR, CNTD2, and ZNF205; GCGR, COQ9, and EMX2; GCGR, COQ9, and EP300; GCGR, COQ9, and FGF2; GCGR, COQ9, and NAT9; GCGR, COQ9, and NDUFA9; GCGR, COQ9, and NEU2; GCGR, COQ9, and PLA2G1B; GCGR, COQ9, and PYCR1; GCGR, COQ9, and RAD51AP1; GCGR, COQ9, and SEC61G; GCGR, COQ9, and STRADA; GCGR, COQ9, and SVOPL; GCGR, COQ9, and ZFYVE9; GCGR, COQ9, and ZNF205; GCGR, EMX2, and EP300; GCGR, EMX2, and FGF2; GCGR, EMX2, and NAT9; GCGR, EMX2, and NDUFA9; GCGR, EMX2, and NEU2; GCGR, EMX2, and PLA2G1B; GCGR, EMX2, and PYCR1; GCGR, EMX2, and RAD51AP1; GCGR, EMX2, and SEC61G; GCGR, EMX2, and STRADA; GCGR, EMX2, and SVOPL; GCGR, EMX2, and ZFYVE9; GCGR, EMX2, and ZNF205; GCGR, EP300, and FGF2; GCGR, EP300, and NAT9; GCGR, EP300, and NDUFA9; GCGR, EP300, and NEU2; GCGR, EP300, and PLA2G1B; GCGR, EP300, and PYCR1; GCGR, EP300, and RAD51AP1; GCGR, EP300, and SEC61G; GCGR, EP300, and STRADA; GCGR, EP300, and SVOPL; GCGR, EP300, and ZFYVE9; GCGR, EP300, and ZNF205; GCGR, FGF2, and NAT9; GCGR, FGF2, and NDUFA9; GCGR, FGF2, and NEU2; GCGR, FGF2, and PLA2G1B; GCGR, FGF2, and PYCR1; GCGR, FGF2, and RAD51AP1; GCGR, FGF2, and SEC61G; GCGR, FGF2, and STRADA; GCGR, FGF2, and SVOPL; GCGR, FGF2, and ZFYVE9; GCGR, FGF2, and ZNF205; GCGR, NAT9, and NDUFA9; GCGR, NAT9, and NEU2; GCGR, NAT9, and PLA2G1B; GCGR, NAT9, and PYCR1; GCGR, NAT9, and RAD51AP1; GCGR, NAT9, and SEC61G; GCGR, NAT9, and STRADA; GCGR, NAT9, and SVOPL; GCGR, NAT9, and ZFYVE9; GCGR, NAT9, and ZNF205; GCGR, NDUFA9, and NEU2; GCGR, NDUFA9, and PLA2G1B; GCGR, NDUFA9, and PYCR1; GCGR, NDUFA9, and RAD51AP1; GCGR, NDUFA9, and SEC61G; GCGR, NDUFA9, and STRADA; GCGR, NDUFA9, and SVOPL; GCGR, NDUFA9, and ZFYVE9; GCGR, NDUFA9, and ZNF205; GCGR, NEU2, and PLA2G1B; GCGR, NEU2, and PYCR1; GCGR, NEU2, and RAD51AP1; GCGR, NEU2, and SEC61G; GCGR, NEU2, and STRADA; GCGR, NEU2, and SVOPL; GCGR, NEU2, and ZFYVE9; GCGR, NEU2, and ZNF205; GCGR, PLA2G1B, and PYCR1; GCGR, PLA2G1B, and RAD51AP1; GCGR, PLA2G1B, and SEC61G; GCGR, PLA2G1B, and STRADA; GCGR, PLA2G1B, and SVOPL; GCGR, PLA2G1B, and ZFYVE9; GCGR, PLA2G1B, and ZNF205; GCGR, PYCR1, and RAD51AP1; GCGR, PYCR1, and SEC61G; GCGR, PYCR1, and STRADA; GCGR, PYCR1, and SVOPL; GCGR, PYCR1, and ZFYVE9; GCGR, PYCR1, and ZNF205; GCGR, RAD51AP1, and SEC61G; GCGR, RAD51AP1, and STRADA; GCGR, RAD51AP1, and SVOPL; GCGR, RAD51AP1, and ZFYVE9; GCGR, RAD51AP1, and ZNF205; GCGR, SEC61G, and STRADA; GCGR, SEC61G, and SVOPL; GCGR, SEC61G, and ZFYVE9; GCGR, SEC61G, and ZNF205; GCGR, STRADA, and SVOPL; GCGR, STRADA, and ZFYVE9; GCGR, STRADA, and ZNF205; GCGR, SVOPL, and ZFYVE9; GCGR, SVOPL, and ZNF205; GCGR, ZFYVE9, and ZNF205; GCGR, BTN2A1, CNTD2, and COQ9; GCGR, BTN2A1, CNTD2, and EMX2; GCGR, BTN2A1, CNTD2, and EP300; GCGR, BTN2A1, CNTD2, and FGF2; GCGR, BTN2A1, CNTD2, and NAT9; GCGR, BTN2A1, CNTD2, and NDUFA9; GCGR, BTN2A1, CNTD2, and NEU2; GCGR, BTN2A1, CNTD2, and PLA2G1B; GCGR, BTN2A1, CNTD2, and PYCR1; GCGR, BTN2A1, CNTD2, and RAD51AP1; GCGR, BTN2A1, CNTD2, and SEC61G; GCGR, BTN2A1, CNTD2, and STRADA; GCGR, BTN2A1, CNTD2, and SVOPL; GCGR, BTN2A1, CNTD2, and ZFYVE9; GCGR, BTN2A1, CNTD2, and ZNF205; GCGR, BTN2A1, COQ9, and EMX2; GCGR, BTN2A1, COQ9, and EP300; GCGR, BTN2A1, COQ9, and FGF2; GCGR, BTN2A1, COQ9, and NAT9; GCGR, BTN2A1, COQ9, and NDUFA9; GCGR, BTN2A1, COQ9, and NEU2; GCGR, BTN2A1, COQ9, and PLA2G1B; GCGR, BTN2A1, COQ9, and PYCR1; GCGR, BTN2A1, COQ9, and RAD51AP1; GCGR, BTN2A1, COQ9, and SEC61G; GCGR, BTN2A1, COQ9, and STRADA; GCGR, BTN2A1, COQ9, and SVOPL; GCGR, BTN2A1, COQ9, and ZFYVE9; GCGR, BTN2A1, COQ9, and ZNF205; GCGR, BTN2A1, EMX2, and EP300; GCGR, BTN2A1, EMX2, and FGF2; GCGR, BTN2A1, EMX2, and NAT9; GCGR, BTN2A1, EMX2, and NDUFA9; GCGR, BTN2A1, EMX2, and NEU2; GCGR, BTN2A1, EMX2, and PLA2G1B; GCGR, BTN2A1, EMX2, and PYCR1; GCGR, BTN2A1, EMX2, and RAD51AP1; GCGR, BTN2A1, EMX2, and SEC61G; GCGR, BTN2A1, EMX2, and STRADA; GCGR, BTN2A1, EMX2, and SVOPL; GCGR, BTN2A1, EMX2, and ZFYVE9; GCGR, BTN2A1, EMX2, and ZNF205; GCGR, BTN2A1, EP300, and FGF2; GCGR, BTN2A1, EP300, and NAT9; GCGR, BTN2A1, EP300, and NDUFA9; GCGR, BTN2A1, EP300, and NEU2; GCGR, BTN2A1, EP300, and PLA2G1B; GCGR, BTN2A1, EP300, and PYCR1; GCGR, BTN2A1, EP300, and RAD51AP1; GCGR, BTN2A1, EP300, and SEC61G; GCGR, BTN2A1, EP300, and STRADA; GCGR, BTN2A1, EP300, and SVOPL; GCGR, BTN2A1, EP300, and ZFYVE9; GCGR, BTN2A1, EP300, and ZNF205; GCGR, BTN2A1, FGF2, and NAT9; GCGR, BTN2A1, FGF2, and NDUFA9; GCGR, BTN2A1, FGF2, and NEU2; GCGR, BTN2A1, FGF2, and PLA2G1B; GCGR, BTN2A1, FGF2, and PYCR1; GCGR, BTN2A1, FGF2, and RAD51AP1; GCGR, BTN2A1, FGF2, and SEC61G; GCGR, BTN2A1, FGF2, and STRADA; GCGR, BTN2A1, FGF2, and SVOPL; GCGR, BTN2A1, FGF2, and ZFYVE9; GCGR, BTN2A1, FGF2, and ZNF205; GCGR, BTN2A1, NAT9, and NDUFA9; GCGR, BTN2A1, NAT9, and NEU2; GCGR, BTN2A1, NAT9, and PLA2G1B; GCGR, BTN2A1, NAT9, and PYCR1; GCGR, BTN2A1, NAT9, and RAD51AP1; GCGR, BTN2A1, NAT9, and SEC61G; GCGR, BTN2A1, NAT9, and STRADA; GCGR, BTN2A1, NAT9, and SVOPL; GCGR, BTN2A1, NAT9, and ZFYVE9; GCGR, BTN2A1, NAT9, and ZNF205; GCGR, BTN2A1, NDUFA9, and NEU2; GCGR, BTN2A1, NDUFA9, and PLA2G1B; GCGR, BTN2A1, NDUFA9, and PYCR1; GCGR, BTN2A1, NDUFA9, and RAD51AP1; GCGR, BTN2A1, NDUFA9, and SEC61G; GCGR, BTN2A1, NDUFA9, and STRADA; GCGR, BTN2A1, NDUFA9, and SVOPL; GCGR, BTN2A1, NDUFA9, and ZFYVE9; GCGR, BTN2A1, NDUFA9, and ZNF205; GCGR, BTN2A1, NEU2, and PLA2G1B; GCGR, BTN2A1, NEU2, and PYCR1; GCGR, BTN2A1, NEU2, and RAD51AP1; GCGR, BTN2A1, NEU2, and SEC61G; GCGR, BTN2A1, NEU2, and STRADA; GCGR, BTN2A1, NEU2, and SVOPL; GCGR, BTN2A1, NEU2, and ZFYVE9; GCGR, BTN2A1, NEU2, and ZNF205; GCGR, BTN2A1, PLA2G1B, and PYCR1; GCGR, BTN2A1, PLA2G1B, and RAD51AP1; GCGR, BTN2A1, PLA2G1B, and SEC61G; GCGR, BTN2A1, PLA2G1B, and STRADA; GCGR, BTN2A1, PLA2G1B, and SVOPL; GCGR, BTN2A1, PLA2G1B, and ZFYVE9; GCGR, BTN2A1, PLA2G1B, and ZNF205; GCGR, BTN2A1, PYCR1, and RAD51AP1; GCGR, BTN2A1, PYCR1, and SEC61G; GCGR, BTN2A1, PYCR1, and STRADA; GCGR, BTN2A1, PYCR1, and SVOPL; GCGR, BTN2A1, PYCR1, and ZFYVE9; GCGR, BTN2A1, PYCR1, and ZNF205; GCGR, BTN2A1, RAD51AP1, and SEC61G; GCGR, BTN2A1, RAD51AP1, and STRADA; GCGR, BTN2A1, RAD51AP1, and SVOPL; GCGR, BTN2A1, RAD51AP1, and ZFYVE9; GCGR, BTN2A1, RAD51AP1, and ZNF205; GCGR, BTN2A1, SEC61G, and STRADA; GCGR, BTN2A1, SEC61G, and SVOPL; GCGR, BTN2A1, SEC61G, and ZFYVE9; GCGR, BTN2A1, SEC61G, and ZNF205; GCGR, BTN2A1, STRADA, and SVOPL; GCGR, BTN2A1, STRADA, and ZFYVE9; GCGR, BTN2A1, STRADA, and ZNF205; GCGR, BTN2A1, SVOPL, and ZFYVE9; GCGR, BTN2A1, SVOPL, and ZNF205; GCGR, BTN2A1, ZFYVE9, and ZNF205; GCGR, CNTD2, COQ9, and EMX2; GCGR, CNTD2, COQ9, and EP300; GCGR, CNTD2, COQ9, and FGF2; GCGR, CNTD2, COQ9, and NAT9; GCGR, CNTD2, COQ9, and NDUFA9; GCGR, CNTD2, COQ9, and NEU2; GCGR, CNTD2, COQ9, and PLA2G1B; GCGR, CNTD2, COQ9, and PYCR1; GCGR, CNTD2, COQ9, and RAD51AP1; GCGR, CNTD2, COQ9, and SEC61G; GCGR, CNTD2, COQ9, and STRADA; GCGR, CNTD2, COQ9, and SVOPL; GCGR, CNTD2, COQ9, and ZFYVE9; GCGR, CNTD2, COQ9, and ZNF205; GCGR, CNTD2, EMX2, and EP300; GCGR, CNTD2, EMX2, and FGF2; GCGR, CNTD2, EMX2, and NAT9; GCGR, CNTD2, EMX2, and NDUFA9; GCGR, CNTD2, EMX2, and NEU2; GCGR, CNTD2, EMX2, and PLA2G1B; GCGR, CNTD2, EMX2, and PYCR1; GCGR, CNTD2, EMX2, and RAD51AP1; GCGR, CNTD2, EMX2, and SEC61G; GCGR, CNTD2, EMX2, and STRADA; GCGR, CNTD2, EMX2, and SVOPL; GCGR, CNTD2, EMX2, and ZFYVE9; GCGR, CNTD2, EMX2, and ZNF205; GCGR, CNTD2, EP300, and FGF2; GCGR, CNTD2, EP300, and NAT9; GCGR, CNTD2, EP300, and NDUFA9; GCGR, CNTD2, EP300, and NEU2; GCGR, CNTD2, EP300, and PLA2G1B; GCGR, CNTD2, EP300, and PYCR1; GCGR, CNTD2, EP300, and RAD51AP1; GCGR, CNTD2, EP300, and SEC61G; GCGR, CNTD2, EP300, and STRADA; GCGR, CNTD2, EP300, and SVOPL; GCGR, CNTD2, EP300, and ZFYVE9; GCGR, CNTD2, EP300, and ZNF205; GCGR, CNTD2, FGF2, and NAT9; GCGR, CNTD2, FGF2, and NDUFA9; GCGR, CNTD2, FGF2, and NEU2; GCGR, CNTD2, FGF2, and PLA2G1B; GCGR, CNTD2, FGF2, and PYCR1; GCGR, CNTD2, FGF2, and RAD51AP1; GCGR, CNTD2, FGF2, and SEC61G; GCGR, CNTD2, FGF2, and STRADA; GCGR, CNTD2, FGF2, and SVOPL; GCGR, CNTD2, FGF2, and ZFYVE9; GCGR, CNTD2, FGF2, and ZNF205; GCGR, CNTD2, NAT9, and NDUFA9; GCGR, CNTD2, NAT9, and NEU2; GCGR, CNTD2, NAT9, and PLA2G1B; GCGR, CNTD2, NAT9, and PYCR1; GCGR, CNTD2, NAT9, and RAD51AP1; GCGR, CNTD2, NAT9, and SEC61G; GCGR, CNTD2, NAT9, and STRADA; GCGR, CNTD2, NAT9, and SVOPL; GCGR, CNTD2, NAT9, and ZFYVE9; GCGR, CNTD2, NAT9, and ZNF205; GCGR, CNTD2, NDUFA9, and NEU2; GCGR, CNTD2, NDUFA9, and PLA2G1B; GCGR, CNTD2, NDUFA9, and PYCR1; GCGR, CNTD2, NDUFA9, and RAD51AP1; GCGR, CNTD2, NDUFA9, and SEC61G; GCGR, CNTD2, NDUFA9, and STRADA; GCGR, CNTD2, NDUFA9, and SVOPL; GCGR, CNTD2, NDUFA9, and ZFYVE9; GCGR, CNTD2, NDUFA9, and ZNF205; GCGR, CNTD2, NEU2, and PLA2G1B; GCGR, CNTD2, NEU2, and PYCR1; GCGR, CNTD2, NEU2, and RAD51AP1; GCGR, CNTD2, NEU2, and SEC61G; GCGR, CNTD2, NEU2, and STRADA; GCGR, CNTD2, NEU2, and SVOPL; GCGR, CNTD2, NEU2, and ZFYVE9; GCGR, CNTD2, NEU2, and ZNF205; GCGR, CNTD2, PLA2G1B, and PYCR1; GCGR, CNTD2, PLA2G1B, and RAD51AP1; GCGR, CNTD2, PLA2G1B, and SEC61G; GCGR, CNTD2, PLA2G1B, and STRADA; GCGR, CNTD2, PLA2G1B, and SVOPL; GCGR, CNTD2, PLA2G1B, and ZFYVE9; GCGR, CNTD2, PLA2G1B, and ZNF205; GCGR, CNTD2, PYCR1, and RAD51AP1; GCGR, CNTD2, PYCR1, and SEC61G; GCGR, CNTD2, PYCR1, and STRADA; GCGR, CNTD2, PYCR1, and SVOPL; GCGR, CNTD2, PYCR1, and ZFYVE9; GCGR, CNTD2, PYCR1, and ZNF205; GCGR, CNTD2, RAD51AP1, and SEC61G; GCGR, CNTD2, RAD51AP1, and STRADA; GCGR, CNTD2, RAD51AP1, and SVOPL; GCGR, CNTD2, RAD51AP1, and ZFYVE9; GCGR, CNTD2, RAD51AP1, and ZNF205; GCGR, CNTD2, SEC61G, and STRADA; GCGR, CNTD2, SEC61G, and SVOPL; GCGR, CNTD2, SEC61G, and ZFYVE9; GCGR, CNTD2, SEC61G, and ZNF205; GCGR, CNTD2, STRADA, and SVOPL; GCGR, CNTD2, STRADA, and ZFYVE9; GCGR, CNTD2, STRADA, and ZNF205; GCGR, CNTD2, SVOPL, and ZFYVE9; GCGR, CNTD2, SVOPL, and ZNF205; GCGR, CNTD2, ZFYVE9, and ZNF205; GCGR, COQ9, EMX2, and EP300; GCGR, COQ9, EMX2, and FGF2; GCGR, COQ9, EMX2, and NAT9; GCGR, COQ9, EMX2, and NDUFA9; GCGR, COQ9, EMX2, and NEU2; GCGR, COQ9, EMX2, and PLA2G1B; GCGR, COQ9, EMX2, and PYCR1; GCGR, COQ9, EMX2, and RAD51AP1; GCGR, COQ9, EMX2, and SEC61G; GCGR, COQ9, EMX2, and STRADA; GCGR, COQ9, EMX2, and SVOPL; GCGR, COQ9, EMX2, and ZFYVE9; GCGR, COQ9, EMX2, and ZNF205; GCGR, COQ9, EP300, and FGF2; GCGR, COQ9, EP300, and NAT9; GCGR, COQ9, EP300, and NDUFA9; GCGR, COQ9, EP300, and NEU2; GCGR, COQ9, EP300, and PLA2G1B; GCGR, COQ9, EP300, and PYCR1; GCGR, COQ9, EP300, and RAD51AP1; GCGR, COQ9, EP300, and SEC61G; GCGR, COQ9, EP300, and STRADA; GCGR, COQ9, EP300, and SVOPL; GCGR, COQ9, EP300, and ZFYVE9; GCGR, COQ9, EP300, and ZNF205; GCGR, COQ9, FGF2, and NAT9; GCGR, COQ9, FGF2, and NDUFA9; GCGR, COQ9, FGF2, and NEU2; GCGR, COQ9, FGF2, and PLA2G1B; GCGR, COQ9, FGF2, and PYCR1; GCGR, COQ9, FGF2, and RAD51AP1; GCGR, COQ9, FGF2, and SEC61G; GCGR, COQ9, FGF2, and STRADA; GCGR, COQ9, FGF2, and SVOPL; GCGR, COQ9, FGF2, and ZFYVE9; GCGR, COQ9, FGF2, and ZNF205; GCGR, COQ9, NAT9, and NDUFA9; GCGR, COQ9, NAT9, and NEU2; GCGR, COQ9, NAT9, and PLA2G1B; GCGR, COQ9, NAT9, and PYCR1; GCGR, COQ9, NAT9, and RAD51AP1; GCGR, COQ9, NAT9, and SEC61G; GCGR, COQ9, NAT9, and STRADA; GCGR, COQ9, NAT9, and SVOPL; GCGR, COQ9, NAT9, and ZFYVE9; GCGR, COQ9, NAT9, and ZNF205; GCGR, COQ9, NDUFA9, and NEU2; GCGR, COQ9, NDUFA9, and PLA2G1B; GCGR, COQ9, NDUFA9, and PYCR1; GCGR, COQ9, NDUFA9, and RAD51AP1; GCGR, COQ9, NDUFA9, and SEC61G; GCGR, COQ9, NDUFA9, and STRADA; GCGR, COQ9, NDUFA9, and SVOPL; GCGR, COQ9, NDUFA9, and ZFYVE9; GCGR, COQ9, NDUFA9, and ZNF205; GCGR, COQ9, NEU2, and PLA2G1B; GCGR, COQ9, NEU2, and PYCR1; GCGR, COQ9, NEU2, and RAD51AP1; GCGR, COQ9, NEU2, and SEC61G; GCGR, COQ9, NEU2, and STRADA; GCGR, COQ9, NEU2, and SVOPL; GCGR, COQ9, NEU2, and ZFYVE9; GCGR, COQ9, NEU2, and ZNF205; GCGR, COQ9, PLA2G1B, and PYCR1; GCGR, COQ9, PLA2G1B, and RAD51AP1; GCGR, COQ9, PLA2G1B, and SEC61G; GCGR, COQ9, PLA2G1B, and STRADA; GCGR, COQ9, PLA2G1B, and SVOPL; GCGR, COQ9, PLA2G1B, and ZFYVE9; GCGR, COQ9, PLA2G1B, and ZNF205; GCGR, COQ9, PYCR1, and RAD51AP1; GCGR, COQ9, PYCR1, and SEC61G; GCGR, COQ9, PYCR1, and STRADA; GCGR, COQ9, PYCR1, and SVOPL; GCGR, COQ9, PYCR1, and ZFYVE9; GCGR, COQ9, PYCR1, and ZNF205; GCGR, COQ9, RAD51AP1, and SEC61G; GCGR, COQ9, RAD51AP1, and STRADA; GCGR, COQ9, RAD51AP1, and SVOPL; GCGR, COQ9, RAD51AP1, and ZFYVE9; GCGR, COQ9, RAD51AP1, and ZNF205; GCGR, COQ9, SEC61G, and STRADA; GCGR, COQ9, SEC61G, and SVOPL; GCGR, COQ9, SEC61G, and ZFYVE9; GCGR, COQ9, SEC61G, and ZNF205; GCGR, COQ9, STRADA, and SVOPL; GCGR, COQ9, STRADA, and ZFYVE9; GCGR, COQ9, STRADA, and ZNF205; GCGR, COQ9, SVOPL, and ZFYVE9; GCGR, COQ9, SVOPL, and ZNF205; GCGR, COQ9, ZFYVE9, and ZNF205; GCGR, EMX2, EP300, and FGF2; GCGR, EMX2, EP300, and NAT9; GCGR, EMX2, EP300, and NDUFA9; GCGR, EMX2, EP300, and NEU2; GCGR, EMX2, EP300, and PLA2G1B; GCGR, EMX2, EP300, and PYCR1; GCGR, EMX2, EP300, and RAD51AP1; GCGR, EMX2, EP300, and SEC61G; GCGR, EMX2, EP300, and STRADA; GCGR, EMX2, EP300, and SVOPL; GCGR, EMX2, EP300, and ZFYVE9; GCGR, EMX2, EP300, and ZNF205; GCGR, EMX2, FGF2, and NAT9; GCGR, EMX2, FGF2, and NDUFA9; GCGR, EMX2, FGF2, and NEU2; GCGR, EMX2, FGF2, and PLA2G1B; GCGR, EMX2, FGF2, and PYCR1; GCGR, EMX2, FGF2, and RAD51AP1; GCGR, EMX2, FGF2, and SEC61G; GCGR, EMX2, FGF2, and STRADA; GCGR, EMX2, FGF2, and SVOPL; GCGR, EMX2, FGF2, and ZFYVE9; GCGR, EMX2, FGF2, and ZNF205; GCGR, EMX2, NAT9, and NDUFA9; GCGR, EMX2, NAT9, and NEU2; GCGR, EMX2, NAT9, and PLA2G1B; GCGR, EMX2, NAT9, and PYCR1; GCGR, EMX2, NAT9, and RAD51AP1; GCGR, EMX2, NAT9, and SEC61G; GCGR, EMX2, NAT9, and STRADA; GCGR, EMX2, NAT9, and SVOPL; GCGR, EMX2, NAT9, and ZFYVE9; GCGR, EMX2, NAT9, and ZNF205; GCGR, EMX2, NDUFA9, and NEU2; GCGR, EMX2, NDUFA9, and PLA2G1B; GCGR, EMX2, NDUFA9, and PYCR1; GCGR, EMX2, NDUFA9, and RAD51AP1; GCGR, EMX2, NDUFA9, and SEC61G; GCGR, EMX2, NDUFA9, and STRADA; GCGR, EMX2, NDUFA9, and SVOPL; GCGR, EMX2, NDUFA9, and ZFYVE9; GCGR, EMX2, NDUFA9, and ZNF205; GCGR, EMX2, NEU2, and PLA2G1B; GCGR, EMX2, NEU2, and PYCR1; GCGR, EMX2, NEU2, and RAD51AP1; GCGR, EMX2, NEU2, and SEC61G; GCGR, EMX2, NEU2, and STRADA; GCGR, EMX2, NEU2, and SVOPL; GCGR, EMX2, NEU2, and ZFYVE9; GCGR, EMX2, NEU2, and ZNF205; GCGR, EMX2, PLA2G1B, and PYCR1; GCGR, EMX2, PLA2G1B, and RAD51AP1; GCGR, EMX2, PLA2G1B, and SEC61G; GCGR, EMX2, PLA2G1B, and STRADA; GCGR, EMX2, PLA2G1B, and SVOPL; GCGR, EMX2, PLA2G1B, and ZFYVE9; GCGR, EMX2, PLA2G1B, and ZNF205; GCGR, EMX2, PYCR1, and RAD51AP1; GCGR, EMX2, PYCR1, and SEC61G; GCGR, EMX2, PYCR1, and STRADA; GCGR, EMX2, PYCR1, and SVOPL; GCGR, EMX2, PYCR1, and ZFYVE9; GCGR, EMX2, PYCR1, and ZNF205; GCGR, EMX2, RAD51AP1, and SEC61G; GCGR, EMX2, RAD51AP1, and STRADA; GCGR, EMX2, RAD51AP1, and SVOPL; GCGR, EMX2, RAD51AP1, and ZFYVE9; GCGR, EMX2, RAD51AP1, and ZNF205; GCGR, EMX2, SEC61G, and STRADA; GCGR, EMX2, SEC61G, and SVOPL; GCGR, EMX2, SEC61G, and ZFYVE9; GCGR, EMX2, SEC61G, and ZNF205; GCGR, EMX2, STRADA, and SVOPL; GCGR, EMX2, STRADA, and ZFYVE9; GCGR, EMX2, STRADA, and ZNF205; GCGR, EMX2, SVOPL, and ZFYVE9; GCGR, EMX2, SVOPL, and ZNF205; GCGR, EMX2, ZFYVE9, and ZNF205; GCGR, EP300, FGF2, and NAT9; GCGR, EP300, FGF2, and NDUFA9; GCGR, EP300, FGF2, and NEU2; GCGR, EP300, FGF2, and PLA2G1B; GCGR, EP300, FGF2, and PYCR1; GCGR, EP300, FGF2, and RAD51AP1; GCGR, EP300, FGF2, and SEC61G; GCGR, EP300, FGF2, and STRADA; GCGR, EP300, FGF2, and SVOPL; GCGR, EP300, FGF2, and ZFYVE9; GCGR, EP300, FGF2, and ZNF205; GCGR, EP300, NAT9, and NDUFA9; GCGR, EP300, NAT9, and NEU2; GCGR, EP300, NAT9, and PLA2G1B; GCGR, EP300, NAT9, and PYCR1; GCGR, EP300, NAT9, and RAD51AP1; GCGR, EP300, NAT9, and SEC61G; GCGR, EP300, NAT9, and STRADA; GCGR, EP300, NAT9, and SVOPL; GCGR, EP300, NAT9, and ZFYVE9; GCGR, EP300, NAT9, and ZNF205; GCGR, EP300, NDUFA9, and NEU2; GCGR, EP300, NDUFA9, and PLA2G1B; GCGR, EP300, NDUFA9, and PYCR1; GCGR, EP300, NDUFA9, and RAD51AP1; GCGR, EP300, NDUFA9, and SEC61G; GCGR, EP300, NDUFA9, and STRADA; GCGR, EP300, NDUFA9, and SVOPL; GCGR, EP300, NDUFA9, and ZFYVE9; GCGR, EP300, NDUFA9, and ZNF205; GCGR, EP300, NEU2, and PLA2G1B; GCGR, EP300, NEU2, and PYCR1; GCGR, EP300, NEU2, and RAD51AP1; GCGR, EP300, NEU2, and SEC61G; GCGR, EP300, NEU2, and STRADA; GCGR, EP300, NEU2, and SVOPL; GCGR, EP300, NEU2, and ZFYVE9; GCGR, EP300, NEU2, and ZNF205; GCGR, EP300, PLA2G1B, and PYCR1; GCGR, EP300, PLA2G1B, and RAD51AP1; GCGR, EP300, PLA2G1B, and SEC61G; GCGR, EP300, PLA2G1B, and STRADA; GCGR, EP300, PLA2G1B, and SVOPL; GCGR, EP300, PLA2G1B, and ZFYVE9; GCGR, EP300, PLA2G1B, and ZNF205; GCGR, EP300, PYCR1, and RAD51AP1; GCGR, EP300, PYCR1, and SEC61G; GCGR, EP300, PYCR1, and STRADA; GCGR, EP300, PYCR1, and SVOPL; GCGR, EP300, PYCR1, and ZFYVE9; GCGR, EP300, PYCR1, and ZNF205; GCGR, EP300, RAD51AP1, and SEC61G; GCGR, EP300, RAD51AP1, and STRADA; GCGR, EP300, RAD51AP1, and SVOPL; GCGR, EP300, RAD51AP1, and ZFYVE9; GCGR, EP300, RAD51AP1, and ZNF205; GCGR, EP300, SEC61G, and STRADA; GCGR, EP300, SEC61G, and SVOPL; GCGR, EP300, SEC61G, and ZFYVE9; GCGR, EP300, SEC61G, and ZNF205; GCGR, EP300, STRADA, and SVOPL; GCGR, EP300, STRADA, and ZFYVE9; GCGR, EP300, STRADA, and ZNF205; GCGR, EP300, SVOPL, and ZFYVE9; GCGR, EP300, SVOPL, and ZNF205; GCGR, EP300, ZFYVE9, and ZNF205; GCGR, FGF2, NAT9, and NDUFA9; GCGR, FGF2, NAT9, and NEU2; GCGR, FGF2, NAT9, and PLA2G1B; GCGR, FGF2, NAT9, and PYCR1; GCGR, FGF2, NAT9, and RAD51AP1; GCGR, FGF2, NAT9, and SEC61G; GCGR, FGF2, NAT9, and STRADA; GCGR, FGF2, NAT9, and SVOPL; GCGR, FGF2, NAT9, and ZFYVE9; GCGR, FGF2, NAT9, and ZNF205; GCGR, FGF2, NDUFA9, and NEU2; GCGR, FGF2, NDUFA9, and PLA2G1B; GCGR, FGF2, NDUFA9, and PYCR1; GCGR, FGF2, NDUFA9, and RAD51AP1; GCGR, FGF2, NDUFA9, and SEC61G; GCGR, FGF2, NDUFA9, and STRADA; GCGR, FGF2, NDUFA9, and SVOPL; GCGR, FGF2, NDUFA9, and ZFYVE9; GCGR, FGF2, NDUFA9, and ZNF205; GCGR, FGF2, NEU2, and PLA2G1B; GCGR, FGF2, NEU2, and PYCR1; GCGR, FGF2, NEU2, and RAD51AP1; GCGR, FGF2, NEU2, and SEC61G; GCGR, FGF2, NEU2, and STRADA; GCGR, FGF2, NEU2, and SVOPL; GCGR, FGF2, NEU2, and ZFYVE9; GCGR, FGF2, NEU2, and ZNF205; GCGR, FGF2, PLA2G1B, and PYCR1; GCGR, FGF2, PLA2G1B, and RAD51AP1; GCGR, FGF2, PLA2G1B, and SEC61G; GCGR, FGF2, PLA2G1B, and STRADA; GCGR, FGF2, PLA2G1B, and SVOPL; GCGR, FGF2, PLA2G1B, and ZFYVE9; GCGR, FGF2, PLA2G1B, and ZNF205; GCGR, FGF2, PYCR1, and RAD51AP1; GCGR, FGF2, PYCR1, and SEC61G; GCGR, FGF2, PYCR1, and STRADA; GCGR, FGF2, PYCR1, and SVOPL; GCGR, FGF2, PYCR1, and ZFYVE9; GCGR, FGF2, PYCR1, and ZNF205; GCGR, FGF2, RAD51AP1, and SEC61G; GCGR, FGF2, RAD51AP1, and STRADA; GCGR, FGF2, RAD51AP1, and SVOPL; GCGR, FGF2, RAD51AP1, and ZFYVE9; GCGR, FGF2, RAD51AP1, and ZNF205; GCGR, FGF2, SEC61G, and STRADA; GCGR, FGF2, SEC61G, and SVOPL; GCGR, FGF2, SEC61G, and ZFYVE9; GCGR, FGF2, SEC61G, and ZNF205; GCGR, FGF2, STRADA, and SVOPL; GCGR, FGF2, STRADA, and ZFYVE9; GCGR, FGF2, STRADA, and ZNF205; GCGR, FGF2, SVOPL, and ZFYVE9; GCGR, FGF2, SVOPL, and ZNF205; GCGR, FGF2, ZFYVE9, and ZNF205; GCGR, NAT9, NDUFA9, and NEU2; GCGR, NAT9, NDUFA9, and PLA2G1B; GCGR, NAT9, NDUFA9, and PYCR1; GCGR, NAT9, NDUFA9, and RAD51AP1; GCGR, NAT9, NDUFA9, and SEC61G; GCGR, NAT9, NDUFA9, and STRADA; GCGR, NAT9, NDUFA9, and SVOPL; GCGR, NAT9, NDUFA9, and ZFYVE9; GCGR, NAT9, NDUFA9, and ZNF205; GCGR, NAT9, NEU2, and PLA2G1B; GCGR, NAT9, NEU2, and PYCR1; GCGR, NAT9, NEU2, and RAD51AP1; GCGR, NAT9, NEU2, and SEC61G; GCGR, NAT9, NEU2, and STRADA; GCGR, NAT9, NEU2, and SVOPL; GCGR, NAT9, NEU2, and ZFYVE9; GCGR, NAT9, NEU2, and ZNF205; GCGR, NAT9, PLA2G1B, and PYCR1; GCGR, NAT9, PLA2G1B, and RAD51AP1; GCGR, NAT9, PLA2G1B, and SEC61G; GCGR, NAT9, PLA2G1B, and STRADA; GCGR, NAT9, PLA2G1B, and SVOPL; GCGR, NAT9, PLA2G1B, and ZFYVE9; GCGR, NAT9, PLA2G1B, and ZNF205; GCGR, NAT9, PYCR1, and RAD51AP1; GCGR, NAT9, PYCR1, and SEC61G; GCGR, NAT9, PYCR1, and STRADA; GCGR, NAT9, PYCR1, and SVOPL; GCGR, NAT9, PYCR1, and ZFYVE9; GCGR, NAT9, PYCR1, and ZNF205; GCGR, NAT9, RAD51AP1, and SEC61G; GCGR, NAT9, RAD51AP1, and STRADA; GCGR, NAT9, RAD51AP1, and SVOPL; GCGR, NAT9, RAD51AP1, and ZFYVE9; GCGR, NAT9, RAD51AP1, and ZNF205; GCGR, NAT9, SEC61G, and STRADA; GCGR, NAT9, SEC61G, and SVOPL; GCGR, NAT9, SEC61G, and ZFYVE9; GCGR, NAT9, SEC61G, and ZNF205; GCGR, NAT9, STRADA, and SVOPL; GCGR, NAT9, STRADA, and ZFYVE9; GCGR, NAT9, STRADA, and ZNF205; GCGR, NAT9, SVOPL, and ZFYVE9; GCGR, NAT9, SVOPL, and ZNF205; GCGR, NAT9, ZFYVE9, and ZNF205; GCGR, NDUFA9, NEU2, and PLA2G1B; GCGR, NDUFA9, NEU2, and PYCR1; GCGR, NDUFA9, NEU2, and RAD51AP1; GCGR, NDUFA9, NEU2, and SEC61G; GCGR, NDUFA9, NEU2, and STRADA; GCGR, NDUFA9, NEU2, and SVOPL; GCGR, NDUFA9, NEU2, and ZFYVE9; GCGR, NDUFA9, NEU2, and ZNF205; GCGR, NDUFA9, PLA2G1B, and PYCR1; GCGR, NDUFA9, PLA2G1B, and RAD51AP1; GCGR, NDUFA9, PLA2G1B, and SEC61G; GCGR, NDUFA9, PLA2G1B, and STRADA; GCGR, NDUFA9, PLA2G1B, and SVOPL; GCGR, NDUFA9, PLA2G1B, and ZFYVE9; GCGR, NDUFA9, PLA2G1B, and ZNF205; GCGR, NDUFA9, PYCR1, and RAD51AP1; GCGR, NDUFA9, PYCR1, and SEC61G; GCGR, NDUFA9, PYCR1, and STRADA; GCGR, NDUFA9, PYCR1, and SVOPL; GCGR, NDUFA9, PYCR1, and ZFYVE9; GCGR, NDUFA9, PYCR1, and ZNF205; GCGR, NDUFA9, RAD51AP1, and SEC61G; GCGR, NDUFA9, RAD51AP1, and STRADA; GCGR, NDUFA9, RAD51AP1, and SVOPL; GCGR, NDUFA9, RAD51AP1, and ZFYVE9; GCGR, NDUFA9, RAD51AP1, and ZNF205; GCGR, NDUFA9, SEC61G, and STRADA; GCGR, NDUFA9, SEC61G, and SVOPL; GCGR, NDUFA9, SEC61G, and ZFYVE9; GCGR, NDUFA9, SEC61G, and ZNF205; GCGR, NDUFA9, STRADA, and SVOPL; GCGR, NDUFA9, STRADA, and ZFYVE9; GCGR, NDUFA9, STRADA, and ZNF205; GCGR, NDUFA9, SVOPL, and ZFYVE9; GCGR, NDUFA9, SVOPL, and ZNF205; GCGR, NDUFA9, ZFYVE9, and ZNF205; GCGR, NEU2, PLA2G1B, and PYCR1; GCGR, NEU2, PLA2G1B, and RAD51AP1; GCGR, NEU2, PLA2G1B, and SEC61G; GCGR, NEU2, PLA2G1B, and STRADA; GCGR, NEU2, PLA2G1B, and SVOPL; GCGR, NEU2, PLA2G1B, and ZFYVE9; GCGR, NEU2, PLA2G1B, and ZNF205; GCGR, NEU2, PYCR1, and RAD51AP1; GCGR, NEU2, PYCR1, and SEC61G; GCGR, NEU2, PYCR1, and STRADA; GCGR, NEU2, PYCR1, and SVOPL; GCGR, NEU2, PYCR1, and ZFYVE9; GCGR, NEU2, PYCR1, and ZNF205; GCGR, NEU2, RAD51AP1, and SEC61G; GCGR, NEU2, RAD51AP1, and STRADA; GCGR, NEU2, RAD51AP1, and SVOPL; GCGR, NEU2, RAD51AP1, and ZFYVE9; GCGR, NEU2, RAD51AP1, and ZNF205; GCGR, NEU2, SEC61G, and STRADA; GCGR, NEU2, SEC61G, and SVOPL; GCGR, NEU2, SEC61G, and ZFYVE9; GCGR, NEU2, SEC61G, and ZNF205; GCGR, NEU2, STRADA, and SVOPL; GCGR, NEU2, STRADA, and ZFYVE9; GCGR, NEU2, STRADA, and ZNF205; GCGR, NEU2, SVOPL, and ZFYVE9; GCGR, NEU2, SVOPL, and ZNF205; GCGR, NEU2, ZFYVE9, and ZNF205; GCGR, PLA2G1B, PYCR1, and RAD51AP1; GCGR, PLA2G1B, PYCR1, and SEC61G; GCGR, PLA2G1B, PYCR1, and STRADA; GCGR, PLA2G1B, PYCR1, and SVOPL; GCGR, PLA2G1B, PYCR1, and ZFYVE9; GCGR, PLA2G1B, PYCR1, and ZNF205; GCGR, PLA2G1B, RAD51AP1, and SEC61G; GCGR, PLA2G1B, RAD51AP1, and STRADA; GCGR, PLA2G1B, RAD51AP1, and SVOPL; GCGR, PLA2G1B, RAD51AP1, and ZFYVE9; GCGR, PLA2G1B, RAD51AP1, and ZNF205; GCGR, PLA2G1B, SEC61G, and STRADA; GCGR, PLA2G1B, SEC61G, and SVOPL; GCGR, PLA2G1B, SEC61G, and ZFYVE9; GCGR, PLA2G1B, SEC61G, and ZNF205; GCGR, PLA2G1B, STRADA, and SVOPL; GCGR, PLA2G1B, STRADA, and ZFYVE9; GCGR, PLA2G1B, STRADA, and ZNF205; GCGR, PLA2G1B, SVOPL, and ZFYVE9; GCGR, PLA2G1B, SVOPL, and ZNF205; GCGR, PLA2G1B, ZFYVE9, and ZNF205; GCGR, PYCR1, RAD51AP1, and SEC61G; GCGR, PYCR1, RAD51AP1, and STRADA;

GCGR, PYCR1, RAD51AP1, and SVOPL; GCGR, PYCR1, RAD51AP1, and ZFYVE9; GCGR, PYCR1, RAD51AP1, and ZNF205; GCGR, PYCR1, SEC61G, and STRADA; GCGR, PYCR1, SEC61G, and SVOPL; GCGR, PYCR1, SEC61G, and ZFYVE9; GCGR, PYCR1, SEC61G, and ZNF205; GCGR, PYCR1, STRADA, and SVOPL; GCGR, PYCR1, STRADA, and ZFYVE9; GCGR, PYCR1, STRADA, and ZNF205; GCGR, PYCR1, SVOPL, and ZFYVE9; GCGR, PYCR1, SVOPL, and ZNF205; GCGR, PYCR1, ZFYVE9, and ZNF205; GCGR, RAD51AP1, SEC61G, and STRADA; GCGR, RAD51AP1, SEC61G, and SVOPL; GCGR, RAD51AP1, SEC61G, and ZFYVE9; GCGR, RAD51AP1, SEC61G, and ZNF205; GCGR, RAD51AP1, STRADA, and SVOPL; GCGR, RAD51AP1, STRADA, and ZFYVE9; GCGR, RAD51AP1, STRADA, and ZNF205; GCGR, RAD51AP1, SVOPL, and ZFYVE9; GCGR, RAD51AP1, SVOPL, and ZNF205; GCGR, RAD51AP1, ZFYVE9, and ZNF205; GCGR, SEC61G, STRADA, and SVOPL; GCGR, SEC61G, STRADA, and ZFYVE9; GCGR, SEC61G, STRADA, and ZNF205; GCGR, SEC61G, SVOPL, and ZFYVE9; GCGR, SEC61G, SVOPL, and ZNF205; GCGR, SEC61G, ZFYVE9, and ZNF205; GCGR, STRADA, SVOPL, and ZFYVE9; GCGR, STRADA, SVOPL, and ZNF205; GCGR, STRADA, ZFYVE9, and ZNF205; GCGR, SVOPL, ZFYVE9, and ZNF205; GCGR, BTN2A1, CNTD2, COQ9, and EMX2; GCGR, BTN2A1, CNTD2, COQ9, and EP300; GCGR, BTN2A1, CNTD2, COQ9, and FGF2; GCGR, BTN2A1, CNTD2, COQ9, and NAT9; GCGR, BTN2A1, CNTD2, COQ9, and NDUFA9; GCGR, BTN2A1, CNTD2, COQ9, and NEU2; GCGR, BTN2A1, CNTD2, COQ9, and PLA2G1B; GCGR, BTN2A1, CNTD2, COQ9, and PYCR1; GCGR, BTN2A1, CNTD2, COQ9, and RAD51AP1; GCGR, BTN2A1, CNTD2, COQ9, and SEC61G; GCGR, BTN2A1, CNTD2, COQ9, and STRADA; GCGR, BTN2A1, CNTD2, COQ9, and SVOPL; GCGR, BTN2A1, CNTD2, COQ9, and ZFYVE9; GCGR, BTN2A1, CNTD2, COQ9, and ZNF205; GCGR, BTN2A1, CNTD2, EMX2, and EP300; GCGR, BTN2A1, CNTD2, EMX2, and FGF2; GCGR, BTN2A1, CNTD2, EMX2, and NAT9; GCGR, BTN2A1, CNTD2, EMX2, and NDUFA9; GCGR, BTN2A1, CNTD2, EMX2, and NEU2; GCGR, BTN2A1, CNTD2, EMX2, and PLA2G1B; GCGR, BTN2A1, CNTD2, EMX2, and PYCR1; GCGR, BTN2A1, CNTD2, EMX2, and RAD51AP1; GCGR, BTN2A1, CNTD2, EMX2, and SEC61G; GCGR, BTN2A1, CNTD2, EMX2, and STRADA; GCGR, BTN2A1, CNTD2, EMX2, and SVOPL; GCGR, BTN2A1, CNTD2, EMX2, and ZFYVE9; GCGR, BTN2A1, CNTD2, EMX2, and ZNF205; GCGR, BTN2A1, CNTD2, EP300, and FGF2; GCGR, BTN2A1, CNTD2, EP300, and NAT9; GCGR, BTN2A1, CNTD2, EP300, and NDUFA9; GCGR, BTN2A1, CNTD2, EP300, and NEU2; GCGR, BTN2A1, CNTD2, EP300, and PLA2G1B; GCGR, BTN2A1, CNTD2, EP300, and PYCR1; GCGR, BTN2A1, CNTD2, EP300, and RAD51AP1; GCGR, BTN2A1, CNTD2, EP300, and SEC61G; GCGR, BTN2A1, CNTD2, EP300, and STRADA; GCGR, BTN2A1, CNTD2, EP300, and SVOPL; GCGR, BTN2A1, CNTD2, EP300, and ZFYVE9; GCGR, BTN2A1, CNTD2, EP300, and ZNF205; GCGR, BTN2A1, CNTD2, FGF2, and NAT9; GCGR, BTN2A1, CNTD2, FGF2, and NDUFA9; GCGR, BTN2A1, CNTD2, FGF2, and NEU2; GCGR, BTN2A1, CNTD2, FGF2, and PLA2G1B; GCGR, BTN2A1, CNTD2, FGF2, and PYCR1; GCGR, BTN2A1, CNTD2, FGF2, and RAD51AP1; GCGR, BTN2A1, CNTD2, FGF2, and SEC61G; GCGR, BTN2A1, CNTD2, FGF2, and STRADA; GCGR, BTN2A1, CNTD2, FGF2, and SVOPL; GCGR, BTN2A1, CNTD2, FGF2, and ZFYVE9; GCGR, BTN2A1, CNTD2, FGF2, and ZNF205; GCGR, BTN2A1, CNTD2, NAT9, and NDUFA9; GCGR, BTN2A1, CNTD2, NAT9, and NEU2; GCGR, BTN2A1, CNTD2, NAT9, and PLA2G1B; GCGR, BTN2A1, CNTD2, NAT9, and PYCR1; GCGR, BTN2A1, CNTD2, NAT9, and RAD51AP1; GCGR, BTN2A1, CNTD2, NAT9, and SEC61G; GCGR, BTN2A1, CNTD2, NAT9, and STRADA; GCGR, BTN2A1, CNTD2, NAT9, and SVOPL; GCGR, BTN2A1, CNTD2, NAT9, and ZFYVE9; GCGR, BTN2A1, CNTD2, NAT9, and ZNF205; GCGR, BTN2A1, CNTD2, NDUFA9, and NEU2; GCGR, BTN2A1, CNTD2, NDUFA9, and PLA2G1B; GCGR, BTN2A1, CNTD2, NDUFA9, and PYCR1; GCGR, BTN2A1, CNTD2, NDUFA9, and RAD51AP1; GCGR, BTN2A1, CNTD2, NDUFA9, and SEC61G; GCGR, BTN2A1, CNTD2, NDUFA9, and STRADA; GCGR, BTN2A1, CNTD2, NDUFA9, and SVOPL; GCGR, BTN2A1, CNTD2, NDUFA9, and ZFYVE9; GCGR, BTN2A1, CNTD2, NDUFA9, and ZNF205; GCGR, BTN2A1, CNTD2, NEU2, and PLA2G1B; GCGR, BTN2A1, CNTD2, NEU2, and PYCR1; GCGR, BTN2A1, CNTD2, NEU2, and RAD51AP1; GCGR, BTN2A1, CNTD2, NEU2, and SEC61G; GCGR, BTN2A1, CNTD2, NEU2, and STRADA; GCGR, BTN2A1, CNTD2, NEU2, and SVOPL; GCGR, BTN2A1, CNTD2, NEU2, and ZFYVE9; GCGR, BTN2A1, CNTD2, NEU2, and ZNF205; GCGR, BTN2A1, CNTD2, PLA2G1B, and PYCR1; GCGR, BTN2A1, CNTD2, PLA2G1B, and RAD51AP1; GCGR, BTN2A1, CNTD2, PLA2G1B, and SEC61G; GCGR, BTN2A1, CNTD2, PLA2G1B, and STRADA; GCGR, BTN2A1, CNTD2, PLA2G1B, and SVOPL; GCGR, BTN2A1, CNTD2, PLA2G1B, and ZFYVE9; GCGR, BTN2A1, CNTD2, PLA2G1B, and ZNF205; GCGR, BTN2A1, CNTD2, PYCR1, and RAD51AP1; GCGR, BTN2A1, CNTD2, PYCR1, and SEC61G; GCGR, BTN2A1, CNTD2, PYCR1, and STRADA; GCGR, BTN2A1, CNTD2, PYCR1, and SVOPL; GCGR, BTN2A1, CNTD2, PYCR1, and ZFYVE9; GCGR, BTN2A1, CNTD2, PYCR1, and ZNF205; GCGR, BTN2A1, CNTD2, RAD51AP1, and SEC61G; GCGR, BTN2A1, CNTD2, RAD51AP1, and STRADA; GCGR, BTN2A1, CNTD2, RAD51AP1, and SVOPL; GCGR, BTN2A1, CNTD2, RAD51AP1, and ZFYVE9; GCGR, BTN2A1, CNTD2, RAD51AP1, and ZNF205; GCGR, BTN2A1, CNTD2, SEC61G, and STRADA; GCGR, BTN2A1, CNTD2, SEC61G, and SVOPL; GCGR, BTN2A1, CNTD2, SEC61G, and ZFYVE9; GCGR, BTN2A1, CNTD2, SEC61G, and ZNF205; GCGR, BTN2A1, CNTD2, STRADA, and SVOPL; GCGR, BTN2A1, CNTD2, STRADA, and ZFYVE9; GCGR, BTN2A1, CNTD2, STRADA, and ZNF205; GCGR, BTN2A1, CNTD2, SVOPL, and ZFYVE9; GCGR, BTN2A1, CNTD2, SVOPL, and ZNF205; GCGR, BTN2A1, CNTD2, ZFYVE9, and ZNF205; GCGR, BTN2A1, COQ9, EMX2, and EP300; GCGR, BTN2A1, COQ9, EMX2, and FGF2; GCGR, BTN2A1, COQ9, EMX2, and NAT9; GCGR, BTN2A1, COQ9, EMX2, and NDUFA9; GCGR, BTN2A1, COQ9, EMX2, and NEU2; GCGR, BTN2A1, COQ9, EMX2, and PLA2G1B; GCGR, BTN2A1, COQ9, EMX2, and PYCR1; GCGR, BTN2A1, COQ9, EMX2, and RAD51AP1; GCGR, BTN2A1, COQ9, EMX2, and SEC61G; GCGR, BTN2A1, COQ9, EMX2, and STRADA; GCGR, BTN2A1, COQ9, EMX2, and SVOPL; GCGR, BTN2A1, COQ9, EMX2, and ZFYVE9; GCGR, BTN2A1, COQ9, EMX2, and ZNF205; GCGR, BTN2A1, COQ9, EP300, and FGF2; GCGR, BTN2A1, COQ9, EP300, and NAT9; GCGR, BTN2A1, COQ9, EP300, and NDUFA9; GCGR, BTN2A1, COQ9, EP300, and NEU2; GCGR, BTN2A1, COQ9, EP300, and PLA2G1B; GCGR, BTN2A1, COQ9, EP300, and PYCR1; GCGR, BTN2A1, COQ9, EP300, and RAD51AP1; GCGR, BTN2A1, COQ9, EP300, and SEC61G; GCGR, BTN2A1, COQ9, EP300, and STRADA; GCGR, BTN2A1, COQ9, EP300, and SVOPL; GCGR, BTN2A1, COQ9, EP300, and ZFYVE9; GCGR, BTN2A1, COQ9, EP300, and ZNF205; GCGR, BTN2A1, COQ9, FGF2, and NAT9; GCGR, BTN2A1, COQ9, FGF2, and NDUFA9; GCGR, BTN2A1, COQ9, FGF2, and NEU2; GCGR, BTN2A1, COQ9, FGF2, and PLA2G1B; GCGR, BTN2A1, COQ9, FGF2, and PYCR1; GCGR, BTN2A1, COQ9, FGF2, and RAD51AP1; GCGR, BTN2A1, COQ9, FGF2, and SEC61G; GCGR, BTN2A1, COQ9, FGF2, and STRADA; GCGR, BTN2A1, COQ9, FGF2, and SVOPL; GCGR, BTN2A1, COQ9, FGF2, and ZFYVE9; GCGR, BTN2A1, COQ9, FGF2, and ZNF205; GCGR, BTN2A1, COQ9, NAT9, and NDUFA9; GCGR, BTN2A1, COQ9, NAT9, and NEU2; GCGR, BTN2A1, COQ9, NAT9, and PLA2G1B; GCGR, BTN2A1, COQ9, NAT9, and PYCR1; GCGR, BTN2A1, COQ9, NAT9, and RAD51AP1; GCGR, BTN2A1, COQ9, NAT9, and SEC61G; GCGR, BTN2A1, COQ9, NAT9, and STRADA; GCGR, BTN2A1, COQ9, NAT9, and SVOPL; GCGR, BTN2A1, COQ9, NAT9, and ZFYVE9; GCGR, BTN2A1, COQ9, NAT9, and ZNF205; GCGR, BTN2A1, COQ9, NDUFA9, and NEU2; GCGR, BTN2A1, COQ9, NDUFA9, and PLA2G1B; GCGR, BTN2A1, COQ9, NDUFA9, and PYCR1; GCGR, BTN2A1, COQ9, NDUFA9, and RAD51AP1; GCGR, BTN2A1, COQ9, NDUFA9, and SEC61G; GCGR, BTN2A1, COQ9, NDUFA9, and STRADA; GCGR, BTN2A1, COQ9, NDUFA9, and SVOPL; GCGR, BTN2A1, COQ9, NDUFA9, and ZFYVE9; GCGR, BTN2A1, COQ9, NDUFA9, and ZNF205; GCGR, BTN2A1, COQ9, NEU2, and PLA2G1B; GCGR, BTN2A1, COQ9, NEU2, and PYCR1; GCGR, BTN2A1, COQ9, NEU2, and RAD51AP1; GCGR, BTN2A1, COQ9, NEU2, and SEC61G; GCGR, BTN2A1, COQ9, NEU2, and STRADA; GCGR, BTN2A1, COQ9, NEU2, and SVOPL; GCGR, BTN2A1, COQ9, NEU2, and ZFYVE9; GCGR, BTN2A1, COQ9, NEU2, and ZNF205; GCGR, BTN2A1, COQ9, PLA2G1B, and PYCR1; GCGR, BTN2A1, COQ9, PLA2G1B, and RAD51AP1; GCGR, BTN2A1, COQ9, PLA2G1B, and SEC61G; GCGR, BTN2A1, COQ9, PLA2G1B, and STRADA; GCGR, BTN2A1, COQ9, PLA2G1B, and SVOPL; GCGR, BTN2A1, COQ9, PLA2G1B, and ZFYVE9; GCGR, BTN2A1, COQ9, PLA2G1B, and ZNF205; GCGR, BTN2A1, COQ9, PYCR1, and RAD51AP1; GCGR, BTN2A1, COQ9, PYCR1, and SEC61G; GCGR, BTN2A1, COQ9, PYCR1, and STRADA; GCGR, BTN2A1, COQ9, PYCR1, and SVOPL; GCGR, BTN2A1, COQ9, PYCR1, and ZFYVE9; GCGR, BTN2A1, COQ9, PYCR1, and ZNF205; GCGR, BTN2A1, COQ9, RAD51AP1, and SEC61G; GCGR, BTN2A1, COQ9, RAD51AP1, and STRADA; GCGR, BTN2A1, COQ9, RAD51AP1, and SVOPL; GCGR, BTN2A1, COQ9, RAD51AP1, and ZFYVE9; GCGR, BTN2A1, COQ9, RAD51AP1, and ZNF205; GCGR, BTN2A1, COQ9, SEC61G, and STRADA; GCGR, BTN2A1, COQ9, SEC61G, and SVOPL; GCGR, BTN2A1, COQ9, SEC61G, and ZFYVE9; GCGR, BTN2A1, COQ9, SEC61G, and ZNF205; GCGR, BTN2A1, COQ9, STRADA, and SVOPL; GCGR, BTN2A1, COQ9, STRADA, and ZFYVE9; GCGR, BTN2A1, COQ9, STRADA, and ZNF205; GCGR, BTN2A1, COQ9, SVOPL, and ZFYVE9; GCGR, BTN2A1, COQ9, SVOPL, and ZNF205; GCGR, BTN2A1, COQ9, ZFYVE9, and ZNF205; GCGR, BTN2A1, EMX2, EP300, and FGF2; GCGR, BTN2A1, EMX2, EP300, and NAT9; GCGR, BTN2A1, EMX2, EP300, and NDUFA9; GCGR, BTN2A1, EMX2, EP300, and NEU2; GCGR, BTN2A1, EMX2, EP300, and PLA2G1B; GCGR, BTN2A1, EMX2, EP300, and PYCR1; GCGR, BTN2A1, EMX2, EP300, and RAD51AP1; GCGR, BTN2A1, EMX2, EP300, and SEC61G; GCGR, BTN2A1, EMX2, EP300, and STRADA; GCGR, BTN2A1, EMX2, EP300, and SVOPL; GCGR, BTN2A1, EMX2, EP300, and ZFYVE9; GCGR, BTN2A1, EMX2, EP300, and ZNF205; GCGR, BTN2A1, EMX2, FGF2, and NAT9; GCGR, BTN2A1, EMX2, FGF2, and NDUFA9; GCGR, BTN2A1, EMX2, FGF2, and NEU2; GCGR, BTN2A1, EMX2, FGF2, and PLA2G1B; GCGR, BTN2A1, EMX2, FGF2, and PYCR1; GCGR, BTN2A1, EMX2, FGF2, and RAD51AP1; GCGR, BTN2A1, EMX2, FGF2, and SEC61G; GCGR, BTN2A1, EMX2, FGF2, and STRADA; GCGR, BTN2A1, EMX2, FGF2, and SVOPL; GCGR, BTN2A1, EMX2, FGF2, and ZFYVE9; GCGR, BTN2A1, EMX2, FGF2, and ZNF205; GCGR, BTN2A1, EMX2, NAT9, and NDUFA9; GCGR, BTN2A1, EMX2, NAT9, and NEU2; GCGR, BTN2A1, EMX2, NAT9, and PLA2G1B; GCGR, BTN2A1, EMX2, NAT9, and PYCR1; GCGR, BTN2A1, EMX2, NAT9, and RAD51AP1; GCGR, BTN2A1, EMX2, NAT9, and SEC61G; GCGR, BTN2A1, EMX2, NAT9, and STRADA; GCGR, BTN2A1, EMX2, NAT9, and SVOPL; GCGR, BTN2A1, EMX2, NAT9, and ZFYVE9; GCGR, BTN2A1, EMX2, NAT9, and ZNF205; GCGR, BTN2A1, EMX2, NDUFA9, and NEU2; GCGR, BTN2A1, EMX2, NDUFA9, and PLA2G1B; GCGR, BTN2A1, EMX2, NDUFA9, and PYCR1; GCGR, BTN2A1, EMX2, NDUFA9, and RAD51AP1; GCGR, BTN2A1, EMX2, NDUFA9, and SEC61G; GCGR, BTN2A1, EMX2, NDUFA9, and STRADA; GCGR, BTN2A1, EMX2, NDUFA9, and SVOPL; GCGR, BTN2A1, EMX2, NDUFA9, and ZFYVE9; GCGR, BTN2A1, EMX2, NDUFA9, and ZNF205; GCGR, BTN2A1, EMX2, NEU2, and PLA2G1B; GCGR, BTN2A1, EMX2, NEU2, and PYCR1; GCGR, BTN2A1, EMX2, NEU2, and RAD51AP1; GCGR, BTN2A1, EMX2, NEU2, and SEC61G; GCGR, BTN2A1, EMX2, NEU2, and STRADA; GCGR, BTN2A1, EMX2, NEU2, and SVOPL; GCGR, BTN2A1, EMX2, NEU2, and ZFYVE9; GCGR, BTN2A1, EMX2, NEU2, and ZNF205; GCGR, BTN2A1, EMX2, PLA2G1B, and PYCR1; GCGR, BTN2A1, EMX2, PLA2G1B, and RAD51AP1; GCGR, BTN2A1, EMX2, PLA2G1B, and SEC61G; GCGR, BTN2A1, EMX2, PLA2G1B, and STRADA; GCGR, BTN2A1, EMX2, PLA2G1B, and SVOPL; GCGR, BTN2A1, EMX2, PLA2G1B, and ZFYVE9; GCGR, BTN2A1, EMX2, PLA2G1B, and ZNF205; GCGR, BTN2A1, EMX2, PYCR1, and RAD51AP1; GCGR, BTN2A1, EMX2, PYCR1, and SEC61G; GCGR, BTN2A1, EMX2, PYCR1, and STRADA; GCGR, BTN2A1, EMX2, PYCR1, and SVOPL; GCGR, BTN2A1, EMX2, PYCR1, and ZFYVE9; GCGR, BTN2A1, EMX2, PYCR1, and ZNF205; GCGR, BTN2A1, EMX2, RAD51AP1, and SEC61G; GCGR, BTN2A1, EMX2, RAD51AP1, and STRADA; GCGR, BTN2A1, EMX2, RAD51AP1, and SVOPL; GCGR, BTN2A1, EMX2, RAD51AP1, and ZFYVE9; GCGR, BTN2A1, EMX2, RAD51AP1, and ZNF205; GCGR, BTN2A1, EMX2, SEC61G, and STRADA; GCGR, BTN2A1, EMX2, SEC61G, and SVOPL; GCGR, BTN2A1, EMX2, SEC61G, and ZFYVE9; GCGR, BTN2A1, EMX2, SEC61G, and ZNF205; GCGR, BTN2A1, EMX2, STRADA, and SVOPL; GCGR, BTN2A1, EMX2, STRADA, and ZFYVE9; GCGR, BTN2A1, EMX2, STRADA, and ZNF205; GCGR, BTN2A1, EMX2, SVOPL, and ZFYVE9; GCGR, BTN2A1, EMX2, SVOPL, and ZNF205; GCGR, BTN2A1, EMX2, ZFYVE9, and ZNF205; GCGR, BTN2A1, EP300, FGF2, and NAT9; GCGR, BTN2A1, EP300, FGF2, and NDUFA9; GCGR, BTN2A1, EP300, FGF2, and NEU2; GCGR, BTN2A1, EP300, FGF2, and PLA2G1B; GCGR, BTN2A1, EP300, FGF2, and PYCR1; GCGR, BTN2A1, EP300, FGF2, and RAD51AP1; GCGR, BTN2A1, EP300, FGF2, and SEC61G; GCGR, BTN2A1, EP300, FGF2, and STRADA; GCGR, BTN2A1, EP300, FGF2, and SVOPL; GCGR, BTN2A1, EP300, FGF2, and ZFYVE9; GCGR, BTN2A1, EP300, FGF2, and ZNF205; GCGR, BTN2A1, EP300, NAT9, and NDUFA9; GCGR, BTN2A1, EP300, NAT9, and NEU2; GCGR, BTN2A1, EP300, NAT9, and PLA2G1B; GCGR, BTN2A1, EP300, NAT9, and PYCR1; GCGR, BTN2A1, EP300, NAT9, and RAD51AP1; GCGR, BTN2A1, EP300, NAT9, and SEC61G; GCGR, BTN2A1, EP300, NAT9, and STRADA; GCGR, BTN2A1, EP300, NAT9, and SVOPL; GCGR, BTN2A1, EP300, NAT9, and ZFYVE9; GCGR, BTN2A1, EP300, NAT9, and ZNF205; GCGR, BTN2A1, EP300, NDUFA9, and NEU2; GCGR, BTN2A1, EP300, NDUFA9, and PLA2G1B; GCGR, BTN2A1, EP300, NDUFA9, and PYCR1; GCGR, BTN2A1, EP300, NDUFA9, and RAD51AP1; GCGR, BTN2A1, EP300, NDUFA9, and SEC61G; GCGR, BTN2A1, EP300, NDUFA9, and STRADA; GCGR, BTN2A1, EP300, NDUFA9, and SVOPL; GCGR, BTN2A1, EP300, NDUFA9, and ZFYVE9; GCGR, BTN2A1, EP300, NDUFA9, and ZNF205; GCGR, BTN2A1, EP300, NEU2, and PLA2G1B; GCGR, BTN2A1, EP300, NEU2, and PYCR1; GCGR, BTN2A1, EP300, NEU2, and RAD51AP1; GCGR, BTN2A1, EP300, NEU2, and SEC61G; GCGR, BTN2A1, EP300, NEU2, and STRADA; GCGR, BTN2A1, EP300, NEU2, and SVOPL; GCGR, BTN2A1, EP300, NEU2, and ZFYVE9; GCGR, BTN2A1, EP300, NEU2, and ZNF205; GCGR, BTN2A1, EP300, PLA2G1B, and PYCR1; GCGR, BTN2A1, EP300, PLA2G1B, and RAD51AP1; GCGR, BTN2A1, EP300, PLA2G1B, and SEC61G; GCGR, BTN2A1, EP300, PLA2G1B, and STRADA; GCGR, BTN2A1, EP300, PLA2G1B, and SVOPL; GCGR, BTN2A1, EP300, PLA2G1B, and ZFYVE9; GCGR, BTN2A1, EP300, PLA2G1B, and ZNF205; GCGR, BTN2A1, EP300, PYCR1, and RAD51AP1; GCGR, BTN2A1, EP300, PYCR1, and SEC61G; GCGR, BTN2A1, EP300, PYCR1, and STRADA; GCGR, BTN2A1, EP300, PYCR1, and SVOPL; GCGR, BTN2A1, EP300, PYCR1, and ZFYVE9; GCGR, BTN2A1, EP300, PYCR1, and ZNF205; GCGR, BTN2A1, EP300, RAD51AP1, and SEC61G; GCGR, BTN2A1, EP300, RAD51AP1, and STRADA; GCGR, BTN2A1, EP300, RAD51AP1, and SVOPL; GCGR, BTN2A1, EP300, RAD51AP1, and ZFYVE9; GCGR, BTN2A1, EP300, RAD51AP1, and ZNF205; GCGR, BTN2A1, EP300, SEC61G, and STRADA; GCGR, BTN2A1, EP300, SEC61G, and SVOPL; GCGR, BTN2A1, EP300, SEC61G, and ZFYVE9; GCGR, BTN2A1, EP300, SEC61G, and ZNF205; GCGR, BTN2A1, EP300, STRADA, and SVOPL; GCGR, BTN2A1, EP300, STRADA, and ZFYVE9; GCGR, BTN2A1, EP300, STRADA, and ZNF205; GCGR, BTN2A1, EP300, SVOPL, and ZFYVE9; GCGR, BTN2A1, EP300, SVOPL, and ZNF205; GCGR, BTN2A1, EP300, ZFYVE9, and ZNF205; GCGR, BTN2A1, FGF2, NAT9, and NDUFA9; GCGR, BTN2A1, FGF2, NAT9, and NEU2; GCGR, BTN2A1, FGF2, NAT9, and PLA2G1B; GCGR, BTN2A1, FGF2, NAT9, and PYCR1; GCGR, BTN2A1, FGF2, NAT9, and RAD51AP1; GCGR, BTN2A1, FGF2, NAT9, and SEC61G; GCGR, BTN2A1, FGF2, NAT9, and STRADA; GCGR, BTN2A1, FGF2, NAT9, and SVOPL; GCGR, BTN2A1, FGF2, NAT9, and ZFYVE9; GCGR, BTN2A1, FGF2, NAT9, and ZNF205; GCGR, BTN2A1, FGF2, NDUFA9, and NEU2; GCGR, BTN2A1, FGF2, NDUFA9, and PLA2G1B; GCGR, BTN2A1, FGF2, NDUFA9, and PYCR1; GCGR, BTN2A1, FGF2, NDUFA9, and RAD51AP1; GCGR, BTN2A1, FGF2, NDUFA9, and SEC61G; GCGR, BTN2A1, FGF2, NDUFA9, and STRADA; GCGR, BTN2A1, FGF2, NDUFA9, and SVOPL; GCGR, BTN2A1, FGF2, NDUFA9, and ZFYVE9; GCGR, BTN2A1, FGF2, NDUFA9, and ZNF205; GCGR, BTN2A1, FGF2, NEU2, and PLA2G1B; GCGR, BTN2A1, FGF2, NEU2, and PYCR1; GCGR, BTN2A1, FGF2, NEU2, and RAD51AP1; GCGR, BTN2A1, FGF2, NEU2, and SEC61G; GCGR, BTN2A1, FGF2, NEU2, and STRADA; GCGR, BTN2A1, FGF2, NEU2, and SVOPL; GCGR, BTN2A1, FGF2, NEU2, and ZFYVE9; GCGR, BTN2A1, FGF2, NEU2, and ZNF205; GCGR, BTN2A1, FGF2, PLA2G1B, and PYCR1; GCGR, BTN2A1, FGF2, PLA2G1B, and RAD51AP1; GCGR, BTN2A1, FGF2, PLA2G1B, and SEC61G; GCGR, BTN2A1, FGF2, PLA2G1B, and STRADA; GCGR, BTN2A1, FGF2, PLA2G1B, and SVOPL; GCGR, BTN2A1, FGF2, PLA2G1B, and ZFYVE9; GCGR, BTN2A1, FGF2, PLA2G1B, and ZNF205; GCGR, BTN2A1, FGF2, PYCR1, and RAD51AP1; GCGR, BTN2A1, FGF2, PYCR1, and SEC61G; GCGR, BTN2A1, FGF2, PYCR1, and STRADA; GCGR, BTN2A1, FGF2, PYCR1, and SVOPL; GCGR, BTN2A1, FGF2, PYCR1, and ZFYVE9; GCGR, BTN2A1, FGF2, PYCR1, and ZNF205; GCGR, BTN2A1, FGF2, RAD51AP1, and SEC61G; GCGR, BTN2A1, FGF2, RAD51AP1, and STRADA; GCGR, BTN2A1, FGF2, RAD51AP1, and SVOPL; GCGR, BTN2A1, FGF2, RAD51AP1, and ZFYVE9; GCGR, BTN2A1, FGF2, RAD51AP1, and ZNF205; GCGR, BTN2A1, FGF2, SEC61G, and STRADA; GCGR, BTN2A1, FGF2, SEC61G, and SVOPL; GCGR, BTN2A1, FGF2, SEC61G, and ZFYVE9; GCGR, BTN2A1, FGF2, SEC61G, and ZNF205; GCGR, BTN2A1, FGF2, STRADA, and SVOPL; GCGR, BTN2A1, FGF2, STRADA, and ZFYVE9; GCGR, BTN2A1, FGF2, STRADA, and ZNF205; GCGR, BTN2A1, FGF2, SVOPL, and ZFYVE9; GCGR, BTN2A1, FGF2, SVOPL, and ZNF205; GCGR, BTN2A1, FGF2, ZFYVE9, and ZNF205; GCGR, BTN2A1, NAT9, NDUFA9, and NEU2; GCGR, BTN2A1, NAT9, NDUFA9, and PLA2G1B; GCGR, BTN2A1, NAT9, NDUFA9, and PYCR1; GCGR, BTN2A1, NAT9, NDUFA9, and RAD51AP1; GCGR, BTN2A1, NAT9, NDUFA9, and SEC61G; GCGR, BTN2A1, NAT9, NDUFA9, and STRADA; GCGR, BTN2A1, NAT9, NDUFA9, and SVOPL; GCGR, BTN2A1, NAT9, NDUFA9, and ZFYVE9; GCGR, BTN2A1, NAT9, NDUFA9, and ZNF205; GCGR, BTN2A1, NAT9, NEU2, and PLA2G1B; GCGR, BTN2A1, NAT9, NEU2, and PYCR1; GCGR, BTN2A1, NAT9, NEU2, and RAD51AP1; GCGR, BTN2A1, NAT9, NEU2, and SEC61G; GCGR, BTN2A1, NAT9, NEU2, and STRADA; GCGR, BTN2A1, NAT9, NEU2, and SVOPL; GCGR, BTN2A1, NAT9, NEU2, and ZFYVE9; GCGR, BTN2A1, NAT9, NEU2, and ZNF205; GCGR, BTN2A1, NAT9, PLA2G1B, and PYCR1; GCGR, BTN2A1, NAT9, PLA2G1B, and RAD51AP1; GCGR, BTN2A1, NAT9, PLA2G1B, and SEC61G; GCGR, BTN2A1, NAT9, PLA2G1B, and STRADA; GCGR, BTN2A1, NAT9, PLA2G1B, and SVOPL; GCGR, BTN2A1, NAT9, PLA2G1B, and ZFYVE9; GCGR, BTN2A1, NAT9, PLA2G1B, and ZNF205; GCGR, BTN2A1, NAT9, PYCR1, and RAD51AP1; GCGR, BTN2A1, NAT9, PYCR1, and SEC61G; GCGR, BTN2A1, NAT9, PYCR1, and STRADA; GCGR, BTN2A1, NAT9, PYCR1, and SVOPL; GCGR, BTN2A1, NAT9, PYCR1, and ZFYVE9; GCGR, BTN2A1, NAT9, PYCR1, and ZNF205; GCGR, BTN2A1, NAT9, RAD51AP1, and SEC61G; GCGR, BTN2A1, NAT9, RAD51AP1, and STRADA; GCGR, BTN2A1, NAT9, RAD51AP1, and SVOPL; GCGR, BTN2A1, NAT9, RAD51AP1, and ZFYVE9; GCGR, BTN2A1, NAT9, RAD51AP1, and ZNF205; GCGR, BTN2A1, NAT9, SEC61G, and STRADA; GCGR, BTN2A1, NAT9, SEC61G, and SVOPL; GCGR, BTN2A1, NAT9, SEC61G, and ZFYVE9; GCGR, BTN2A1, NAT9, SEC61G, and ZNF205; GCGR, BTN2A1, NAT9, STRADA, and SVOPL; GCGR, BTN2A1, NAT9, STRADA, and ZFYVE9; GCGR, BTN2A1, NAT9, STRADA, and ZNF205; GCGR, BTN2A1, NAT9, SVOPL, and ZFYVE9; GCGR, BTN2A1, NAT9, SVOPL, and ZNF205; GCGR, BTN2A1, NAT9, ZFYVE9, and ZNF205; GCGR, BTN2A1, NDUFA9, NEU2, and PLA2G1B; GCGR, BTN2A1, NDUFA9, NEU2, and PYCR1; GCGR, BTN2A1, NDUFA9, NEU2, and RAD51AP1; GCGR, BTN2A1, NDUFA9, NEU2, and SEC61G; GCGR, BTN2A1, NDUFA9, NEU2, and STRADA; GCGR, BTN2A1, NDUFA9, NEU2, and SVOPL; GCGR, BTN2A1, NDUFA9, NEU2, and ZFYVE9; GCGR, BTN2A1, NDUFA9, NEU2, and ZNF205; GCGR, BTN2A1, NDUFA9, PLA2G1B, and PYCR1; GCGR, BTN2A1, NDUFA9, PLA2G1B, and RAD51AP1; GCGR, BTN2A1, NDUFA9, PLA2G1B, and SEC61G; GCGR, BTN2A1, NDUFA9, PLA2G1B, and STRADA; GCGR, BTN2A1, NDUFA9, PLA2G1B, and SVOPL; GCGR, BTN2A1, NDUFA9, PLA2G1B, and ZFYVE9; GCGR, BTN2A1, NDUFA9, PLA2G1B, and ZNF205; GCGR, BTN2A1, NDUFA9, PYCR1, and RAD51AP1; GCGR, BTN2A1, NDUFA9, PYCR1, and SEC61G; GCGR, BTN2A1, NDUFA9, PYCR1, and STRADA; GCGR, BTN2A1, NDUFA9, PYCR1, and SVOPL; GCGR, BTN2A1, NDUFA9, PYCR1, and ZFYVE9; GCGR, BTN2A1, NDUFA9, PYCR1, and ZNF205; GCGR, BTN2A1, NDUFA9, RAD51AP1, and SEC61G; GCGR, BTN2A1, NDUFA9, RAD51AP1, and STRADA; GCGR, BTN2A1, NDUFA9, RAD51AP1, and SVOPL; GCGR, BTN2A1, NDUFA9, RAD51AP1, and ZFYVE9; GCGR, BTN2A1, NDUFA9, RAD51AP1, and ZNF205; GCGR, BTN2A1, NDUFA9, SEC61G, and STRADA; GCGR, BTN2A1, NDUFA9, SEC61G, and SVOPL; GCGR, BTN2A1, NDUFA9, SEC61G, and ZFYVE9; GCGR, BTN2A1, NDUFA9, SEC61G, and ZNF205; GCGR, BTN2A1, NDUFA9, STRADA, and SVOPL; GCGR, BTN2A1, NDUFA9, STRADA, and ZFYVE9; GCGR, BTN2A1, NDUFA9, STRADA, and ZNF205; GCGR, BTN2A1, NDUFA9, SVOPL, and ZFYVE9; GCGR, BTN2A1, NDUFA9, SVOPL, and ZNF205; GCGR, BTN2A1, NDUFA9, ZFYVE9, and ZNF205; GCGR, BTN2A1, NEU2, PLA2G1B, and PYCR1; GCGR, BTN2A1, NEU2, PLA2G1B, and RAD51AP1; GCGR, BTN2A1, NEU2, PLA2G1B, and SEC61G; GCGR, BTN2A1, NEU2, PLA2G1B, and STRADA; GCGR, BTN2A1, NEU2, PLA2G1B, and SVOPL; GCGR, BTN2A1, NEU2, PLA2G1B, and ZFYVE9; GCGR, BTN2A1, NEU2, PLA2G1B, and ZNF205; GCGR, BTN2A1, NEU2, PYCR1, and RAD51AP1; GCGR, BTN2A1, NEU2, PYCR1, and SEC61G; GCGR, BTN2A1, NEU2, PYCR1, and STRADA; GCGR, BTN2A1, NEU2, PYCR1, and SVOPL; GCGR, BTN2A1, NEU2, PYCR1, and ZFYVE9; GCGR, BTN2A1, NEU2, PYCR1, and ZNF205; GCGR, BTN2A1, NEU2, RAD51AP1, and SEC61G; GCGR, BTN2A1, NEU2, RAD51AP1, and STRADA; GCGR, BTN2A1, NEU2, RAD51AP1, and SVOPL; GCGR, BTN2A1, NEU2, RAD51AP1, and ZFYVE9; GCGR, BTN2A1, NEU2, RAD51AP1, and ZNF205; GCGR, BTN2A1, NEU2, SEC61G, and STRADA; GCGR, BTN2A1, NEU2, SEC61G, and SVOPL; GCGR, BTN2A1, NEU2, SEC61G, and ZFYVE9; GCGR, BTN2A1, NEU2, SEC61G, and ZNF205; GCGR, BTN2A1, NEU2, STRADA, and SVOPL; GCGR, BTN2A1, NEU2, STRADA, and ZFYVE9; GCGR, BTN2A1, NEU2, STRADA, and ZNF205; GCGR, BTN2A1, NEU2, SVOPL, and ZFYVE9; GCGR, BTN2A1, NEU2, SVOPL, and ZNF205; GCGR, BTN2A1, NEU2, ZFYVE9, and ZNF205; GCGR, BTN2A1, PLA2G1B, PYCR1, and RAD51AP1; GCGR, BTN2A1, PLA2G1B, PYCR1, and SEC61G; GCGR, BTN2A1, PLA2G1B, PYCR1, and STRADA; GCGR, BTN2A1, PLA2G1B, PYCR1, and SVOPL; GCGR, BTN2A1, PLA2G1B, PYCR1, and ZFYVE9; GCGR, BTN2A1, PLA2G1B, PYCR1, and ZNF205; GCGR, BTN2A1, PLA2G1B, RAD51AP1, and SEC61G; GCGR, BTN2A1, PLA2G1B, RAD51AP1, and STRADA; GCGR, BTN2A1, PLA2G1B, RAD51AP1, and SVOPL; GCGR, BTN2A1, PLA2G1B, RAD51AP1, and ZFYVE9; GCGR, BTN2A1, PLA2G1B, RAD51AP1, and ZNF205; GCGR, BTN2A1, PLA2G1B, SEC61G, and STRADA; GCGR, BTN2A1, PLA2G1B, SEC61G, and SVOPL; GCGR, BTN2A1, PLA2G1B, SEC61G, and ZFYVE9; GCGR, BTN2A1, PLA2G1B, SEC61G, and ZNF205; GCGR, BTN2A1, PLA2G1B, STRADA, and SVOPL; GCGR, BTN2A1, PLA2G1B, STRADA, and ZFYVE9; GCGR, BTN2A1, PLA2G1B, STRADA, and ZNF205; GCGR, BTN2A1, PLA2G1B, SVOPL, and ZFYVE9; GCGR, BTN2A1, PLA2G1B, SVOPL, and ZNF205; GCGR, BTN2A1, PLA2G1B, ZFYVE9, and ZNF205; GCGR, BTN2A1, PYCR1, RAD51AP1, and SEC61G; GCGR, BTN2A1, PYCR1, RAD51AP1, and STRADA; GCGR, BTN2A1, PYCR1, RAD51AP1, and SVOPL; GCGR, BTN2A1, PYCR1, RAD51AP1, and ZFYVE9; GCGR, BTN2A1, PYCR1, RAD51AP1, and ZNF205; GCGR, BTN2A1, PYCR1, SEC61G, and STRADA; GCGR, BTN2A1, PYCR1, SEC61G, and SVOPL; GCGR, BTN2A1, PYCR1, SEC61G, and ZFYVE9; GCGR, BTN2A1, PYCR1, SEC61G, and ZNF205; GCGR, BTN2A1, PYCR1, STRADA, and SVOPL; GCGR, BTN2A1, PYCR1, STRADA, and ZFYVE9; GCGR, BTN2A1, PYCR1, STRADA, and ZNF205; GCGR, BTN2A1, PYCR1, SVOPL, and ZFYVE9; GCGR, BTN2A1, PYCR1, SVOPL, and ZNF205; GCGR, BTN2A1, PYCR1, ZFYVE9, and ZNF205; GCGR, BTN2A1, RAD51AP1, SEC61G, and STRADA; GCGR, BTN2A1, RAD51AP1, SEC61G, and SVOPL; GCGR, BTN2A1, RAD51AP1, SEC61G, and ZFYVE9; GCGR, BTN2A1, RAD51AP1, SEC61G, and ZNF205; GCGR, BTN2A1, RAD51AP1, STRADA, and SVOPL; GCGR, BTN2A1, RAD51AP1, STRADA, and ZFYVE9; GCGR, BTN2A1, RAD51AP1, STRADA, and ZNF205; GCGR, BTN2A1, RAD51AP1, SVOPL, and ZFYVE9; GCGR, BTN2A1, RAD51AP1, SVOPL, and ZNF205; GCGR, BTN2A1, RAD51AP1, ZFYVE9, and ZNF205; GCGR, BTN2A1, SEC61G, STRADA, and SVOPL; GCGR, BTN2A1, SEC61G, STRADA, and ZFYVE9; GCGR, BTN2A1, SEC61G, STRADA, and ZNF205; GCGR, BTN2A1, SEC61G, SVOPL, and ZFYVE9; GCGR, BTN2A1, SEC61G, SVOPL, and ZNF205; GCGR, BTN2A1, SEC61G, ZFYVE9, and ZNF205; GCGR, BTN2A1, STRADA, SVOPL, and ZFYVE9; GCGR, BTN2A1, STRADA, SVOPL, and ZNF205; GCGR, BTN2A1, STRADA, ZFYVE9, and ZNF205; and GCGR, BTN2A1, SVOPL, ZFYVE9, and ZNF205. In one aspect, disclosed herein are cells or cell lines comprising decreased expression of SEC61G and one or more of BTN2A1, CNTD2, COQ9, EMX2, EP300, FGF2, GCGR, NAT9, NDUFA9, NEU2, PLA2G1B, PYCR1, RAD51AP1, STRADA, SVOPL, ZFYVE9, and/or ZNF205. Also disclosed herein are cells or cell lines comprising decreased expression of STRADA and one or more of BTN2A1, CNTD2, COQ9, EMX2, EP300, FGF2, GCGR, NAT9, NDUFA9, NEU2, PLA2G1B, PYCR1, RAD51AP1, SEC61G, SVOPL, ZFYVE9, and/or ZNF205. Cells or cell lines comprising reduced expression of any other combination of two or more of the disclosed genes BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 are specifically disclosed herein. For example, cells or cell lines with reduced expression of any combination of two or more of CNTD2, GCGR, PYCR1, RAD51AP1, ZFYVE9, and ZNF205; any combination of two or more of CNTD2, GCGR, NAT9, PYCR1, SVOPL, and ZNF205; any combination of two or more of BTN2A1, CNTD2, COQ9, EP300, GCGR, NDUFA9, PLA2G1B, RAD51AP1, SEC61G, STRADA, SVOPL, ZFYVE9, and ZNF205; any combination of two or more of BTN2A1, CNTD2, RAD51AP1, SEC61G, and SVOPL; any combination of two or more of BTN2A1, CNTD2, COQ9, EP300, GCGR, NAT9, SEC61G, and ZNF205; any combination of two or more of EMX2, EP300, FGF2, NAT9, PYCR1, SEC61G, SVOPL, and ZFYVE9; any combination of BTN2A1, CNTD2, COQ9, FGF2, GCGR, NAT9, NDUFA9, NEU2, PLA2G1B, RAD51AP1, SEC61G, STRADA, SVOPL, ZFYVE9, and ZNF205; any combination of two or more of BTN2A1, CNTD2, EP300, GCGR, NAT9, PYCR1, RAD51AP1, ZFYVE9, and ZNF205; any combination of two or more of BTN2A1, CNTD2, EP300, GCGR, PLA2G1B, SVOPL, and ZNF205; any combination of two or more of COQ9, EMX2, EP300, FGF2, GCGR, NAT9, NDUFA9, RAD51AP1, SEC61G, STRADA, SVOPL, ZFYVE9, and ZNF205; and/or any combination of two or more of CNTD2, COQ9, EMX2, EP300, GCGR, NDUFA9, NEU2, PLA2G1B, PYCR1, SEC61G, SVOPL, ZFYVE9, and ZNF205 are also disclosed. Also disclosed are cells or cell lines comprising decreased expression of one or more of BTN2A1, CNTD2, ZNF205, GCGR, and/or EP300; decreased expression of one, two, or three or more of PYCR1, RAD51AP1, ZFYVE9, and/or ZNF205; decreased expression of one, two, or three or more of CNTD2, NAT9, PYCR1, SVOPL, and/or ZNF205; decreased expression of one, two, three, four, or more of ZFYVE9, EMX2, FGF2, PLA2G1B, and/or PYCR1; and/or decreased expression of one, two, three, four, or more of COQ9, NAT9, NDUFA9, NEU2, RAD51AP1, and/or SVOPL.

Cells with reduced BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 expression do not include any cell that naturally has reduced expression of any one or more of BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205, but only includes cells where reduced expression is the result of human manipulation or genetic engineering to the specific cell or the cell line through any of the means for reducing gene expression disclosed herein or otherwise known in the art. Accordingly, the reduction is relative to an unmodified cell or cell line of the same type.

The disclosed cells and cell lines derived therefrom can be any cell or cell line that can be stably infected with virus. In one aspect, the cells can be of mammalian origin (including, human, simian, porcine, bovine, equine, canine, feline, rodent (e.g., rabbit, rat, mouse, and guinea pig), and non-human primate) or avian including chicken, duck, ostrich, and turkey cells. It is further contemplated that the cell can be a cell of an established mammalian cell line including, but not limited to MA104 cells, VERO cells, Madin-Darby Canine Kidney (MDCK) cells, HEp-2 cells, HeLa cells, HEK293 cells, MRC-5 cells, WI-38 cells, EB66, and PER C6 cells.

In one aspect, the cells or cell lines disclosed herein can have reduced expression or copy number of genes, mRNA, or proteins or reduced protein activity that inhibits viral production relative to an unmodified version of the same cell type or cell line. Reduction in expression can be at least a 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the gene expression, mRNA translation, protein expression, or protein activity relative to a control. For example, disclosed herein are cells and/or cell lines comprising at least 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the expression of at least one gene selected from BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 genes relative to a control.

It is further understood that one way of referring to a reduction rather than the percentage reduction is as a percentage of the control expression or activity. For example, a cell with at least a 15% reduction in the expression of a particular gene relative to a control would also be a gene with expression that is less than or equal to 85% of the expression of the control. Accordingly, in one aspect, disclosed herein are cells or cell lines wherein the gene expression, mRNA expression, protein expression, or protein activity is less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% of a control. Thus, disclosed herein are cells or cell lines comprising less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 relative to a control. For example, disclosed herein are cell comprising less than or equal to 85% reduction of the expression of at least one gene selected from BTN2A1, CNTD2, COQ9, EMX2, EP300, FGF2, FGFR, GCGR, NAT9, NDUFA9, NEU2, PLA2G1B, PYCR1, RAD51AP1, SEC61G, STRADA, SVOPL, ZFYVE9, and/or ZNF205 relative to a control.

It is understood and herein contemplated that the reduced expression can be achieved by any means known in the art including techniques that manipulate genomic DNA, messenger and/or non-coding RNA and/or proteins including but not limited to endogenous or exognenous control elements (e.g., siRNA, shRNA, small molecule inhibitor, and antisense oligonucleotide) and mutations in or directly targeting the coding region of the gene, mRNA, or protein or a control element or mutation in a regulator region operably linked to the gene, mRNA, or protein. As such, the technologies or mechanisms that can be employed to modulate a gene of interest include but are not limited to 1) technologies and reagents that target genomic DNA to result in an edited genome (e.g., homologous recombination to introduce a mutation such as a deletion into a gene, zinc finger nucleases, meganucleases, transcription activator-like effectors (e.g., TALENs), triplexes, mediators of epigenetic modification, and CRISPR and rAAV technologies), 2) technologies and reagents that target RNA (e.g. agents that act through the RNAi pathway, antisense technologies, ribozyme technologies), and 3) technologies that target proteins (e.g., small molecules, aptamers, peptides, auxin- or FKBP-mediated destabilizing domains, antibodies).

In one embodiment for targeting DNA, gene modulation is achieved using zinc finger nucleases (ZFNs). Synthetic ZFNs are composed of a custom designed zinc finger binding domain fused with e.g. a Fold DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. Meganucleases, triplexes, TALENs, CRISPR/cas9, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous or exogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5 ' UTR, the open reading frame, the 3' UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2) lipid-mediated delivery, 3) electroporation, or 4) vector/plasmid-based expression systems. An introduced RNA molecule may be referred to as an exogenous nucleotide sequence or polynucleotide.

Another gene targeting reagent that uses RNAi pathways includes exogenous small hairpin RNA, also referred to as shRNA. shRNAs delivered to cells via e.g., expression constructs (e.g., plasmids, lentiviruses) have the ability to provide long term gene knockdown in a constitutive or regulated manner, depending upon the type of promoter employed. In one preferred embodiment, the genome of a lentiviral particle is modified to include one or more shRNA expression cassettes that target a gene (or genes) of interest. Such lentiviruses can infect a cell intended for vaccine production, stably integrate their viral genome into the host genome, and express the shRNA(s) in a 1) constitutive, 2) regulated, or (in the case where multiple shRNA are being expressed) constitutive and regulated fashion. In this way, cell lines having enhanced virus production capabilities can be created. It is worth noting, that approaches that use siRNA or shRNA have the added benefit in that they can be designed to target individual variants of a single gene or multiple closely related gene family members. In this way, individual reagents can be used to modulate larger collections of targets having similar or redundant functions or sequence motifs. The skilled person will recognize that lentiviral constructs can also incorporate cloned DNA, or ORF expression constructs.

In another embodiment for modulating gene function, gene suppression can be achieved by large scale transfection of cells with miRNA mimics or miRNA inhibitors introduced into the cells.

In another embodiment, modulation takes place at the protein level. By example, knockdown of gene function at the protein level can be achieved by a number of means including but not limited to targeting the protein with a small molecule, a peptide, an aptamer, destabilizing domains, or other methods that can e.g., down-regulate the activity or enhance the rate of degradation of a gene product. In one preferred instance, a small molecule that binds e.g. an active site and inhibits the function of a target protein can be added to e.g., the cell culture media and thereby introduced into the cell. Alternatively, target protein function can be modulated by introducing e.g., a peptide into a cell that (for instance) prevents protein-protein interactions (see for instance, Shangary et. al., (2009) Annual Review of Pharmacology and Toxicology 49:223). Such peptides can be introduced into a cell by transfection or electroporation, or introduced via an expression construct. Alternatively, peptides can be introduced into cells by 1) adding (e.g., through conjugation) one or more moieties that facilitate cellular delivery, or 2) supercharging molecules to enhance self-delivery (Cronican, J. J. et al (2010) ACS Chem. Biol. 5(8):747-52). Techniques for expressing a peptide include, but are not limited to 1) fusion of the peptide to a scaffold, or 2) attachment of a signal sequence, to stabilize or direct the peptide to a position or compartment of interest, respectively.

As discussed above, the compositions and methods disclosed herein fully contemplate cell lines comprising the cells described herein. As used herein, the term "cell line" refers to a clonal population of cells that are able to continue to divide and not undergo senescence. The cell(s) can be derived from any number of sources including mammalian (including but not limited to human, non-human primate, hamster, dog), avian (e.g., chicken, duck), insect, and more. The cell lines contemplated herein can also be modified versions of existing cell lines including but not limited to MA104 cells, VERO cells, Madin-Darby Canine Kidney (MDCK) cells, HEp-2 cells, HeLa cells, HEK293 cells, MRC-5 cells, WI-38 cells, EB66, and PER C6 cells. Preferably, the modified genes enhance RV antigen production or production of virus strains used to produce RV vaccines. Preferably, the cell line and the virus or RV antigen are employed in virus vaccine production. Thus, in one aspect disclosed herein are cell lines (including engineered cell lines) comprising a cell; wherein the cell comprises decreased expression of at least one gene selected from BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 genes relative to a control. Also disclosed herein are manipulated, engineered, and/or recombinant vero cells comprising reduced expression of any one or combination of two or more of BTN2A1, CNTD2, EP300, GCGR, PYCR1, and/or ZNF205.

The original screen for genes that enhance virus production took place in one of three different cell lines, HEp-2C, MA-104, and Vero. MA104 cells are derived from *Macaca mulatta* and Vero cells are derived from African Green Monkey (Chlorocebus). HEp-2C cells are a human cell line derived from a human cervical carcinoma (e.g., ATCC CCL23). As described in the Examples section below, validation of the identified gene targets with additional viruses utilized VERO cells. In cases where the gene targets enhance production of the viruses under investigation, an additional embodiment includes a list of genes that are orthologs of those identified in the primary screen (Table I). Such orthologs can be modulated in human or non-human cells or cell lines to increase virus or virus antigen production.

Another embodiment includes knockout animals (e.g., knockout mice) having one or more of the genes identified in the Table 1 below modified to enhance virus replication. For example, disclosed herein are knockout animals having one or more of the genes selected from the group comprising BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 modified to enhance virus replication.

1. Nucleic Acids

There are a variety of molecules disclosed herein that are nucleic acid based, including for example the nucleic acids that encode, for example BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, or any of the nucleic acids disclosed herein for making BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205 knockouts, knockdowns, variants, mutants, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U or variants thereof. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; 0-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to $—O[(CH_2)_nO]_m CH_3$, $—O(CH_2)_n OCH_3$, $—O(CH_2)_n NH_2$, $—O(CH_2)_n CH_3$, $—O(CH_2)_n—ONH_2$, and $—O(CH_2)_nON[(CH_2)_n CH_3)]_2$, where n and m are from 1 to about 10.

Other modifications at the 2' position include but are not limited to: $C_1$ to Cm lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, or any of the nucleic acids disclosed herein for making BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those of skill in the art understand how to resolve sequence discrepancies and differences and to adjust the compositions and methods relating to a particular sequence to other related sequences. Primers and/or probes can be designed for any given sequence given the information disclosed herein and known in the art.

c) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of any of the disclosed nucleic acids, such as BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, or the genomic DNA of any of the disclosed nucleic acids, such as BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205, or they can interact with the polypeptide encoded by any of the disclosed nucleic acids, such as BTN2A1, CNTD2, COQ9, EMX2, EP300, FGF2, GCGR, NAT9, NDUFA9, NEU2, PLA2G1B, PYCR1, RAD51AP1, SEC61G, STRADA, SVOPL, ZFYVE9, and/or ZNF205. Often functional nucleic acids are designed to interact with other nucleic acids based on sequence complementarity between the target molecule and the functional nucleic acid molecule. In other situations, the specific recognition between the functional nucleic acid molecule and the target molecule is not based on sequence complementarity between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAse mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline, as well as large molecules, such as reverse transcriptase and thrombin. Aptamers can bind very tightly with kds from the target molecule of less than $10^{-12}$ M. It is preferred that the aptamers bind the target molecule with a kd less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a kd with the target molecule at least 10, 100, 1000, 10,000, or 100,000 fold lower than the $k_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate.

2. Nucleic Acid Delivery

In the methods described above which include the administration and uptake of exogenous DNA or RNA into the cells of a subject or cell (i.e., gene transduction or transfection), the disclosed nucleic acids can be in the form of naked DNA or RNA, or the nucleic acids can be in a vector for delivering the nucleic acids to the cells, whereby the DNA or RNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudo-typed retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

a) Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, include chemical transfectants, or physico-mechanical methods such as electroporation and direct diffusion of DNA. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

b) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus.

Viral vectors are, for example, Adenovirus, Adeno-associated virus, Herpes virus, Lenti virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature.

viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

c) Retroviral Vectors

A retrovirus is an animal virus belonging to the virus family of Retroviridae, including any types, subfamilies, genus, or tropisms (e.g., Lentivirus). Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

d) Adenoviral Vectors

The construction of replication-defective adenoviruses has been described. The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites. Recombinant adenoviruses achieve gene transduction by binding to specific cell surface receptors, after which the virus is internalized by receptor-mediated endocytosis, in the same manner as wild type or replication-defective adenovirus A viral vector can be one based on an adenovirus which has had the E1 gene removed and these virons are generated in a cell line such as the CHO and HEK293 cell lines. In another preferred embodiment both the E1 and E3 genes are removed from the adenovirus genome.

e) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

f) Large Payload Viral Vectors

Molecular genetic experiments with large human herpesviruses have provided a means whereby large heterologous DNA fragments can be cloned, propagated and established in cells permissive for infection with herpesviruses. These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

g) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, and type of ligand, ligand valency, and ligand concentration.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

3. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers f unction to increase transcription from nearby promoters Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

In certain embodiments the promoter and/or enhancer region can act as a constitutive promoter and/or enhancer to maximize expression of the region of the transcription unit to be transcribed. Thus, in one embodiment disclosed herein are recombinant cells comprising one or more microRNA and at least one immunoglobulin encoding nucleic acid wherein the expression of the microRNa is constitutive. In such circumstances, the microRNA can be operationally linked to the constitutive promoter. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

In other embodiments, the promoter and/or enhancer region can act as an inducible promoter and/or enhancer to regulate expression of the region of the transcript to be transcribed. The promoter and/or enhancer may be specifically activated either by light, temperature, or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs. Other examples of inducible promoter systems include but are not limited to GAL4 promoter, Lac promoter, Cre recombinase (such as in a cre-lox inducible system), metal-regulated systems such as metallothionein, Flp-FRT recombinase, alcohol dehydrogenase I (alcA) promoter, and steroid regulated systems, such as, estrogen receptor (ER) and glucocorticoid receptor (GR). Inducible systems can also comprise inducible stem loop expression systems. Thus, in one embodiment disclosed herein are recombinant cells comprising one or more microRNA and at least one immunoglobulin encoding nucleic acid wherein the expression of the microRNA is inducible.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA.

The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Sequence Similarities

It is understood that as discussed herein the use of the terms “homology” and “identity” mean the same thing as “similarity.” Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Unless otherwise indicated, all numbers expressing quantities of components, molecular weights, and so forth used in the specification and claims are to be understood as being modified in all instances by the term “about.” Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety.

In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

5. Example 1 a) Methods (1) Cells:

Both Hep2C and Vero cells were maintained in Dulbecco's modified Eagle's medium (DMEM, Thermo Fisher Scientific, Cat. # Sh30243.01) supplemented with 10% calf serum (HyClone, Cat. # Sh30396.03) and containing 1% penicillin-streptomycin (Cellgro, Cat. #30-004-CI) during propagation. For most experiments Vero cells were plated at a density of 8,500 cells/well and HEp-2C cells were plated at a density of 9,500 cells per well.

(2) siRNAs and Genes being Targeted:

The ON-TARGETplus siRNA (OTP-siRNA) library (Dharmacon) was used in the described studies. OTP silencing reagents are provided as a pool of siRNA targeting each gene. Each pool contains 4 individual siRNAs targeting different regions of the open reading frame (ORF). siRNA pools are designed to target all splice variants of the genes, thus in cases where a particular Accession Number is identified, it is understood that all variants of that gene are targeted by the siRNA. The list of genes being targeted is included in Table 1.

(3) Transfection of siRNAs into Cells:

For siRNA transfections, On-TARGETplus (OTP)-siRNAs (Dharmacon Products) were reverse transfected into cells at a final siRNA concentration of 50 nM in 0.4% DharmaFECT4 (DF4, Dharmacon). To achieve this, DF4 was first diluted in serum-free medium (OPTI-MEM) for 5 minutes. This material was then added to 96-well culture plates containing 5 μl of a 1 μM siRNA solution. The DF4-siRNA mixture was then incubated for 20 minutes (room temperature) prior to the addition of cells in Dulbecco's Modified Eagle's Medium supplemented with 10% calf serum. Transfected cells were then cultured for 48 hrs at 37° C., 5% CO2. Subsequently, the media was removed, wells were washed 3× in 1×PVBS, and cells were infected at low MOI (e.g., 0.01) for each virus that was diluted in DMEM containing 2% calf serum and 1% penicillin-streptomycin.

Quantitation of viral titers was performed used art-recognized plaque assays. In the case of Adenovirus, an immunoassay utilizing an antibody directed at the Ad5 capsid protein was used in conjunction with a Cellomics high-content imaging system.

b) Screen Results

Screen of 18 target genes against a range of vaccine viruses was performed to identify genes and gene combinations that could be modulated to enhance vaccine production.

(1) Influenza B Virus

Figure 1:
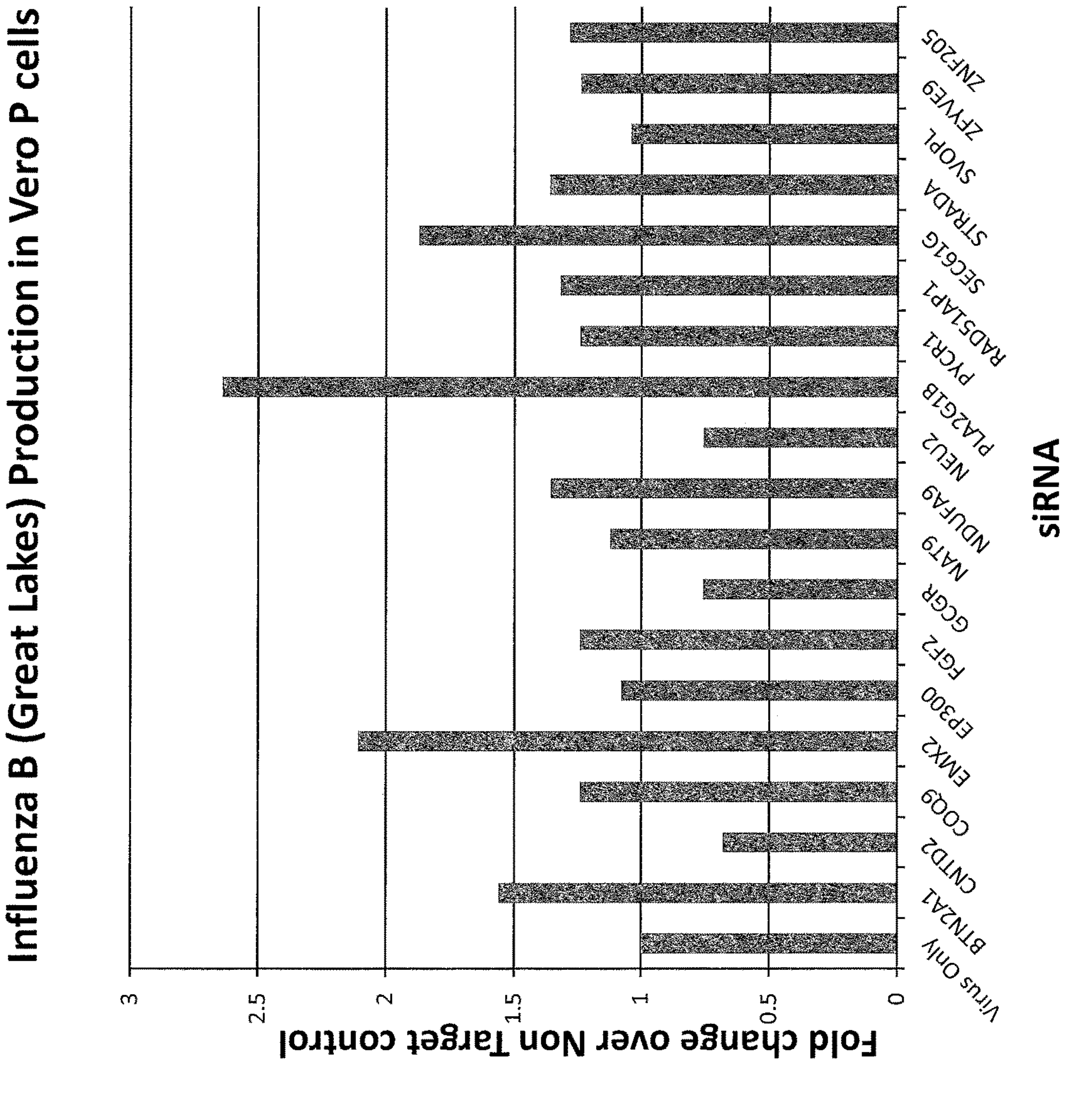
FIG. 1 shows the effects of gene knockdown on Influenza B replication in Vero cells.

The effects of 18 separate gene knockdown events on Influenza B virus titers was assessed using a plaque assay as a means of determining viral titers. Influenza B is a (−) single stranded RNA virus that is a member of the orthomyxoviridae family. The results, shown in FIG. 1, confirm that none of the gene knockdown events enhanced the production of the Great Lakes variant of Influenza B in Vero P cells. Similar results were observed with a second Influenza B strain isolated from Malaysia. In addition, parallel studies in HEp-2C showed that none of the KD events enhanced the production of either strain in the human cell line.

(2) Coxsackie Virus

Figure 2A:
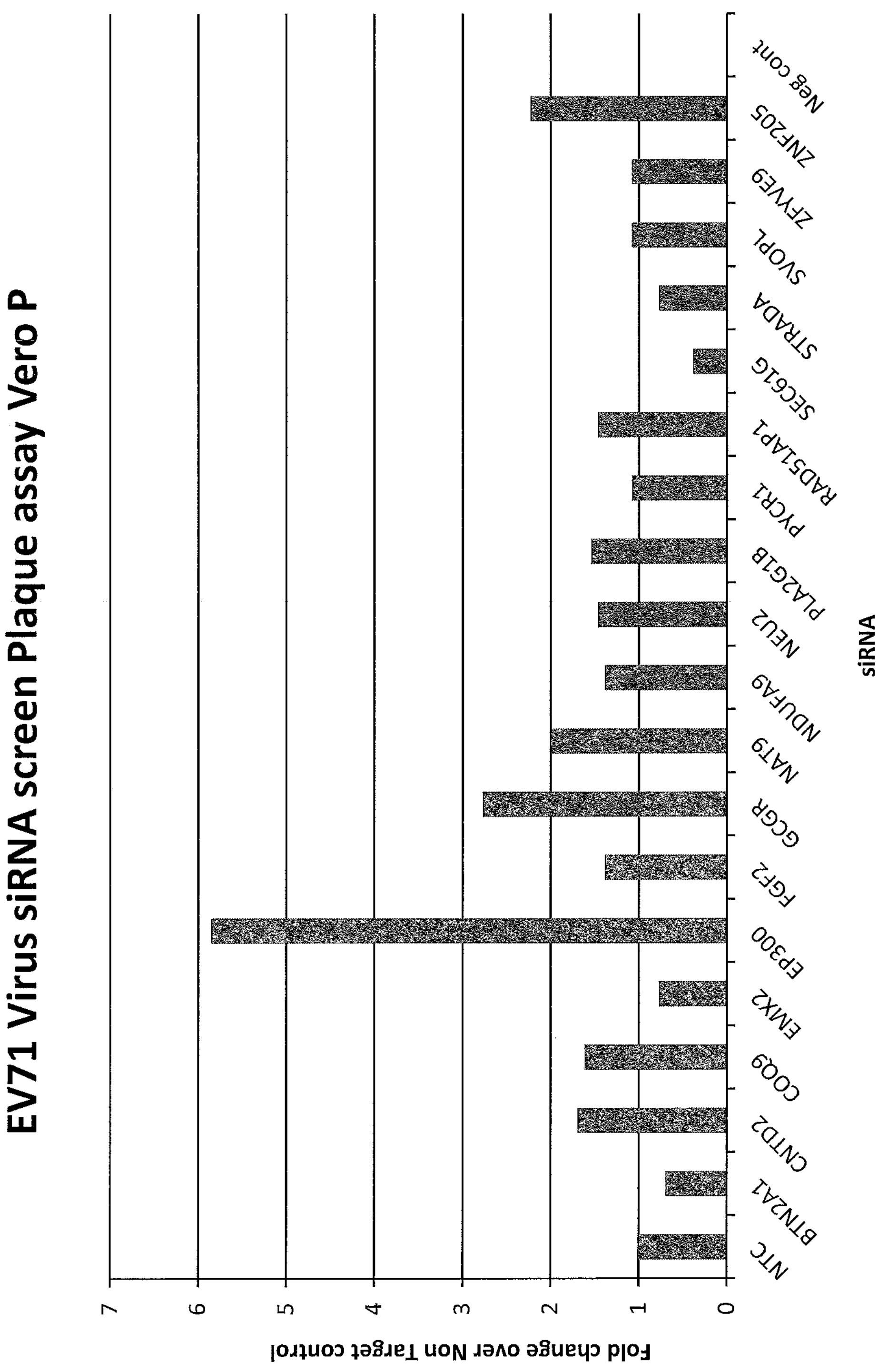
FIGS. 2A and 2B show the effects of host gene knockdown on Enterovirus 71 (EV71) live virus production in HEp-2C and Vero cells.
Figure 2B:
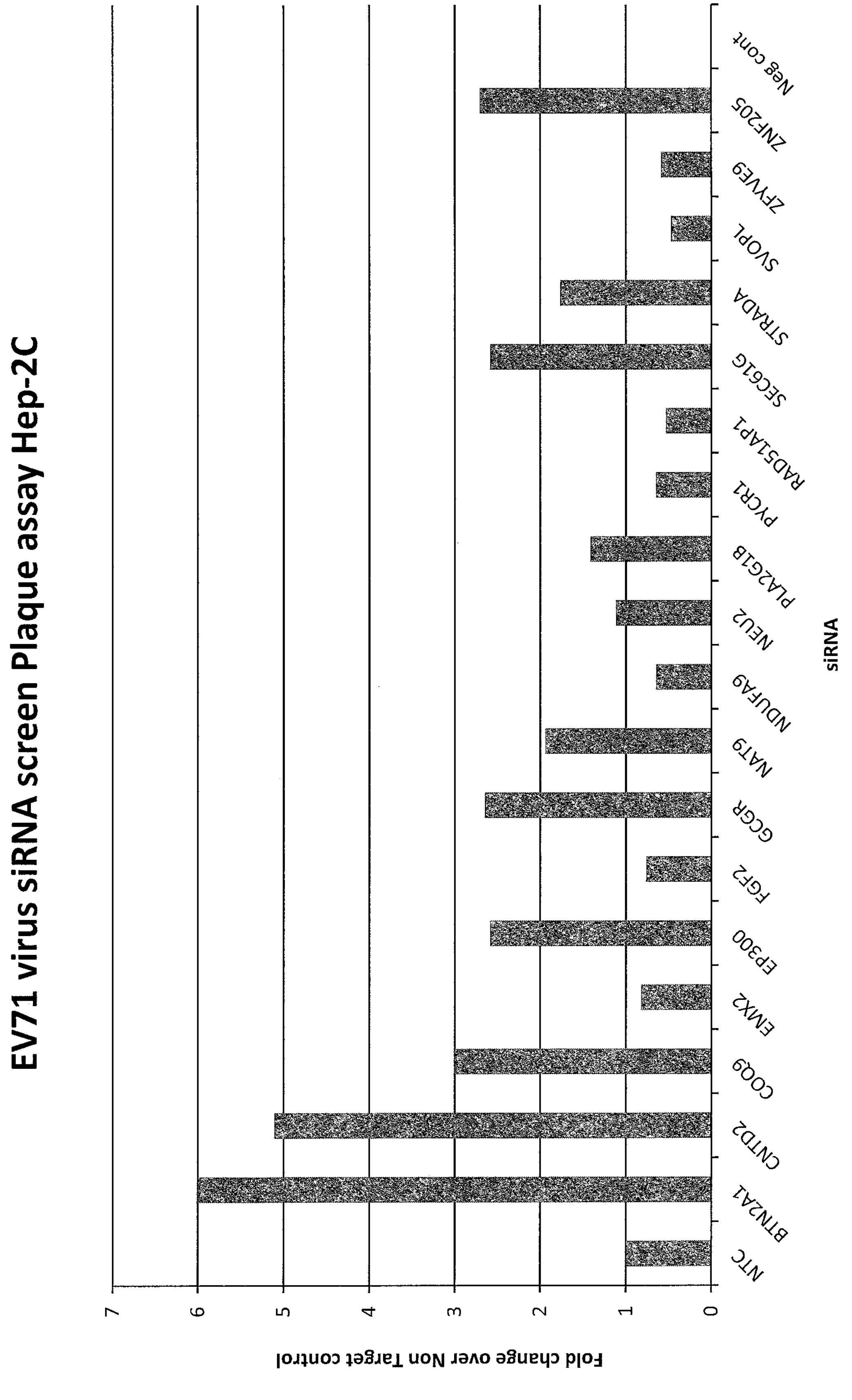
Figure 2C:
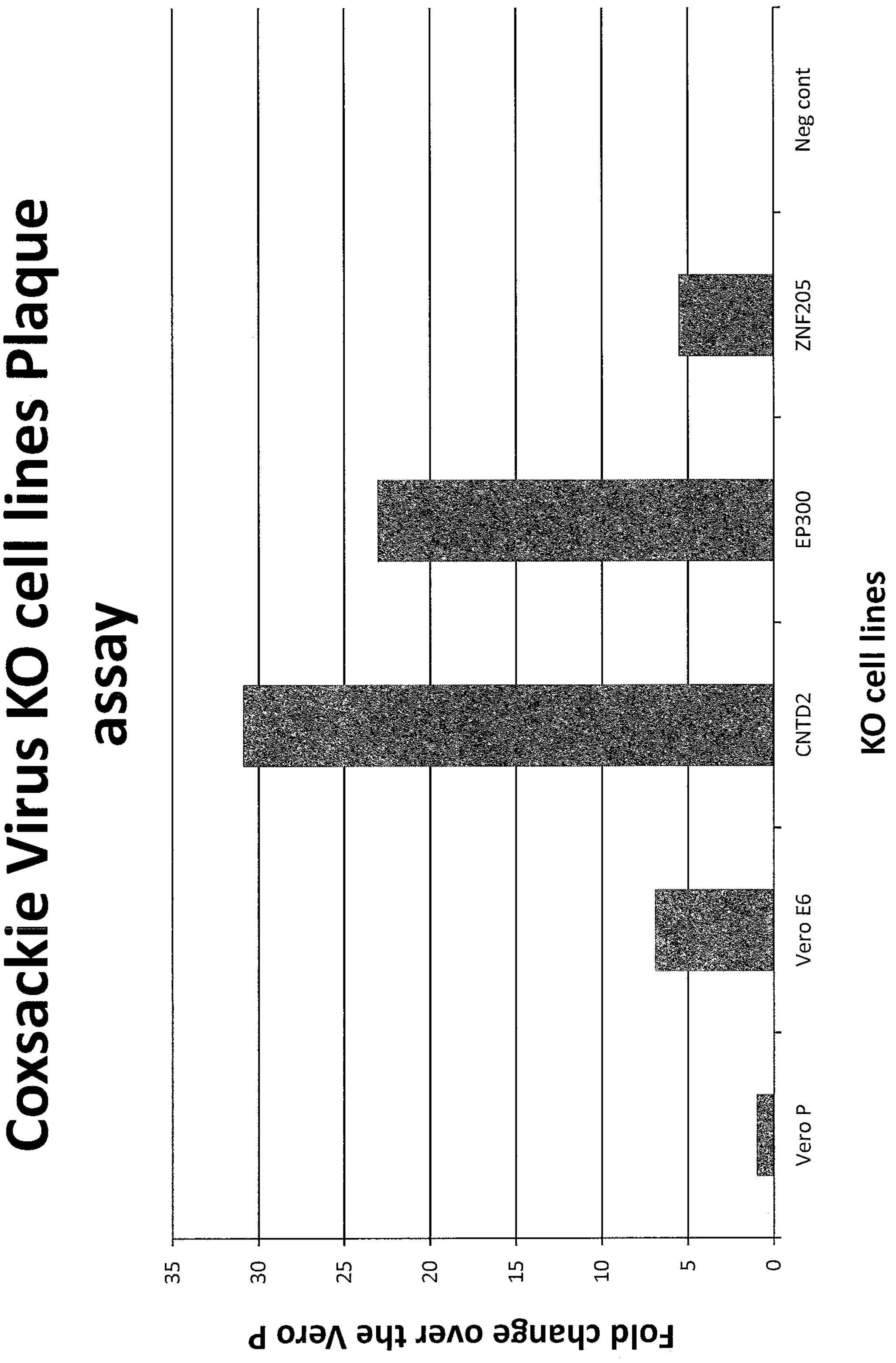
FIG. 2C shows the effects of host gene knockout (using CRISPR technology) on live Coxsackie virus production.

The effects of 18 separate gene knockdown events on coxsackie BSvirus (CV, ATCC VR-185) replication were tested in Vero P and HEp-2C cells. Coxsackie viruses are (+) single stranded RNA viruses belonging to the picornavirus family. As shown in FIG. 2A, a subset of the genes, including but not limited to BTN2A1 and CNTD2 enhanced the production of Coxsackie virus by greater than two-fold in HEp-2C cells. A parallel study of coxsackie virus in Vero P cells showed that knockdown of EP300, and to a lesser extent, GCGR and ZNF205, enhanced virus production in this human cell line. To further understand the contribution of several of these genes to live coxsackie virus production, the ability of CV to replication in Vero cell lines containing homozygous or heterozygous knockouts of three of the genes in this study (CNT2, EP300, and ZNF205) was assessed. Data shown in FIG. 2C show that heterozygous knockout (CNTD2) or complete knockout (EP300 and ZNF205) further enhanced coxsackie B virus titers.

(3) Dengue Virus

Figure 3A:
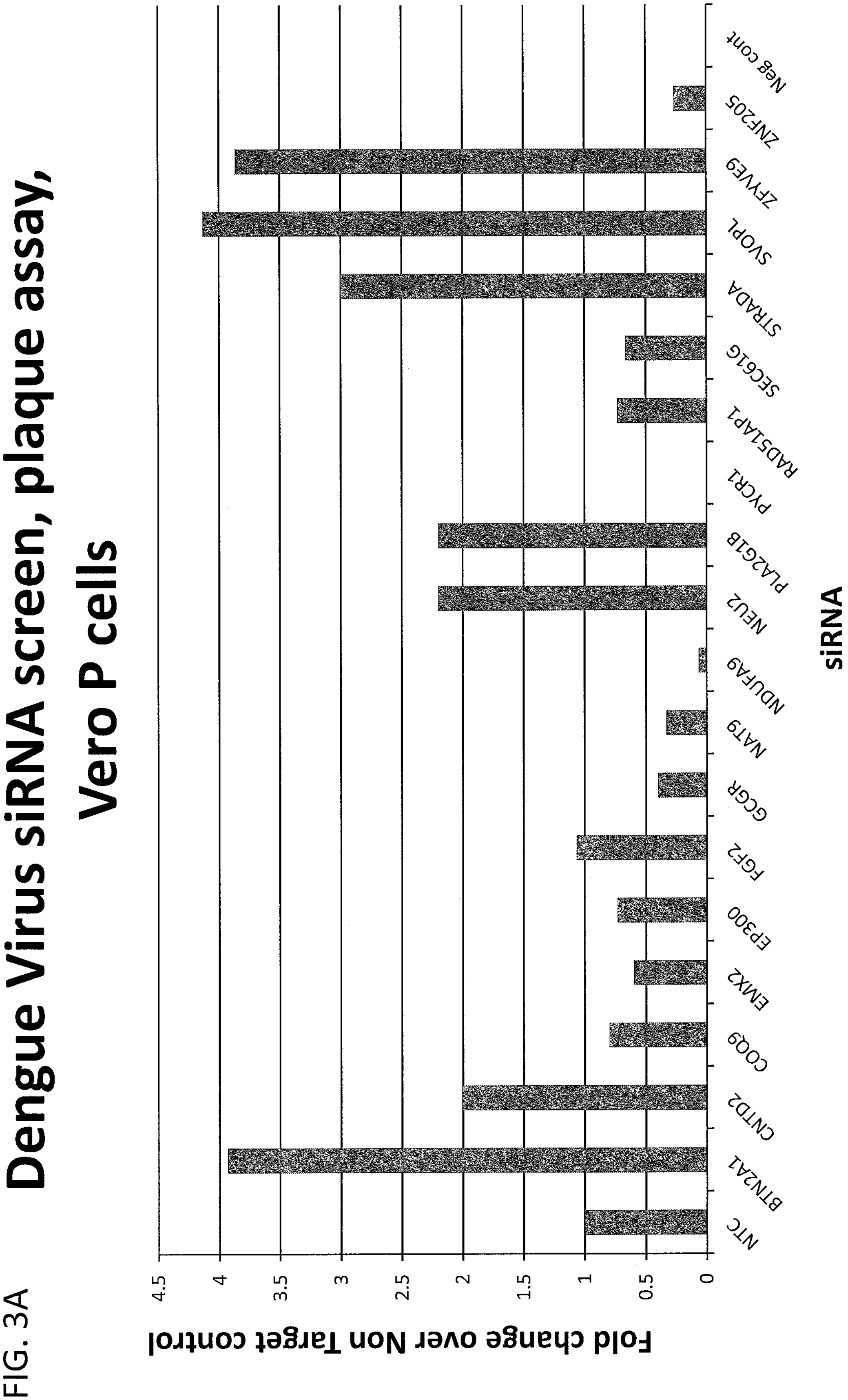
FIGS. 3A and 3B show the effects of host gene knockdown on live Dengue virus production in Vero and HEp-2C cells.
Figure 3B:
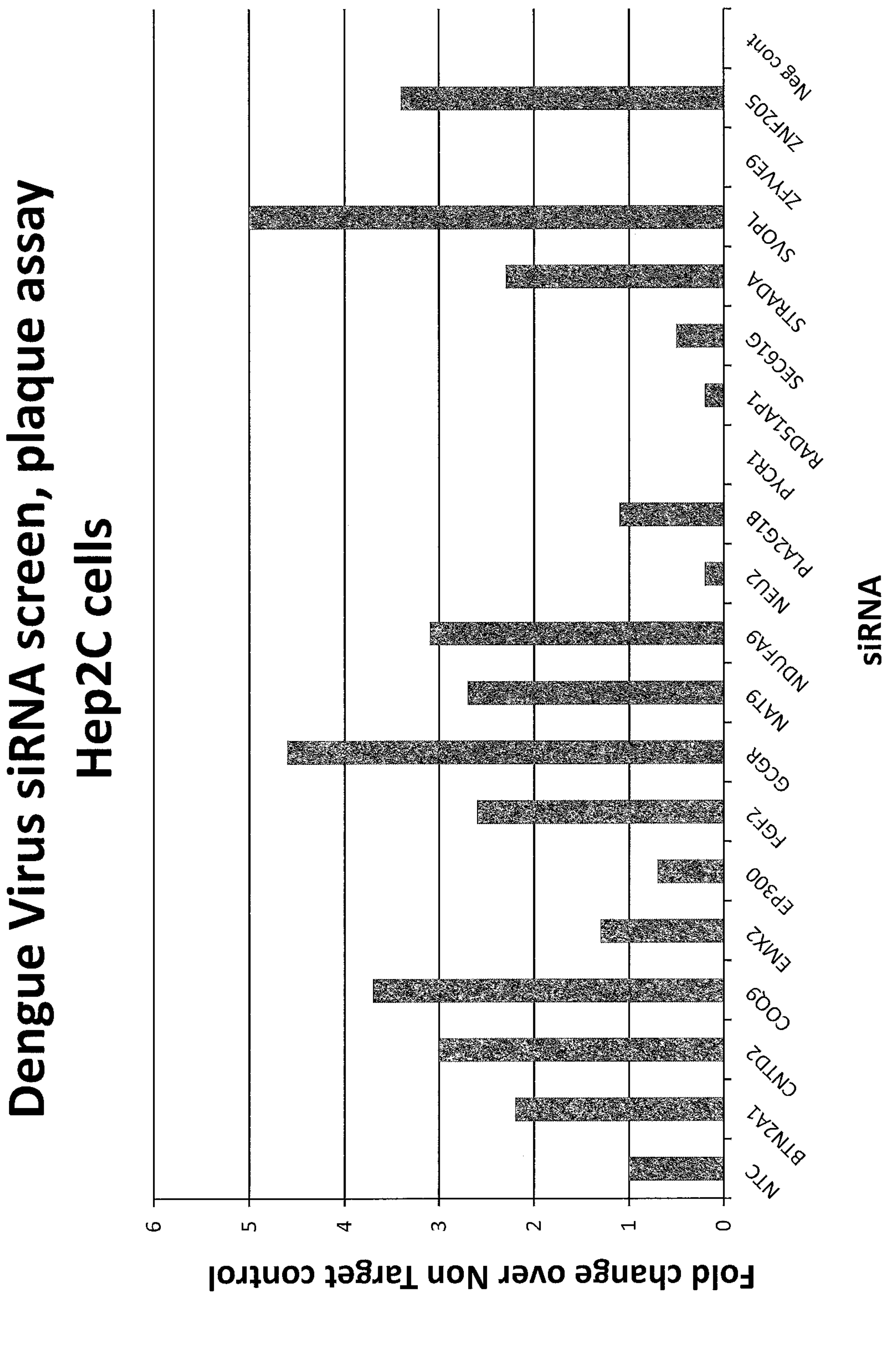

The effects of 18 separate gene knockdown events on Dengue virus Type 1 (DENY, BEI NR-82) titers were assessed using a plaque assay as a means of determining viral titers. FIG. 3A identifies several gene knockdown events including but not limited to BTN2A1, STRADA, SVOPL and ZFYYVE9 that increase live virus titers in Vero cells. FIG. 3B shows how gene silencing in HEp-2C alters Dengue virus titers. COQ9, GCGR, SOVPL, and several other genes greatly enhance live DENY virus production in this human cell line. Two interesting observations can be made from this data set. First, the collection of genes that enhance DENY in Vero and HEp-2C are overlapping, but not identical. Secondly, despite the fact that both DENY and (for instance) Coxsackie virus are both (+) single stranded RNA viruses, the collection genes that enhance the production of DENY are not identical to the genes that enhance CV production. Together, these two observations suggest predicting gene knockdown events that enhance i) individual viruses in different cell lines, and ii) similar viruses in individual cell lines, is not obvious.

(4) Mumps

The Mumps virus is a (−) single stranded RNA virus belonging to the Paramyxoviridae family. The effects of 18 gene knockdown events on Mumps virus (ATCC, VR-365) replication were tested in two cell lines (Vero, Hep-2C).

Figure 4A:
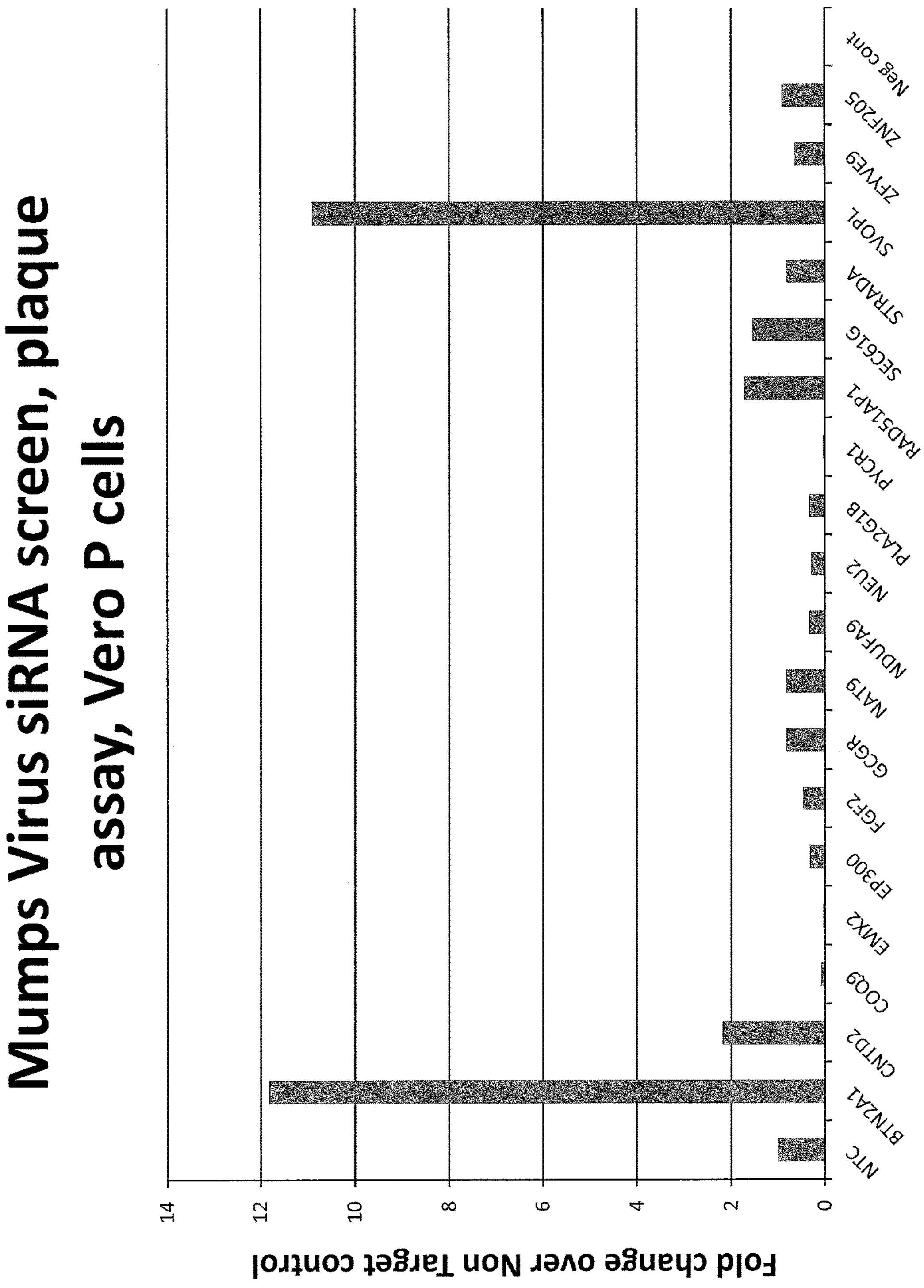
FIGS. 4A and 4B show the effects of host gene knockdown on live Mumps virus production in Vero and HEp-2C cells.
Figure 4B:
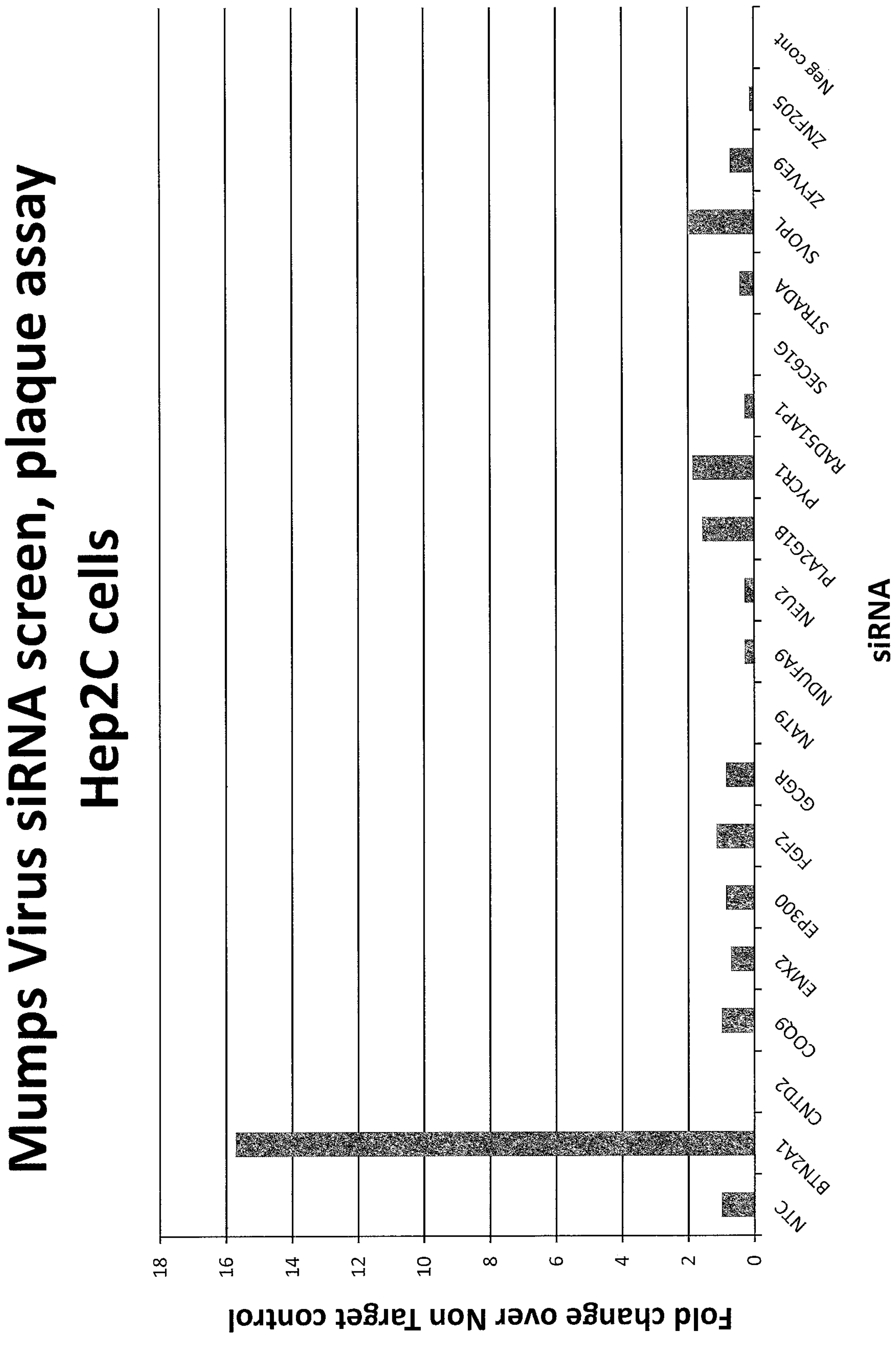

The screen in Vero cells identified 3 genes, BTN2A1, CNTD2, and SVOPL that increased live mumps virus production, ~12×, 2×, and 10× increases, respectively (FIG. 4A). In HEp-2C cells, while silencing of the BTN2A1 gene led to a similar increases in virus production to that which was observed in Vero cells (~15×), CNTD2 and SVOPL increases were less rigorous or not observed at all (FIG. 4B). The observation that i) the genes that enhance mumps virus production differ in the two cell lines, and ii) gene knockdown events that enhance mumps virus are different than those that enhance a second (−) single stranded RNA virus, influenza B, again suggests that predicting gene knockdown events that enhance virus production in any give cell line for any given virus are not obvious.

(5) Yellow Fever

Figure 5A:
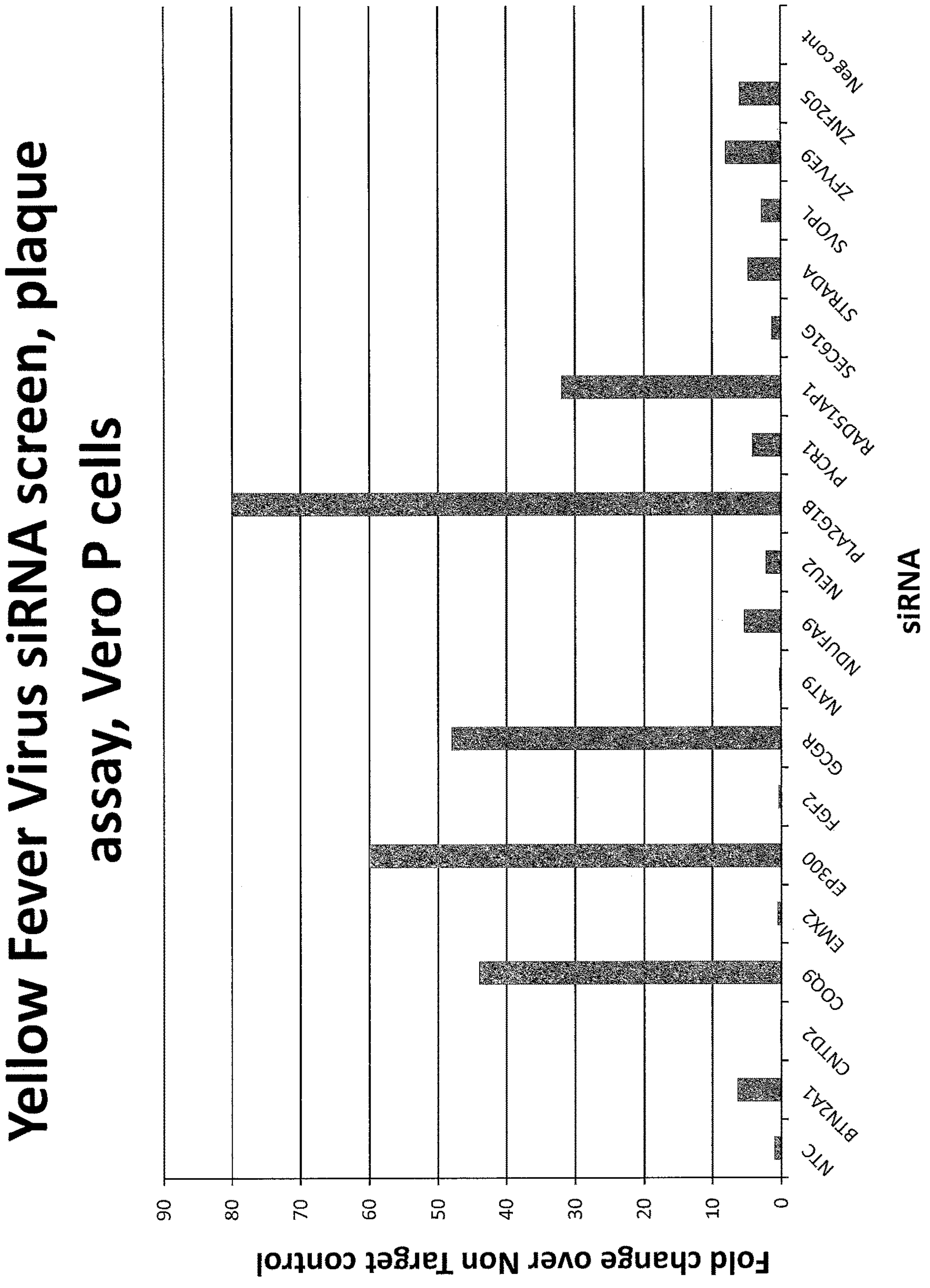
FIGS. 5A and 5B show the effects of host gene knockdown on live Yellow Fever virus production in Vero and HEp-2C cells.
Figure 5B:
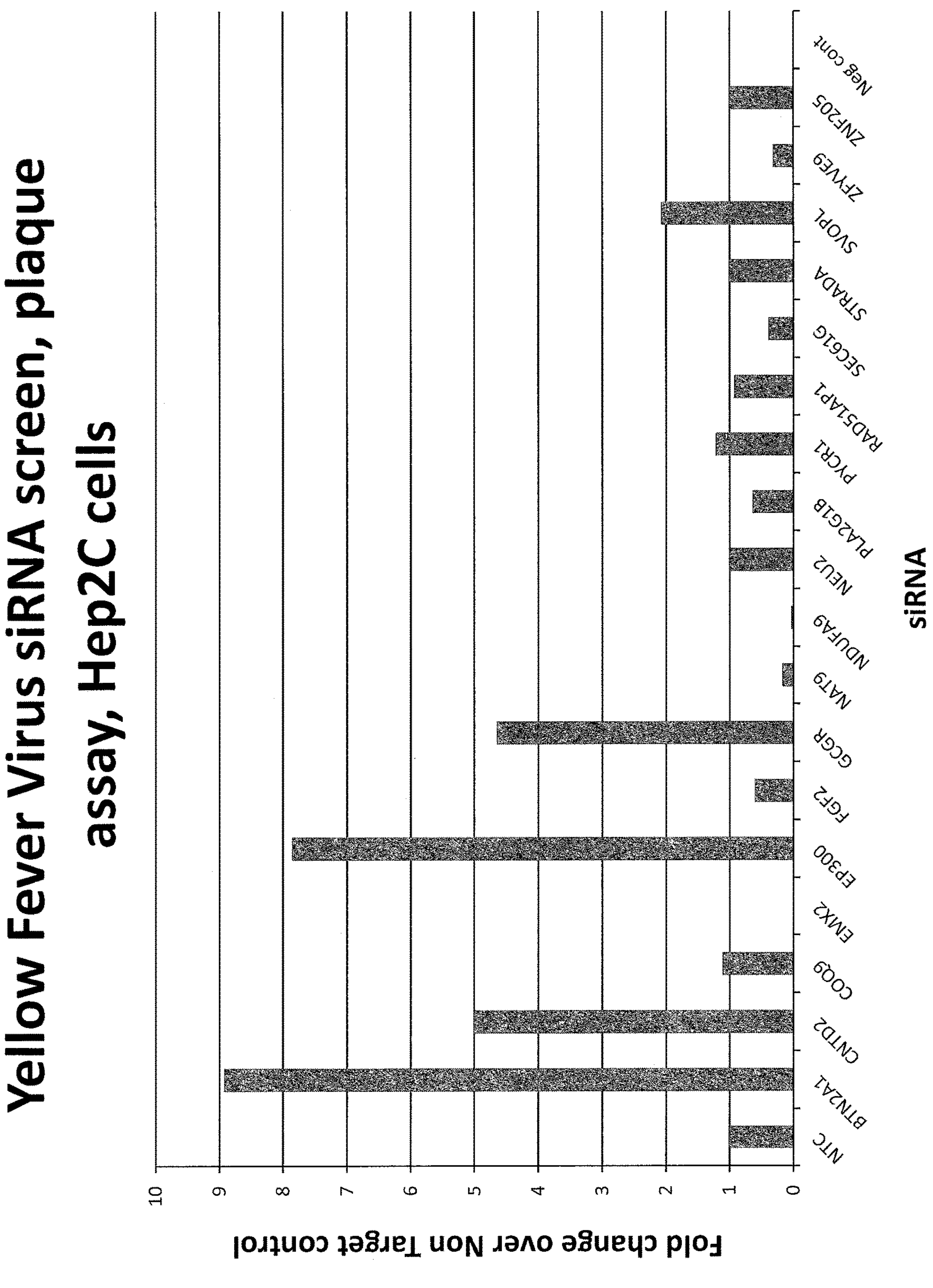

The effects of 18 different gene knockdown events on Yellow Fever virus (YFV, BEI NR-116) were investigated. Yellow fever is a (+) single stranded RNA virus belonging to the Flavivirus family As shown in FIG. 5A, several genes including but not limited to BTN2A1, COQ9, EP300, GCGR, PLA2G1B, and RAD51AP1, significantly increased YFV live virus production. Parallel tests performed in HEp-2C identified a different gene profile (FIG. 5B).

While BTN2A1, EP300, and GCGR similarly enhanced live YFV production, other genes were observed to enhance virus production in the human cell line (e.g., CNTD2, SVOPL).

(6) Hepatitis A

Figure 6A:
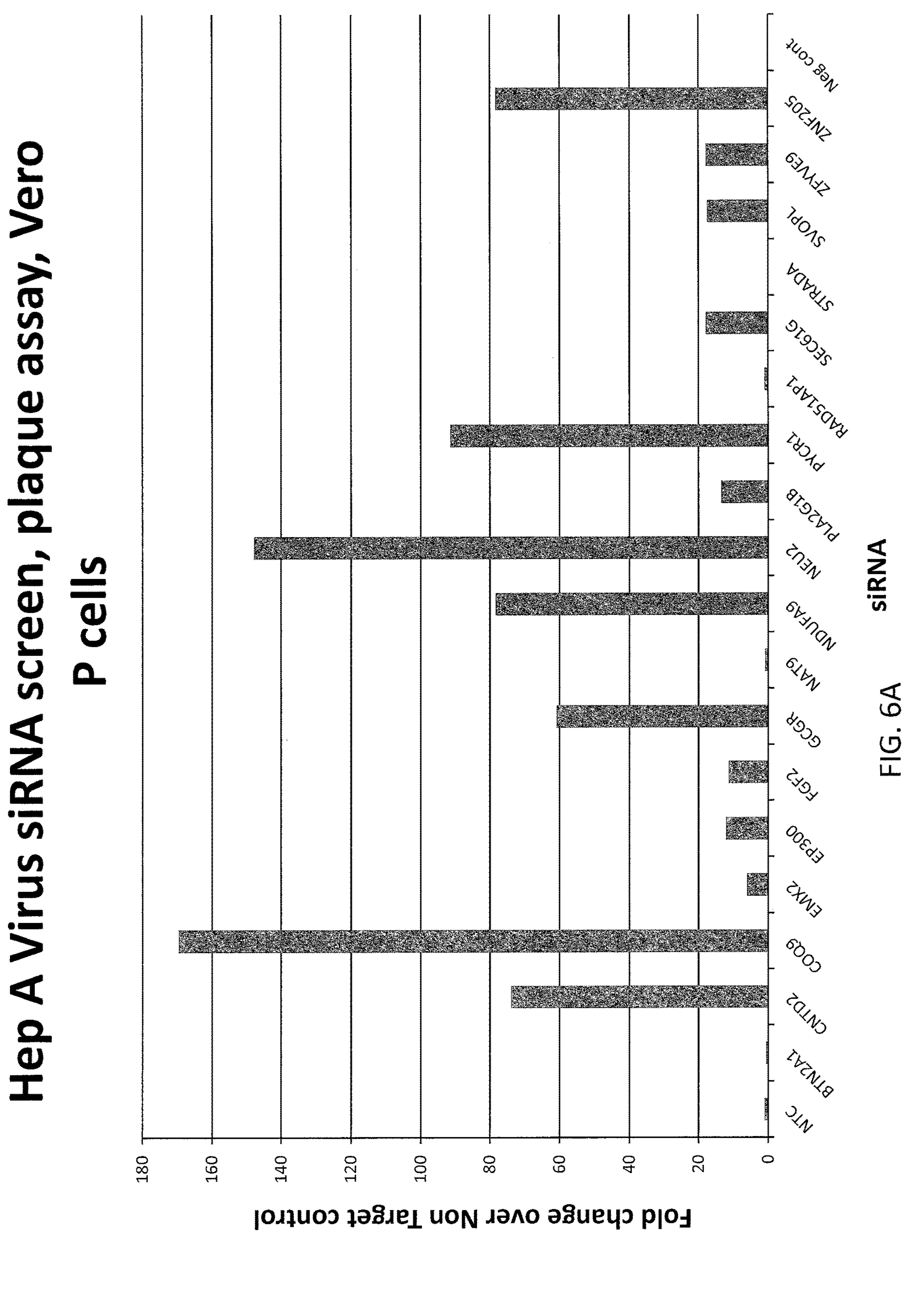
FIGS. 6A and 6B show the effects of host gene knockdown on live Hepatitis A virus production in Vero and HEp-2C cells.
Figure 6B:
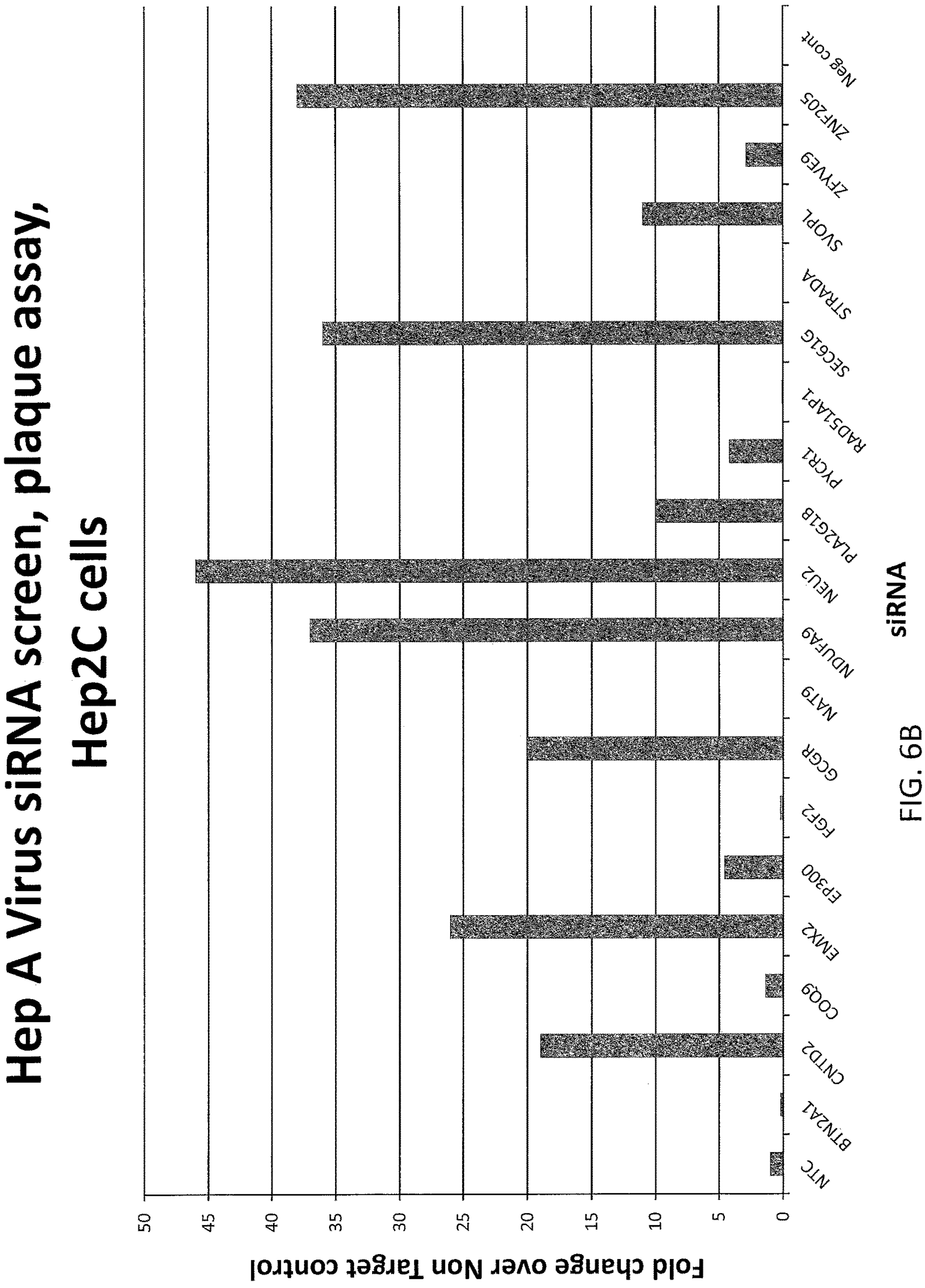

To investigate the effects of gene knockdown on live Hepatitis A (LSH/S, ATCC VR-2266) virus production, a collection of 18 genes were suppressed using siRNA. As shown in FIG. 6A, suppression of several genes including CNTD2, COQ9, GCGR, NDUFA9, NEU2, PYCR1, ZNF205 and others greatly enhanced production of live Hepatitis A production in Vero cells. Parallel studies in HEp-2C cells also identified a collection of genes that can be suppressed to enhance Hepatitis A production (FIG. 6B). It is interesting to note that Hepatitis A, like Coxsackie B5 (EV71), is a (+) single stranded RNA virus belonging to the Picornavirus family Despite the similarities between these two viruses, the profile of genes that enhance live virus production is extremely different. For this reason, making a discovery that a gene or gene combination enhance the production of one virus cannot be extended to a second virus, regardless of how close the similarities between the two pathogens.

(7) Rubella Virus

Rubella virus (RA27/3, ATCC, VR-1359) is (+) single stranded RNA virus belonging to the Togaviridae family. To identify gene knockdown events that enhance Rubella virus production, siRNAs targeting each of the 18 genes under investigation were introduced into Vero or HEp-2C cells. As shown in FIG. 7A, suppression of several genes including CNTD2, NAT9, PYCR1, SVOPL, and ZNF205 enhanced production by greater than 1 log. In contrast, none of the genes under investigation enhance live rubella virus production by greater than 2 fold in HEp-2C cells (FIG. 7B).

(8) Varicella Zoster Virus

Figure 8A:
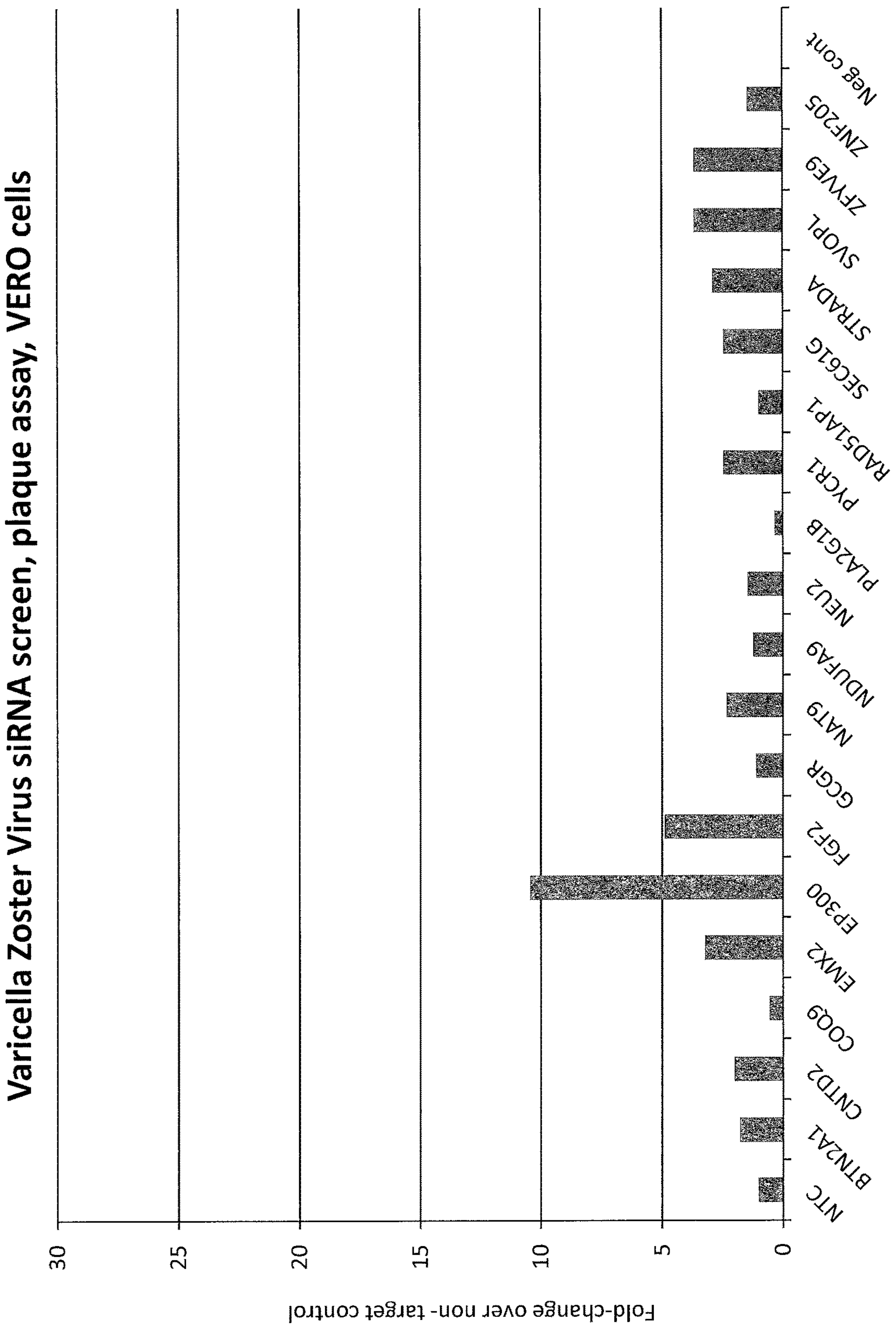
FIGS. 8A and 8B show the effects of host gene knockdown on live Varicella Zoster virus production in HEp-2C cells.
Figure 8B:
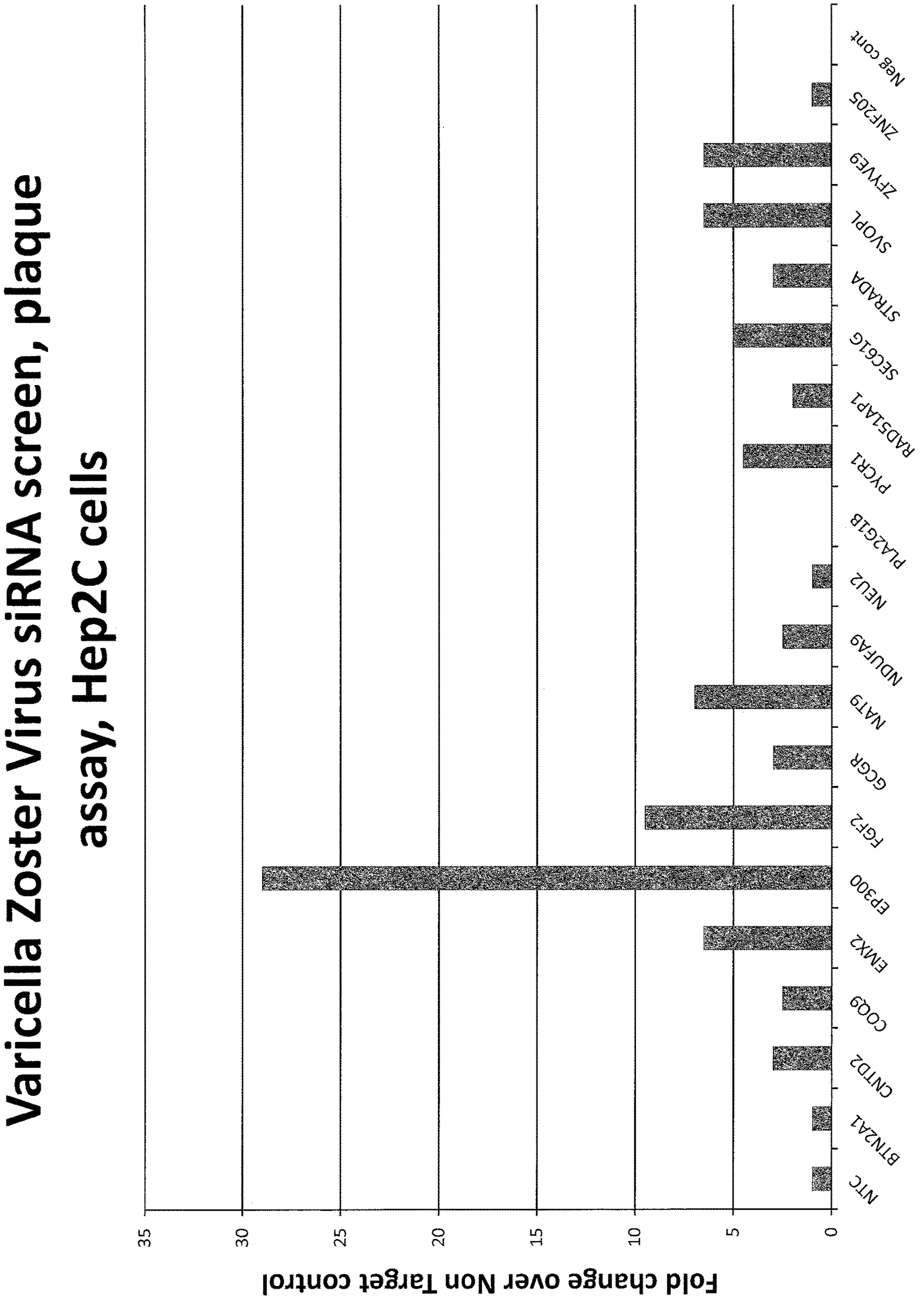

Varicella Zoster Virus (VZV, ATCC VR-1367) is a double stranded DNA virus belonging to the Herpes family. To identify gene suppression events that enhance VZV production in Vero cells, cultures were transfected with siRNAs targeting the genes of interest and subsequently infected with VZV. Surprisingly, VZV failed to grow in Vero cells. To determine if the gene collection could play a role in enhancing live VZV production in a human cell line, siRNAs targeting each of the genes were transfected into HEp-2C cells. Subsequently, cells were infected with VZV. The results of these experiments are shown in FIG. 8. Several genes including (but not limited to) EMX2, EP300, FGF2, and NAT9, significantly enhanced VZV production in HEp-2C.

(9) Zika Virus

Figure 9A:
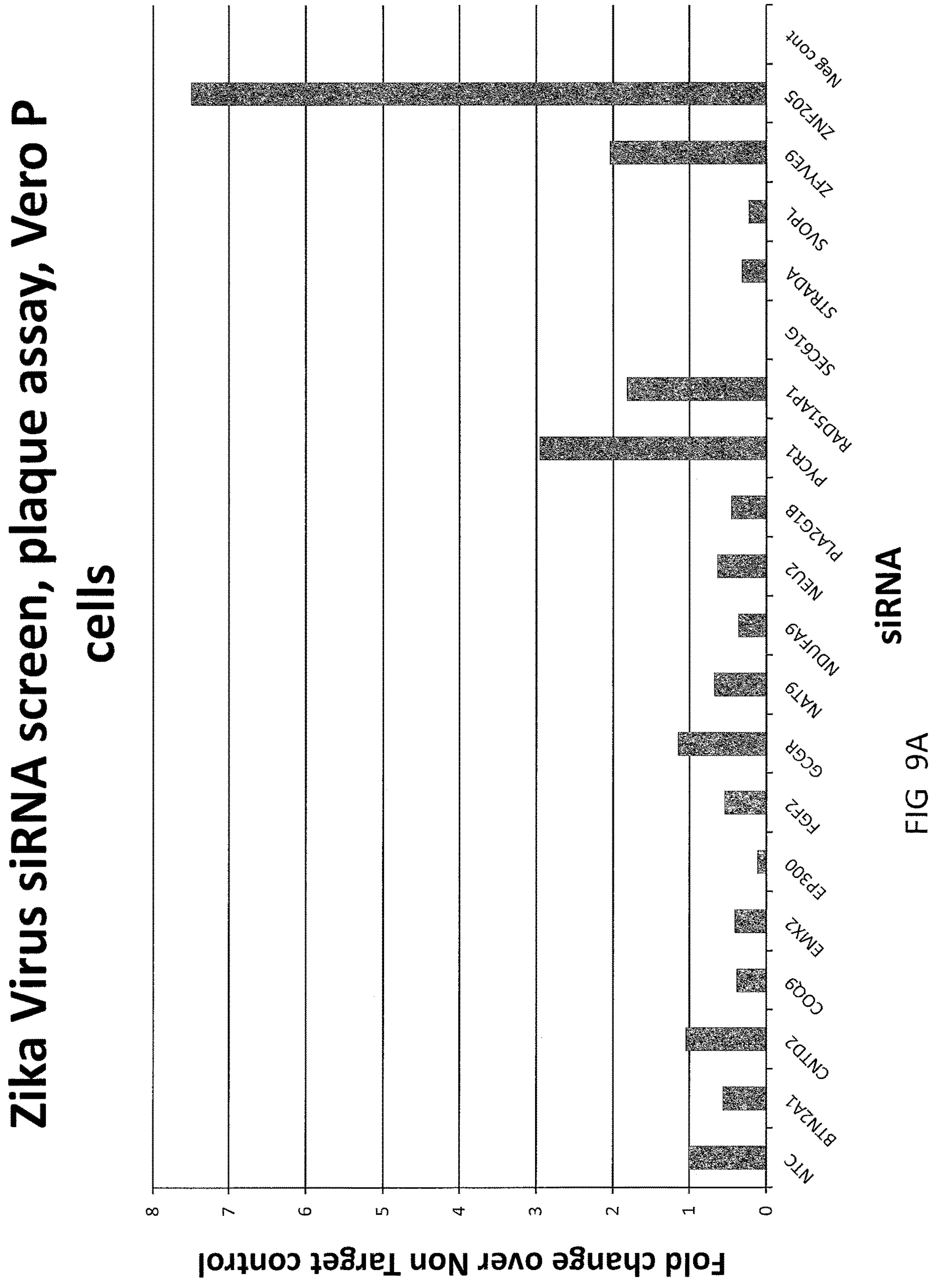
FIG. 9A shows the effects of host gene knockdown on live Zika virus production in Vero and HEp-2C cells.
Figure 9B:
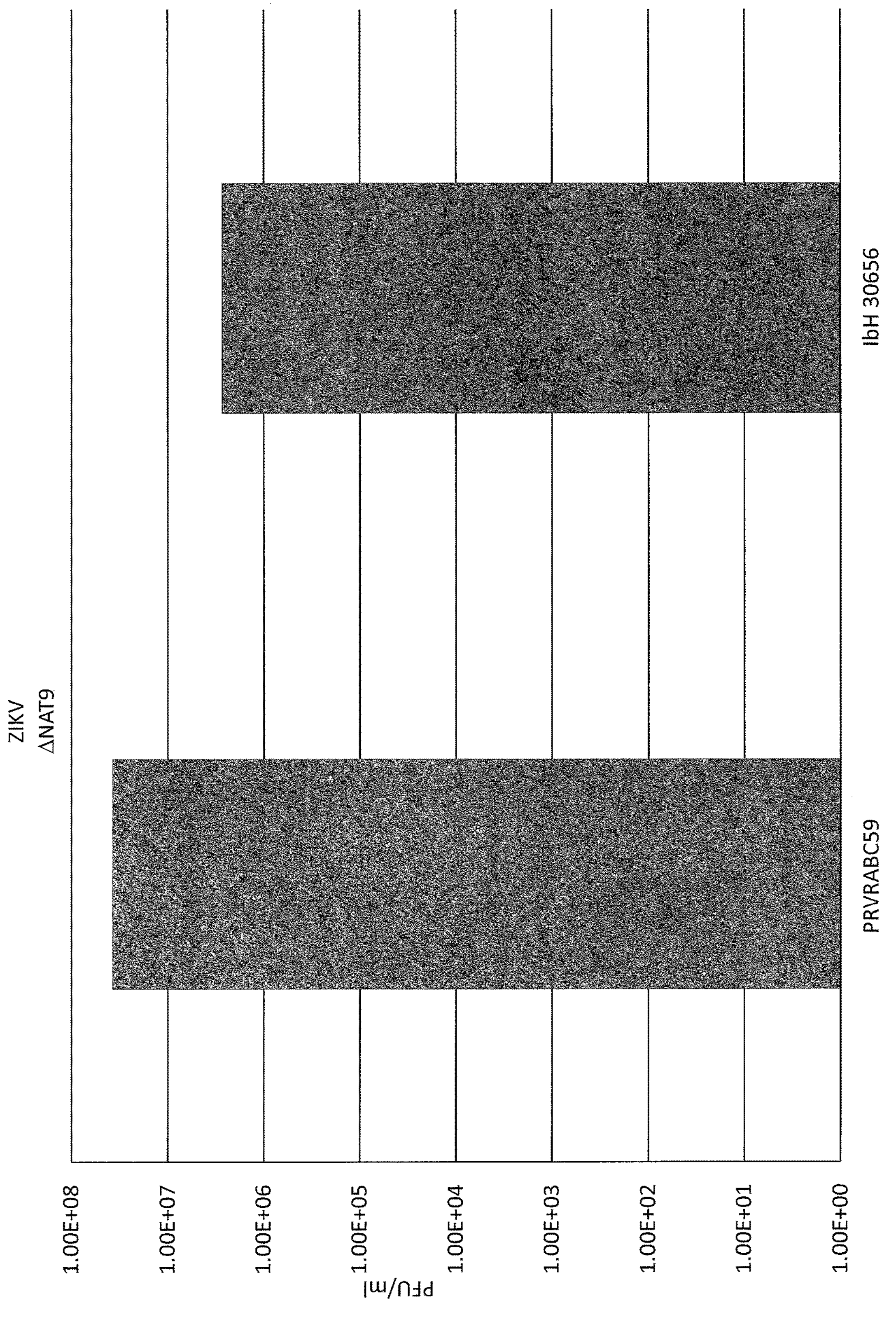
FIG. 9B shows the effects of host gene knockout of NAT9 on live zika virus production in Vero cells.

Like Yellow Fever virus, Zika virus is a (+) single stranded RNA virus belonging to the Flavivirus family. To test the effects of gene knockdown on live ZIKV production, siRNA targeting the genes of choice were introduced into Vero cells. Subsequently, cultures were infected with one of two strains of ZIKV, PRVABC59 or IbH 30656. As shown in FIG. 9A, knockdown of four genes including PYCR1, RAD51AP1, ZFYVE9, and ZNF205 led to increases in PRVABC59 live virus production by ~2-7 fold. Interestingly enough, parallel studies using the IbH 30656 strain of ZIKV showed smaller changes in live virus titer enhancement, suggesting that small changes in the virus can alter the effects of gene knockdown (FIG. 9B). To test the effects of ZNF205 knockout on both strains of ZIKV, a ZNF205 KO Vero cell line was employed in our experimental design using the unmodified parental Vero cell line as a control. As shown in FIG. 9C, elimination of the ZNF205 function greatly enhanced the production of both ZIKV strains.

(10) Adenovirus

The effects of suppressing 18 host genes on Adenovirus (Adenovirus 5) production was investigated in Vero and HEp-2C cells. To achieve this, siRNAs targeting each gene were first introduced into cells followed by infection with the Ad5 virus. To assess the relative titers of Ad5 in supernatants, a Cellomics high content imaging system was employed in conjunction with an immunoassay capable of recognizing Ad5 virus capsid proteins. As shown in FIG. 10A, levels of live Ad5 production were not increased in Vero cells following suppression of any of the host genes in the collection. Parallel studies in HEp-2C similarly failed to identify any gene silencing events that enhanced Ad5 production (FIG. 10B).

TABLE 1

List of genes that when silenced increase virus antigen/virus production. Accession numbers retrieved from PubMed.

| Gene name | Accession No. |
|---|---|
| BTN2A1 | BC016661 |
| CNTD2 | NM_024877 |
| COQ9 | NM_020312 |
| EMX2 | AF301598 |
| EP300 | NM_001429 |
| FGF2 | NM_002006 |
| GCGR | BC112041 |
| NAT9 | NM_015654 |
| NDUFA9 | NM_005002 |
| NEU2 | BC107053 |
| PLA2G1B | NM_000928 |
| PYCR1 | BC022244 |
| RAD51AP1 | NM_001130862 |
| SEC61G | BC051840 |
| STRADA | BC043641 |
| SVOPL | NM_001139456 |
| ZFYVE9 | BC032680 |
| ZNF205 | BC002810 |

Table provides gene symbol and NCIB nucleotide accession number obtained from the NCBI resources database

6. Example 2: Derivation of Universal Mammalian Vaccine Cell Substrates

The Vero cell line is the first continuous mammalian cell line established from African green monkeys in 1962, and is currently the most widely accepted by regulatory authorities for vaccine manufacturing. This is due to the fact that Vero-derived human vaccines have been used for decades, and Vero cells can be grown and infected on micro-carrier beads in large-scale fermentors a with no loss in productivity. In addition to its use as a vaccine cell substrate, this cell line has been used extensively for a variety of virus replication studies and plaque assays. Vero cells are sensitive to infection by many virus such as measles, arboviruses, reoviruses, rubella, polioviruses, influenza viruses, respiratory syncytial viruses, vaccinia, and others. The cell line was submitted to the ATCC at passage level 113 and was propagated to passage level 121 at the ATCC to establish a cell bank. Thus, most vaccine manufacture is performed with cells at passage levels and 130's+ for master and working cell banks for vaccine production. Cells at passage 232 and higher, produced nodules in nude mice when inoculated.

Vero cells were first considered as a cell substrate for vaccine production to manufacture inactivated poliovirus vaccine (IPV), oral (live) poliovirus vaccine, and inactivated rabies vaccine manufactured in Vero cells. The IPV vaccine was licensed in the U.S. in 1990. It is currently the primary IPV used for universal immunization of infants and children in the U.S. ad is the eradication strategy employed by the WHO. Vaccines for polio, measles, mumps, rubella, and more recently rotavirus, HPV, and influenza are currently manufactured using cell cultures. For influenza virus infection, there is a need for maintaining a seasonal vaccine as three to five million cases of severe illness and up to 500,000 deaths occur annually in the States. There are many influenza virus subtypes, typically for vaccines A/H1N1 and A/H3N2 as well as type B influenza can circulate. Within subtypes there can be hundreds or thousands of strains, often grouped in clades, with a degree of similarity. New influenza strains arise by drift or less frequently by reassortment (shift), which is when two different subtypes infect the cell of an animal or human and blend to create a new subtype. The protective capability of currently influenza vaccines is substantially limited.

Viruses are obligate intracellular parasites, and their replication requires host cell functions. One can use this to one's advantage, and although the composition, complexity, and functions of different viruses are different based on the genes encoded by their genomes, all viruses rely on host cell machinery for their replication. Lacking their own translational machinery, viruses must recruit cellular ribosomes to translate viral mRNAs and produce the protein products required for their replication. Also, viruses must get around host innate defenses, and the limited coding capacity of the viral genome needs to be used optimally. By taking advantage of these biological demands one can take advantage of the complex interactions between the virus and host cell, and virus-specific mechanisms and functioning of the cellular protein synthesis apparatus to create a universal vaccine cell line. Viral strategies to dominate the host machinery range from the manipulation of translation factors to modifying the microRNAs that regulate and modify the genome are virus being understood. With the advent of RNA inference (RNAi) technology, one can determine the critical host gene and pathways that are pirated from the hosts and are critically needed for virus replication.

To create an enhanced poliovirus vaccine cell line, the poliovirus-resistance genes in a Vero vaccine cell line were identified using a genome-wide RNA interference (RNAi) screen. Using small interfering RNA technology (siRNA) it is possible to knock-down (KD) host genes affecting virus replication allowing to determine pro- and anti-viral genes. An approach in creating a universal vaccine cell line is to ablate host cell defenses. To create an enhanced vaccine cell line with improved cell tropism, the host-resistance genes to poliovirus (PV), influenza virus (flu) and rotavirus (RV) in Vero cells were identified using siRNAs. Validation of the host genes that modulated poliovirus replication showed that individually or in combination one can increase poliovirus replication by 10-fold to 50-fold without altering poliovirus antigenicity. Once the central host genes needed for virus replication were validated, developed Vero cells were used with clustered regularly interspaced short palindromic repeat (CRISPR)-Cas9 plasmids to permanently knock-out (KO) several individual host genes including and showed that editing these genes in increased viral transcription of PV or RV determined by ELISA.

Given this potential, additional studies involving other RNA and picornaviruses were considered as positive-strand RNA viruses are an important group of human and animal pathogens that have significant global health and economic impacts. Many of the viruses include important Flaviviruses, Alphaviruses, Coronaviruses, and the enteroviruses (poliovirus)—all these viruses have evolved to use common cellular pathways to complete biogenesis. The higher order of shared pathways in host cells and the assembly and function of viral replication complexes is significant and highlights commonalities that can further advance the understanding of virus-host interactions. The Flaviviridae family includes significant global pathogens including Zika virus (ZIKV), Hepatitis C virus (HCV), West Nile virus (WNV), and Dengue virus (DENV). Some of the prominent members of this family include Coxsackie virus (CV), human rhinoviruses (HRV), and the agent of hand-foot-and-mouth disease, Enterovirus 71 (EV71). Members of the Coronaviridae family infect a wide range of mammals and birds causing diseases such as severe acute respiratory syndrome coronavirus (SARS-CoV) and Middle East respiratory syndrome (MERS-CoV). The Togaviridae family includes the genera Rubivirus and Alphavirus. Rubella virus (RUBV) is the sole member in the Rubivirus genus, and the Alphavirus genus contains at least 30 members that are separated into New World and Old World viruses. The New World viruses include Venezuelan equine encephalitis (VEEV), Western equine encephalitis (WEEV) and Eastern equine encephalitis virus (EEEV). Old World alphaviruses include Semliki Forest virus (SFV), and Chikungunya virus (CHIKV).

Based on observations with EV71, where a collection of host virus resistance was identified that upon silencing increased EV71 replication production by >50-fold, several other strains of viruses were examined to determine if the top 6 validated poliovirus siRNAs, the top 6 influenza siRNAs, or the top 6 rotavirus siRNAs (Table 2) could be individually used to screen and then validate host gene that when silenced would increase replication on the viruses. Vero cells and Hep-2 cells were examined as two vaccine cell lines for siRNA transfection. Several RNA viruses were tested including influenza A/WSN/1933 (JAY), poliovirus Sabin-2 (PV2), rotavirus/G3P/BB (RV3), influenza B/Malaysia/2506/2004 (IAB), Dengue virus type 1, Hawaii (DENY), Yellow fever virus 17 D vaccine (YFV), Hepatitis A virus (HAV), Coxsackie virus B5 (EV71), mumps virus (MuV), rubella virus (RUBY), and a DNA virus, Varicella zoster virus (VZV). The results identified several gene KDs that allowed for enhanced viral permissiveness and replication across viral families. Specifically, there were several host genes identified which enhanced virus replication when KD, particularly BTN2A1, CNTD2, EP300, PYCR1, SEC61G, and ZNF205 (Table 4). The findings indicate that KD of one of the 18 genes examined (Table 2) can be used to make a universal cell line.

TABLE 2

Top 6 genes that alter replication of poliovirus (PV), rotavirus (RV) or influenza A virus (IAV).

| Virus | Gene name | Gene symbol |
|---|---|---|
| PV | butyrophilin subfamily 2 member A1 | BTN2A1 |
| | cyclin N-terminal domain containing 2 | CNTD2 |
| | E1A binding | EP300 |
| | glucagon receptor | GCGR |

TABLE 2-continued

| Top 6 genes that alter replication of poliovirus (PV), rotavirus (RV) or influenza A virus (IAV). | | |
|---|---|---|
| Virus | Gene name | Gene symbol |
| | sec61 translocon gamma subunit | SEC61G |
| | zinc finger protein 205 | ZNF205 |
| RV | coenzyme Q9 | COQ9 |
| | N-acetyl transfer 9 (putative) | NAT9 |
| | NADH: Ubiquinone oxidoreductase subunit | NDUFA9 |
| | neuraminidase 2 | NEU2 |
| | synaptic vesicle-2 related protein like | SVOPL |
| | RAD51 associated protein | RAD51AP1 |
| IAV | coenzyme Q9 | COQ9 |
| | NADH: Ubiquinone oxidoreductase subunit | NDUFA9 |
| | phospholipase A2 group 1B | PLA2G1B |
| | pyrroline-5-carboxylate reductase 1 | PYCR1 |
| | zinc finger FYVE-type containing 9 | ZFYVE9 |
| | zinc finger protein 205 | ZNF205 |

The top six genes that were identified from a genome-wide siRNA screen for poliovirus (PV), rotavirus (RV) and influenza A virus (IAV).

a) Results.

The ability to connect systems biology with host gene discovery to aid the understanding of the virus-host network is essential for creating a universal vaccine cell line. Complementary approaches and data sets from several high-throughput screens were used for IAV, PV, and RV to arrive at a multidimensional view of virus-host networks. The 6 top host genes that enhanced virus replication important for PV, RV or IAV (18 genes total) were screened and tested to determine if gene KD using siRNAs in Vero cells or HEp-2 cell lines would affect host cell permissiveness and allow for enhanced virus replication compared to control WT cells or cells transfected with a non-targeting (NTC) control siRNA. All data is expressed from n>3 experiments and based on fold-increase from NTC. All siRNAs tested were ON-TARGETplus siRNAs designed to be seed-region optimized, leading to minimal off-target effects. The genome-wide screens for PV, IAV and RV showed no or negligible off-target effects. All host genes targeted for KD in Vero cells or HEp-2 cells were >90% silenced before virus infection (Table 3).

TABLE 3 qRT-PCR validation of siRNA-mediated gene KD in Vero cells.

| | Percent expression | | | | |
|---|---|---|---|---|---|
| | NTC | | siRNA treatment | | |
| | Replicate 1 | Replicate 2 | Replicate 1 | Replicate 2 | Adjusted P Value |
| BTN2A1 | 100.00 | 100.00 | 0.03 | 0.03 | <0.0001 |
| CNTD2 | 100.00 | 100.00 | 0.00 | 0.04 | <0.0001 |
| COQ9 | 100.00 | 100.00 | 0.00 | 2.37 | <0.0001 |
| EMX2 | 100.00 | 100.00 | 0.00 | 1.57 | <0.0001 |
| EP300 | 100.00 | 100.00 | 0.00 | 0.86 | <0.0001 |
| FGF2 | 100.00 | 100.00 | 0.00 | 3.67 | <0.0001 |
| GCGR | 100.00 | 100.00 | 0.11 | 0.05 | <0.0001 |
| NAT9 | 100.00 | 100.00 | 0.00 | 1.08 | <0.0001 |
| NDUFA9 | 100.00 | 100.00 | 0.00 | 0.88 | <0.0001 |
| NEU2 | 100.00 | 100.00 | 0.00 | 0.00 | <0.0001 |
| PLA2G1B | 100.00 | 100.00 | 0.00 | 0.00 | <0.0001 |
| PYCR1 | 100.00 | 100.00 | 0.00 | 0.01 | <0.0001 |
| RAD51AP1 | 100.00 | 100.00 | 0.00 | 0.00 | <0.0001 |
| SEC61G | 100.00 | 100.00 | 0.00 | 0.02 | <0.0001 |
| STRADA | 100.00 | 100.00 | 0.00 | 0.00 | <0.0001 |
| SVOPL | 100.00 | 100.00 | 0.00 | 0.00 | <0.0001 |
| ZFYVE9 | 100.00 | 100.00 | 0.00 | 0.00 | <0.0001 |
| ZNF205 | 100.00 | 100.00 | 0.00 | 0.02 | <0.0001 |

Vero cells were transfected with siRNAs against listed genes (50 nM). Total RNA was isolated and treated with DNAse I to remove genomic DNA, reverse transcribed using oligo dT, and expression determined relative to GAPDH using custom Vero-specific primers for each gene. Amplification conditions were optimized as needed and amplicons were validated via Sanger sequencing.

BTN2A1-butyrophilin subfamily 2 member A1;

CNTD2-cyclin N-terminal domain containing 2;

COQ9—coenzyme Q9;

EMX2-empty spiracles homeobox 2;

EP300-E1A binding protein;

FGF2—fibroblast growth factor 2;

GCGR-glucagon receptor;

NAT9—N-acetyl transferase 9 (putative);

NEU2—Neuraminidase 2;

PLA2G1B—phospholipase A2 group IB;

PYCR1-pyrroline-5-carboxylate reductase 1;

RAD51AP1-RAD51 associated protein 1;

SEC61G-SEC61 translocon gamma subunit;

SVOPL—SVOP like protein;

ZFYVE9-zinc finger

FYVE-type containing 9;

ZNF205-Zinc finger protein 205.

Gene expression is shown as percent.

All comparisons were done using 2-way ANOVA and post hoc-Sidak test at $\alpha = 0.05$.

For these studies, the PV strain was Sabin-2 as the World Health Organization recently endorsed elimination of Sabine-1 strains. Virus strain differences were noted in the magnitude of PV replication while switching from Sabin-1 to Sabin-2, particularly in the use of host genes involved in the ability of these strains to replicate. In Vero cells, the highest PV replication resulted from KD of CNTD2 (~7-fold) followed by KD of BTN2A1 (~5-fold), and EP300, GCGR, NAT9, RAD51AP1, SEC61G and ZNF205 that ranged from >3-4-fold increases (FIG. 10A). In HEp-2 cells, the highest PV replication occurred for KD of CNTD2 (3-fold), where BTN2A1, EP300, GCGR, and ZNF205 KD resulted in >2-3-fold increases. The ELISA results (OD) were examined for Sabine-2 (FIG. 10A) and for rotavirus/G3P/BB (RV) infection in Vero cells (FIG. 10B). An ELISA was necessary since RV does not plaque well in Vero cells, and the ELISA results for Sabin-2 are a comparator with respect to the plaque assay results. The top 6 genes were also evaluated for IAV replication in Vero cells (FIG. 10C). IAVs are divided into subtypes based on two proteins on the surface of the virus: the hemagglutinin (H) and the neuraminidase (N). There are 18 different hemagglutinin subtypes and 11 different neuraminidase subtypes. The top genes identified that when KD increased IAV replication were PLA2G1B and PYCR1 (~3-4-fold) followed by ZFYVE9, NDUFA9, COQ9 and ZNF205 (~2-3-fold).

Viruses from 5 RNA virus families (Picornaviridae, Flaviviridae, Togaviridae, Orthomyxoviridae, Reoviridae, Paramyxoviridae) and 1 DNA virus family, i.e. Herpesviridae were examined in efforts to develop a universal cell line. All of these viruses were tested in Vero cell and HEp-2 cell lines that were targeted by siRNA to KD the top 18 gene hits (Tables 1 and 2). EV71 is a picornavirus and was propagated in Vero cells (FIG. 2A) and in HEp-2 cells (FIG. 2B). In Vero cells, there was a ~6-fold increase in virus replication following KD of host gene EP300. As the results are expressed as fold-change over NTC, any >2-fold increase in replication was considered notable. Other important host genes affecting EV71 replication were GCGR, NAT9 and ZNF205 (FIG. 2A). For HEp-2 cells, KD of BTN2A1, CNTD2 and COQ9 increased EV71 virus replication 3-6 fold, while there was a 2-3-fold increase when COQ9, EP300, GCGR, NAT9, SEC61G and ZNF205 were KD. Little is known about how these host genes affect EV71 replication. KD of more than one gene can have synergistic or additive effects. The EP300 gene behaves as a histone acetyltransferase and regulates transcription. The glucagon receptor gene (GCGR) has a role in glucose homeostasis and is implicated to modulate the activity of adenylate cyclase. The N-acetyltransferase 9 (NAT9) gene is involved in the catalysis of the transfer of an acetyl group to a nitrogen atom on the acceptor molecule. There is experimental evidence at the protein level that zinc finger protein (ZNF)-205 may be involved in transcriptional regulation. For HEp-2 cells (FIG. 2B), KD of BTN2A1, CNTD2 and COQ9 had a 3-6-fold increase in EV71 replication. Butyrophilin subfamily 2 member A1 (BTN2A1) is important in lipid metabolic processes, and can increase vesicle release as a result of decreased endosomal fusion with the plasma membrane. The cyclin N-terminal domain-containing protein 2 (CNTD2) is annotated at the transcript level, and little is known about the gene. There is some evidence that the ubiquinone biosynthesis protein (COQ9), functions as a lipid-binding protein involved in the biosynthesis of coenzyme Q, which is an essential electron transporter for cellular respiration. Protein transport protein Sec61 subunit gamma (SEC61G) can function to aid protein translocation in the endoplasmic reticulum.

HAV viruses are in the picornavirus family HAV replicated to high levels in Vero cells (FIG. 6A), and to elevated levels in HEp-2 cells (FIG. 6B). KD of COQ9 and NEU2 genes in Vero cells led to 140-160-fold increases in replication. Other notable host genes in Vero cells were CNTD2, GCGR, NDUFA9, PYCR1, and ZNF205 where KD of these genes increased replication from 60-90-fold (FIG. 6A). The genes are discussed above, and determined to be important for replication in HEp-2 cells (FIG. 6B). KD of NDUFA9, NEU2, SEC61G, and ZNF205 led to 35-45-fold increase in HAV replication. Of note, the NADH dehydrogenase 1 alpha subcomplex subunit 9 (NDUFA9) gene affected replication in both Vero cells and Hep-2 cells. This gene is thought to be an accessory subunit of the mitochondrial membrane respiratory chain NADH dehydrogenase. The NEU2 gene catalyzes the removal of sialic acid from glycoproteins and oligosaccharides. It is not clear how these host genes affect HAV replication.

Dengue virus (DENY), a member of the Flaviviridae family, is transmitted by *Aedes* mosquitos. Based on antibody neutralization, four serotypes (DENY-1, DENY-2, DENV-3, and DENY-4) are evident. KD of 7 of 18 top genes in Vero cells (FIG. 3A), and 10 of 18 top genes in HEp-2 cells (FIG. 3B) led to increased replication following infection with DENY-1. Both Vero cells and Hep-2 cells were similarly permissive, and there was a 2-4 fold increase in virus replication with KD of BTN2A1, CNTD2, NEU2, STRADA, SVOPL, or ZFYVE9 genes. KD of SVOPL increased DENY-1 replication 4-5-fold. For HEp-2 cells, enhanced replication was >2-fold for KD of BTN2A1, CNTD2, COQ9, FGF2, GCGR, NAT9, NDUFA9, STRADA or ZNF205. These host genes have no known role affecting DENY-1 replication, and further, the SVOPL gene is poorly annotated and thought to function as a substrate-specific transmembrane transporter.

Yellow fever virus (YFV) is transmitted to humans by *Aedes* mosquitos. As expected, IFN-deficient Vero cells were more susceptible and had >10× higher virus replication compared to HEp-2 cells. KD of COQ9, EP300, GCGR, PLA2G1B or RAD51AP1 resulted in enhanced YFV replication (>30-80-fold) in Vero cells (FIG. 5A). KD of PL2G1B had the greatest effect on virus replication, approximately 80-fold over NTC, while KD of BTN2A1, CNTD2, EP300 GCGR and SVOPL had to a 2-9-fold increase in YFV replication (FIG. 5B). As noted, YFV replication in HEp-2 cells was diminished relative to Vero cells, with peak titers following KD or BTN2A1 ~9-fold, followed by EP300 (~8-fold), and CNTD2 and GCGR at 4-5-fold increases in virus replication. Most gene functions as they relate to virus replication remain unknown.

Mumps virus (MuV) is typically propagated in Hep-2 cells as it does not grow well in Vero cells. The permissiveness of MuV was examined for Vero cells and HEp-2 cells having KD of select host genes (Table 2). KD of BTN2A1 and SVOPL dramatically increased MuV propagation in Vero cells (FIG. 4A), whereas only KD of BTN2A1 was associated with enhanced virus replication in HEp-2 cells (FIG. 4B). KD of BTN2A1 led to increased MuV replication from 11-15-fold in Vero cells and HEp-2 cells, respectively. SVOPL KD also enhanced MuV replication 10-11-fold in Vero cells (FIG. 4A), but had no detectable effect on replication in HEp-2 cells (FIG. 4B). CNTD2 was important in MuV replication in Vero cells where there was a 2-fold increase in replication. KD of BTN2A1 or SVPOL genes enhanced MuV replication, but the mechanism remains unknown.

Varicella zoster (VZV) is the causative agent of chickenpox/shingles and is a DNA virus and member of a-herpesvirus family. VZV is a component of several vaccines including the combined measles, mumps, rubella, and varicella (MMRV) vaccine, and newer vaccines such as live-attenuated herpes zoster vaccine for adults >50 years. Hep-2 cells (FIG. 8B) were superior to Vero cells (FIG. 8A) for propagating VZV, where there was ~30-fold increase in VZV replication, in particular following EP300 KD. One of the reported functions for EP300 is its positive regulation of sequence-specific DNA binding transcription factor activity.

Figure 7:
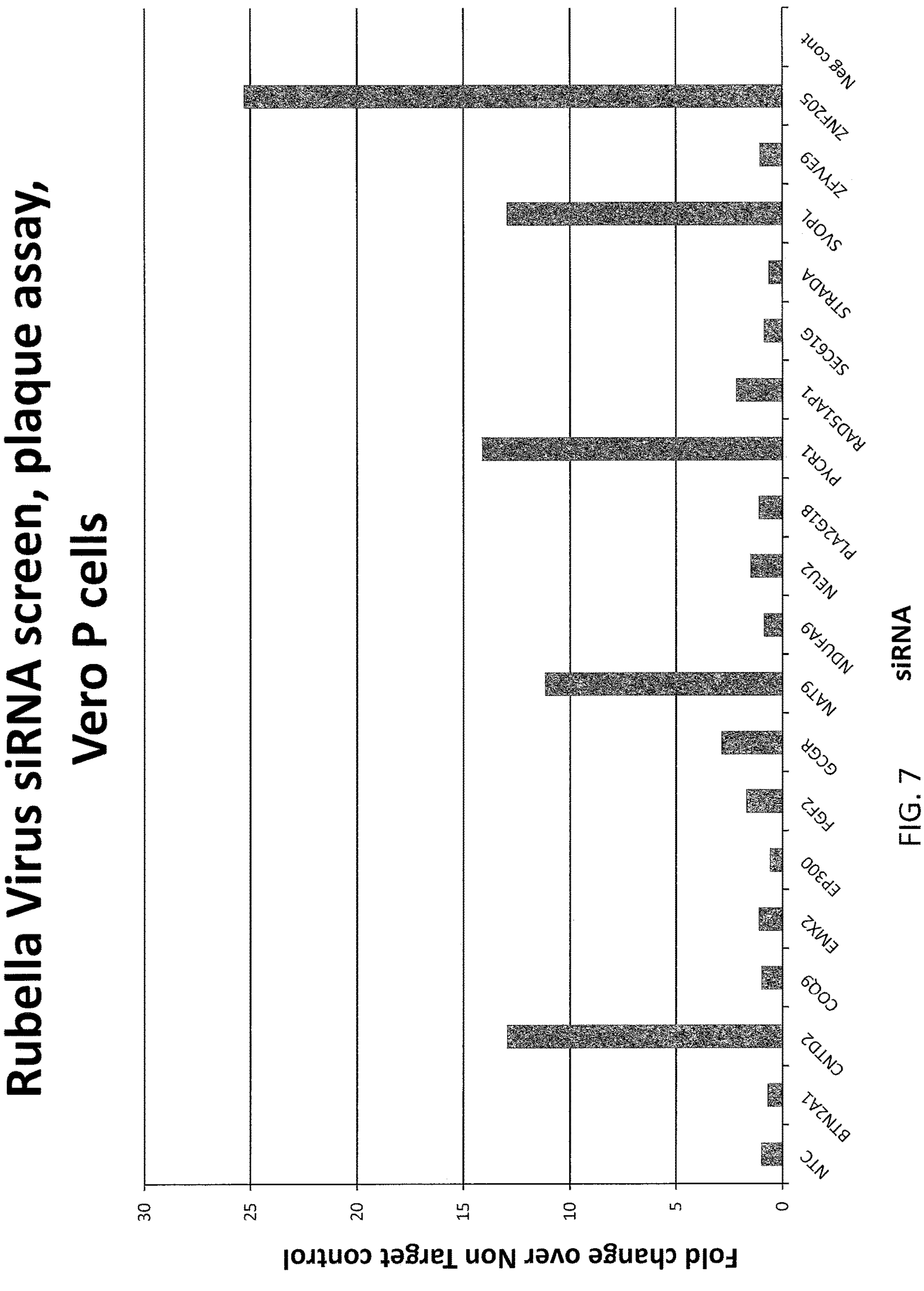
FIG. 7 shows the effects of host gene knockdown on live Rubella virus production in Vero and HEp-2C cells.

Rubella virus (RUB V) is in the family Togaviridae. RUBV is an important human pathogen associated with it birth defects, known congenital rubella syndrome (CRS), but through use of vaccines rubella and CRS are controlled. Whether RUBY would grow in Vero cells (FIG. 7). KD of CTND2, NAT9, PYCR1, or SVOPL led to 10-15-fold increases in RUBY titer, except for KD of host gene ZNF205, which led 25-fold enhanced titer over wild type Vero cells.

There are four types of flu viruses, A, B, C and D, where human flu A and B viruses cause seasonal epidemics and flu type C infections generally cause a mild respiratory illness, and flu type D viruses primarily affect cattle and are not known to infect or cause illness in people. Currently, two lineages of type B influenza virus (IAB) co-circulate in the world, thus the key host genes that affect IAB replication were determined in Vero cells which are an FDA-approved vaccine cell line used to propagate flu viruses. KD of BTN2A1, COQ9, EP300, FGF2, GCGR, and NAT9 genes had a ~2-3-fold increased IAB replication (FIG. 11). These data show that virus types and strain differences occur in and between host cell types in the responses to replication.

Lastly, Zika virus (ZIKV) which belongs to the Flaviviridae family and is spread by mosquitoes, was evaluated for replication in Vero cells and HEp-2 cells. Two ZIKV strains, PVRABC59 and lbH30656 (FIG. 9), were tested, but ZIKV strains only grew in Vero cells, which is consistent with their IFN-sensitivity in HEp-2 cells. In Vero cells, KD of ZNF205 lead to a ~7-fold increase in ZIKV virus titers, though there was a nearly 3-fold increase in virus titer following PYCR1 KD. The role for PYCR1 or ZNF205 on restricting virus ZIKV replication is not known. It has been shown that loss of PYCR1 function leads to decreased mitochondrial membrane potential and increased adequate susceptibility to apoptosis under oxidative stress. These finding show that there are a spectrum host genes that restrict cell tropism and virus replication.

Vero cells that were ablated of the NAT9 gene using CRISPR-Cas9 KO had nearly a 1000-fold phenotypic increase in ZIKV strain PVRABC59 replication (pfu/mL) compared to wildtype Vero cells (FIG. 9B). This data shows that siRNA screening is adequate to find key host genes that increase virus replication, and KO of these genes is an important feature for the creation of an enhanced stable cell line that can serve as a universal vaccine cell line.

b) Discussion.

To make a universal cell line that is receptive to a range of viruses, one must identify key host cell genes that influence intrinsic immunity and help determine restriction or permissiveness toward virus infection and replication. There is convincing evidence that many viruses have evolved not only to avoid the apoptosis-mediated viral elimination, but also to exploit and even activate it to facilitate their lifecycle. As one example, influenza proteins NS1 and PB1-F2 act as apoptosis promoters, and it was found that caspase-3 activation was needed for efficient influenza virus replication. Each virus has found its way to survive, and co-opt the host cell for replication.

Vero cells are one of the first continuous cell lines that were used for vaccine production which was helped by their lack of antiviral IFN signaling. This feature makes the Vero cell line more permissive for a wide spectrum of viruses. In this study, the top 18 genes that were discovered from screening and validating a siRNA genome-wide screen of IAV, RV, and PV (Table 2) were KD with the goal of finding the top host genes in Vero cells and HEp-2 cells that can be used to create a universal vaccine cell line. Vero cells transfected with siRNAs to KD BTN2A1, CNTD2, EP300, NEU2, and ZNF205 support enhanced virus replication of most viruses examined here including PV, RV, IAV, DENY, HAV, EV71, MV, RUBY, YFV, VZV, and ZIKV (Table 4).

TABLE 4 siRNA gene KD modulates replication of several viruses.

| | Vero cells | HEp-2 cells |
|---|---|---|
| BTN2A1 | PV, DENV, MuV, | MuV, YFV |
| CNTD2 | PV, HAV | EV71, HAV |
| COQ9 | YFV, HAV | DENV, IBV* |
| EMX2 | RV | EV71, HAV |
| EP300 | RC, EV71, YFV, VSV | EV71, HAV, IBV* |
| GCGR | PV, YFV, HAV, | |
| PLA2GB1 | YFV | EV71 |
| PYCR1 | IAV, HAV, ZIKV* | HAV, VZV |
| NAT9 | RV, ZIKV* | UBV* |
| NDUFA9 | RV | HAV, IBV* |
| NEU2 | HAV | |
| RAD51AP1 | YFV, ZIKV* | |
| SEC61G | | HAV |
| STRADA | DENV | |
| SVOPL | DENV, MuV | |
| ZNF205 | RUBV, ZIKV* | HAV |
| ZFYVE9 | DENV, ZIKV* | |

BTN2A1-butyrophilin subfamily 2 member A1;
CNTD2-cyclin N-terminal domain containing 2;
COQ9-ubiquinone biosynthesis protein,
EMX2-homeobox-containing transcription factor,
EP300-E1A binding protein;
GCGRÐG-protein coupled receptor for glucagon,
PLA2GB1-epithelial-cell-derived group 1B phospholipase A2,
PYCR1-pyrroline-5-carboxylate reductase 1;
NAT9-N-Acetyltransferase 9,
NDUFA9-NADH-coenzyme Q Reductase,
NEU2-neuraminidase 2,
RAD51AP1ÐRAD51 associated protein,
SEC61G-SEC61 translocon gamma subunit;
STRADA-STE20-related kinase adapter protein alpha,
SOPL-a paralog of the SVOP gene that encodes synaptic vesicle 2-related protein;
ZNF205-zinc finger protein 205;
ZFYVE9-zinc finger FYVE domain-containing protein 9,
IAV—Influenza A virus;
PV—poliovirus;
RV—rotavirus 3;
IBV—influenza B virus;
DENV—dengue virus type 1;
YFV—Yellow fever virus 17D strain;
HAV—hepatitis A virus;
EV71-Coxsackie virus B5 (also known as enterovirus 71 (EV71));
MuV—mumps virus,
RUBV—rubella virus;
VZV—varicella zoster virus.
Based on significantly different error bars representing ± SEM from three independent experiments $p < 0.001$.
*= results from one independent plaque assay where n = 3 wells/gene KD were evaluated and the foldchange over the NTC.

Stand out findings from the results: 1) it is possible to create an enhanced universal cell line permissive for most viruses tested, 2) the Vero cell lines are generally better at propagating viruses than HEp-2 cells, 3) there is increased virus replication is in the KD cell lines (~80-fold for YFV to ~170-fold for HAV to ~1 log increase for ZIKV), 4) virus strains difference do affect the outcome and the magnitude of virus replication. This can be seen between ZIKV strains PVRABC59 and lbH30656 which had nearly $5\times10^7$ PFU/mL and $2\times10^6$ PFU/mL between strains, respectively, using the same propagation conditions. The reasons for these differences are not presently known.

In this study, viruses were evaluated with known strain variation, and expected these differences to affect the host genes linked to virus replication as was discovered for PV studies. Another example of antigenically distinct viruses are DENY which has been classified into four individual serotypes (DENY 1-4). DENY like many other viruses has evolved multiple mechanisms to evade the innate immune response and increase virus replication. It is clear that universal vaccination can have major impacts on diseases such as poliovirus, smallpox and measles, mumps, and rubella. One the other hand, vaccine-preventable diseases such as influenza continue to cause significant disease because of use of the inadequate use of vaccines. Advances in vaccine technology are now providing the opportunity to target new diseases and create enhanced vaccine cell lines. Making a cell line that allows for reduced costs is a rate-limiting feature that drives prioritization and going forward. For example, RV is a common cause of severe gastroenteritis in children. RVs causes a large disease burden ($US 2 billion in 2007), where morbidity and mortality occurs in malnourished infants in low and middle income countries. Vaccines typically confer 85-100% protection against severe disease, while in low income regions protection is around 46-77%, thus the RV vaccination program must rely upon sustained vaccine efficacy level against evolving strains. Cost effectiveness depends largely on the RV mortality rate and the price of the vaccine in relation to the per capita gross domestic product. An enhanced vaccine cell line like Vero cells could save millions of dollars and improve quality life worldwide.

c) Materials and Methods (1) Cells and Viruses.

A siRNA screen was performed using Vero cells (African green monkey kidney) and HEp-2 cells (human laryngeal carcinoma, HeLa-derivative). Vero cells were cultured at 37° C. and 5% CO2 in Dulbecco's modified Eagle's medium (DMEM; HyClone, GE Healthcare) supplemented with 10% fetal bovine serum (FBS; HyClone). The same passage number of Vero cells and HEp-2 cells was used in validation studies to minimize differences and aid interpretation. A master cell bank was created to ensure that all experiments were performed using a consistent low number of cell passages. PV Sabin-2 was obtained from (National Institute for Biological Standards and Control, Health Protection Agency, Potters Bar, United Kingdom). RV strain RV3 was obtained from the CDC and propagated in MA104 cells. IAV (A/WSN 33) and influenza B/Malaysia/2506/2004 were propagated in embryonated chicken eggs. DENY-1 (Hawaii, BEI resources NR-82) was grown in Vero cells. The YFV 17 D vaccine strain (BEI resources NR-116) was grown in Vero cells. HAV (ATCC-VR-2266) was grown in MRC-145 cells. Coxsackie Virus B5 (EV71; ATCC VR-185) was grown in Vero cells. MUV virus (ATCC VR-1438) was grown in HEp-2 cells. RUBY (ATCC VR-1359) was grown in Vero cells. VZV (human herpesvirus 3 ATCC VR-1367) was grown in MRC-145 cells. ZIKV (strains PVRABC59 and lbH30656 were tested) in Vero cells.

(2) Human siRNAs.

ON-TARGETplus siRNAs (GE Healthcare, Lafayette, Colo.) was used to target the genes of interest (Table 2). Non-targeting controls allowed assessment of non-specific effects. Pooled siRNA controls were used for reduction of off-targeting with Vero cells, and for use with SMARTpool siRNA reagents that were used for validation.

(3) siRNA Assay.

siRNAs targeting the 18 host genes of interest (Table 2) were reverse transfected individually in triplicate into HEp-2 cells or Vero cells at a final concentration of 50 nM using 0.3% DharmaFECT-4. Briefly, On-TARGETplus siRNAs were mixed with DharmaFECT 4 reagent in serum-free medium (Opti-MEM; Invitrogen Inc., Carlsbad, Calif.) and incubated at room temperature for 20 min A NTC siRNA (GE Healthcare) and a PV, RV or IAV type-specific positive siRNA control target were included. Vero cells were subsequently added (9,000 cells/well) with DMEM supplemented with 10% FBS. Transfected cells were cultured at 37° C. and 5% CO2. After 48h, the medium was removed and cells were infected with Sabin-2 (moi=0.1) in DMEM supplemented with 2% FCS and 1% penicillin-streptomycin. In some cases, 24h pi; the plates were frozen at 80° C. and stored until analysis of antigen content by ELISA. For siRNAs targeting the other viruses (Table 2), similar methods were used. The validated gene hits from IAV, PV and RV were analyzed for the top 6 PV, top 6 IAV virus, and the 6 top RV hits, and several end-point assays such as plaque assay were re-confirmed. For PV, RV and IAV, all assays used an endpoint of day 3 pi with a moi=0.1. ZIKV was at day 5 pi at moi=0.1. For all other others examined an endpoint of day 7-10 pi was used. In all siRNA studies, there was >90% gene KD (Table 3) which is consistent with the manufacturer assertions (Dharmacon GE).

(4) RT-qPCR.

qPCR was performed to evaluate that KD took place with each of the siRNAs. KD of the genes (Table 2) was examined in HEp-2 cells using the comparative CT method (ΔΔCT) for relative quantitation for measuring siRNA-induced KD of a particular gene using TaqMan, and >90% gene KD was confirmed (Table 3). The RNA from the siRNA-transfected cells was assessed by measuring the RNA levels of the GAPDH gene, according to an endogenous 18S RNA. A NTC siRNA-transfected was also assessed to the experimental samples to assess the negative control samples. The ΔΔCT was used to calculate the percent remaining gene expression and the percent knockdown.

(5) Gene KO (NAT9).

The Vero cell line and a CRISPR-Cas9 deleted Vero cell line lacking NAT9 (ΔNAT9) were plated in 24-well cell culture plates and infected (moi=0.5) with either strains of PVRABC59 and lbH30656 of ZIKV. The virus-infected plates were harvested day 5 pi for plaque assay performed as described. All experiments were performed in triplicate.

(6) Statistics.

Statistical analyses were performed using GraphPad Prism software using one-way ANOVA (reporter studies) or Student's t test.

V. REFERENCES

Abraham, R., et al., High throughput proteomic analysis and a comparative review identify the nuclear chaperone, Nucleophosmin among the common set of proteins modulated in Chikungunya virus infection. J Proteomics, 2015. 120: p. 126-41.

Agbulos D S, Barelli L, Giordano B V, Hunter F F (2016) Zika Virus: Quantification, Propagation, Detection, and Storage. Curr Protoc Microbiol 43: 15D 14 11-15D 14 16.

Agrawal S, Kandimalla E R (2004) Role of Toll-like receptors in antisense and siRNA [corrected]. Nat Biotechnol 22: 1533-1537.

An, S., et al., Induction of apoptosis in murine coronavirus-infected cultured cells and demonstration of E protein as an apoptosis inducer. J Virol, 1999. 73(9): p. 7853-9.

Andrei, G., et al., Evaluating phenotype and genotype of drug-resistant strains in herpesviruses. Mol Biotechnol, 2001. 18(2): p. 155-67.

Andzhaparidze O G, Bogomolova N N, Boriskin Yu S, Drynov I D (1983) Chronic non-cytopathic infection of human continuous cell lines with mumps virus. Acta Virol 27: 318-328.

Arvin, A. M., Varicella-zoster virus. Clin Microbiol Rev, 1996. 9(3): p. 361-81. Audsley J M, Tannock G A (2005) The growth of attenuated influenza vaccine donor strains in continuous cell lines. J Virol Methods 123: 187-193.

Bagga, S. and M. J. Bouchard, Cell cycle regulation during viral infection. Methods Mol Biol, 2014. 1170: p. 165-227.

Bakre A, Andersen L E, Meliopoulos V, Coleman K, Yan X, et al. (2013) Identification of Host Kinase Genes Required for Influenza Virus Replication and the Regulatory Role of MicroRNAs. PLoS One 8: e66796.

Barrett, P. N., D. Portsmouth, and H. J. Ehrlich, Vero cell culture-derived pandemic influenza vaccines: preclinical and clinical development. Expert Rev Vaccines, 2013. 12(4): p. 395-413.

Barrett, P. N., et al., Vero cell platform in vaccine production: moving towards cell culture-based viral vaccines. Expert Rev Vaccines, 2009. 8(5): p. 607-18.

Calvet, G. A., F. B. Santos, and P. C. Sequeira, Zika virus infection: epidemiology, clinical manifestations and diagnosis. Curr Opin Infect Dis, 2016. 29(5): p. 459-66.

Cassone A, Rappuoli R (2010) Universal vaccines: shifting to one for many. MBio 1.

Cavaletto M, Giuffrida M G, Fortunato D, Gardano L, Dellavalle G, et al. (2002) A proteomic approach to evaluate the butyrophilin gene family expression in human milk fat globule membrane. Proteomics 2: 850-856.

Chavas L M, Tringali C, Fusi P, Venerando B, Tettamanti G, et al. (2005) Crystal structure of the human cytosolic sialidase Neu2. Evidence for the dynamic nature of substrate recognition. J Biol Chem 280: 469-475.

Choumet, V. and P. Despres, Dengue and other flavivirus infections. Rev Sci Tech, 2015. 34(2): p. 473-8, 467-72.

Clarke, B. D., et al., Functional non-coding RNAs derived from the flavivirus 3' untranslated region. Virus Res, 2015. 206: p. 53-61.

Clementi, N., et al., A human monoclonal antibody with neutralizing activity against highly divergent influenza subtypes. PLoS One, 2011. 6(12): p. e28001.

Cunningham, A. L., The herpes zoster subunit vaccine. Expert Opin Biol Ther, 2016. 16(2): p. 265-71.

De Filette, M., et al., Antiserum against the conserved nine amino acid N-terminal peptide of influenza A virus matrix protein 2 is not immunoprotective. J Gen Virol, 2011. 92(Pt 2): p. 301-6.

Desmyter J, Melnick J L, Rawls W E (1968) Defectiveness of interferon production and of rubella virus interference in a line of African green monkey kidney cells (Vero). J Virol 2: 955-961.

Dormitzer P R, Galli G, Castellino F, Golding H, Khurana S, et al. (2011) Influenza vaccine immunology. Immunol Rev 239: 167-177.

Dyson, H. J. and P. E. Wright, Role of Intrinsic Protein Disorder in the Function and Interactions of the Transcriptional Coactivators CREB-binding Protein (CBP) and p300. J Biol Chem, 2016. 291(13): p. 6714-22.

Engelich, G., M. White, and K. L. Hartshorn, Neutrophil survival is markedly reduced by incubation with influenza virus and *Streptococcus pneumoniae*: role of respiratory burst. J Leukoc Biol, 2001. 69(1): p. 50-6.

Feinstone S M, Daemer R J, Gust I D, Purcell R H (1983) Live attenuated vaccine for hepatitis A. Dev Biol Stand 54: 429-432.

Feldman, S. A., et al., Use of the piggyBac transposon to create stable packaging cell lines for the production of clinical-grade self-inactivating gamma-retroviral vectors. Hum Gene Ther Methods, 2014. 25(4): p. 253-60.

Fiorucci, G., et al., MicroRNAs in virus-induced tumorigenesis and IFN system. Cytokine Growth Factor Rev, 2015. 26(2): p. 183-94.

Fletcher, M. A., L. Hessel, and S. A. Plotkin, Human diploid cell strains (HDCS) viral vaccines. Dev Biol Stand, 1998. 93: p. 97-107.

Genzel, Y., Designing cell lines for viral vaccine production: Where do we stand? Biotechnol J, 2015. 10(5): p. 728-40.

Goebel S, Snyder B, Sellati T, Saeed M, Ptak R, et al. (2016) A sensitive virus yield assay for evaluation of Antivirals against Zika Virus. J Virol Methods 238: 13-20.

Gordy J T, Jones C A, Rue J, Crawford P C, Levy J K, et al. (2012) Surveillance of feral cats for influenza A virus in north central Florida. Influenza Other Respir Viruses 6: 341-347.

Grahn A, Studahl M (2015) Varicella-zoster virus infections of the central nervous system—Prognosis, diagnostics and treatment. J Infect 71: 281-293.

Grimwood K, Lambert S B, Milne R J (2010) Rotavirus infections and vaccines: burden of illness and potential impact of vaccination. Paediatr Drugs 12: 235-256.

Hallauer, P. L. and K. E. Hastings, Human cytomegalovirus IE1 promoter/enhancer drives variable gene expression in all fiber types in transgenic mouse skeletal muscle. BMC Genet, 2000. 1: p. 1.

Holmes K, Williams C M, Chapman E A, Cross M J (2010) Detection of siRNA induced mRNA silencing by R T-qPCR: considerations for experimental design. BMC Res Notes 3: 53.

Huang Y J, Higgs S, Home K M, Vanlandingham D L (2014) Flavivirus-mosquito interactions. Viruses 6: 4703-4730.

Hughes J H (1993) Physical and chemical methods for enhancing rapid detection of viruses and other agents. Clin Microbiol Rev 6: 150-175.

Jacobsson J A, Haitina T, Lindblom J, Fredriksson R (2007) Identification of six putative human transporters with structural similarity to the drug transporter SLC22 family. Genomics 90: 595-609.

Jang, Y. H., et al., Host defense mechanism-based rational design of live vaccine. PLoS One, 2013. 8(10): p. e75043.

Jazi, M. H., et al., In vivo electroporation enhances immunogenicity and protection against influenza A virus challenge of an M2e-HSP70c DNA vaccine. Virus Res, 2012. 167(2): p. 219-25.

Jeang, K. T., RNAi in the regulation of mammalian viral infections. BMC Biol, 2012. 10: p. 58.

Kaiser, W. J., J. W. Upton, and E. S. Mocarski, Viral modulation of programmed necrosis. Curr Opin Virol, 2013. 3(3): p. 296-306.

Keating G M (2016) Shingles (Herpes Zoster) Vaccine (Zostavax®): A Review in the Prevention of Herpes Zoster and Postherpetic Neuralgia. BioDrugs 30: 243-254.

Keating, R., et al., The kinase mTOR modulates the antibody response to provide cross-protective immunity to lethal infection with influenza virus. Nat Immunol, 2013. 14(12): p. 1266-76.

Kennedy, P. G., Issues in the Treatment of Neurological Conditions Caused by Reactivation of Varicella Zoster Virus (VZV). Neurotherapeutics, 2016. 13(3): p. 509-13.

Kirkwood C D, Bishop R F, Coulson B S (1998) Attachment and growth of human rotaviruses RV-3 and S12/85 in Caco-2 cells depend on VP4. J Virol 72: 9348-9352.

Kramer, M. J., et al., Cell and virus sensitivity studies with recombinant human alpha interferons. J Interferon Res, 1983. 3(4): p. 425-35.

Kularatne, S. A., Dengue fever. BMJ, 2015. 351: p. h4661.

Kuo M L, Lee M B, Tang M, den Besten W, Hu S, et al. (2016) PYCR1 and PYCR2 Interact and Collaborate with RRM2B to Protect Cells from Overt Oxidative Stress. Sci Rep 6: 18846.

Lambert N, Strebel P, Orenstein W, Icenogle J, Poland G A (2015) Rubella. Lancet 385: 2297-2307.

Lavender, H., et al., In vitro characterization of the activity of PF-05095808, a novel biological agent for hepatitis C virus therapy. Antimicrob Agents Chemother, 2012. 56(3): p. 1364-75.

Lee J H, Lee G C, Kim J I, Yi H A, Lee C H (2013) Development of a new cell culture-based method and optimized protocol for the detection of enteric viruses. J Virol Methods 191: 16-23.

Lessler J, Chaisson L H, Kucirka L M, Bi Q, Grantz K, et al. (2016) Assessing the global threat from Zika virus. Science 353: aaf8160.

Li M L, Weng K F, Shih S R, Brewer G (2016) The evolving world of small RNAs from RNA viruses. Wiley Interdiscip Rev RNA 7: 575-588.

Liebhaber H, Riordan J T, Horstmann D M (1967) Replication of rubella virus in a continuous line of African green monkey kidney cells (Vero). Proc Soc Exp Biol Med 125: 636-643.

Liu, X., et al., [Establishment of a stable and inducible mammalian cell line expressing influenza virus A M2 protein]. Sheng Wu Gong Cheng Xue Bao, 2011. 27(5): p. 747-54.

Lohman D C, Forouhar F, Beebe E T, Stefely M S, Minogue C E, et al. (2014) Mitochondrial COQ9 is a lipid-binding protein that associates with COQ7 to enable coenzyme Q biosynthesis. Proc Natl Acad Sci USA 111: E4697-4705.

Lyons, S. F., et al., An indirect radioimmunoassay for interferon. J Virol Methods, 1982. 5(2): p. 93-100.

Mackinnon A L, Paavilainen V O, Sharma A, Hegde R S, Taunton J (2014) An allosteric Sec61 inhibitor traps nascent transmembrane helices at the lateral gate. Elife 3: e01483.

Man, S. M., R. Karki, and T D Kanneganti, AIM2 inflammasome in infection, cancer, and autoimmunity: Role in DNA sensing, inflammation, and innate immunity. Eur J Immunol, 2016. 46(2): p. 269-80.

Martin A, Lemon S M (2006) Hepatitis A virus: from discovery to vaccines. Hepatology 43: S164-172.

Meliopoulos V A, Andersen L E, Birrer K F, Simpson K J, Lowenthal J W, et al. (2012) Host gene targets for novel influenza therapies elucidated by high-throughput RNA interference screens. FASEB J 26: 1372-1386.

Meliopoulos V A, Andersen L E, Brooks P, Yan X, Bakre A, et al. (2012) MicroRNA regulation of human protease genes essential for influenza virus replication. PLoS One 7: e37169.

Milstien J, Grachev V, Padilla A, Griffiths E (1996) WHO activities towards the three Rs in the development and control of biological products. Dev Biol Stand 86: 31-39.

Modlin J, Wenger J (2014) Achieving and maintaining polio eradication—new strategies. N Engl J Med 371: 1476-1479.

Montagnon, B. J. and J. C. Vincent-Falquet, Experience with the Vero cell line. Dev Biol Stand, 1998. 93: p. 119-23.

Moore A E, Sabachewsky L, Toolan H W (1955) Culture characteristics of four permanent lines of human cancer cells. Cancer Res 15: 598-602.

Music S (2010) Governments, off-patent vaccines, smallpox and universal childhood vaccination. Vaccine 28: 869-872.

Nagarajan M M, Kibenge F S (1998) A novel technique for in-vivo assay of viral regulatory regions in genomes of animal RNA viruses. J Virol Methods 72: 51-58.

Nagy, P. D. and J. Pogany, The dependence of viral RNA replication on co-opted host factors. Nat Rev Microbiol, 2011. 10(2): p. 137-49.

Nakai, Y., et al., Apoptosis and microglial activation in influenza encephalopathy. Acta Neuropathol, 2003. 105 (3): p. 233-9.

Ojha C R, Rodriguez M, Dever S M, Mukhopadhyay R, El-Hage N (2016) Mammalian microRNA: an important modulator of host-pathogen interactions in human viral infections. J Biomed Sci 23: 74.

Park, M. S., et al., Newcastle disease virus V protein is a determinant of host range restriction. J Virol, 2003. 77(17): p. 9522-32.

Pizzuto, M. S., et al., An engineered avian-origin influenza A virus for pancreatic ductal adenocarcinoma virotherapy. J Gen Virol, 2016. 97(9): p. 2166-79.

Poltronieri P, Sun B, Mallardo M (2015) RNA Viruses: RNA Roles in Pathogenesis, Coreplication and Viral Load. Curr Genomics 16: 327-335.

Rao C D, Reddy H, Naidu J R, Raghavendra A, Radhika N S, et al. (2015) An enzyme-linked immuno focus assay for rapid detection and enumeration, and a newborn mouse model for human non-polio enteroviruses associated with acute diarrhea. J Virol Methods 224: 47-52.

Reemers, S. S., et al., Cellular host transcriptional responses to influenza A virus in chicken tracheal organ cultures differ from responses in in vivo infected trachea. Vet Immunol Immunopathol, 2009. 132(2-4): p. 91-100.

Saito, T. and M. Gale, Jr., Principles of intracellular viral recognition. Curr Opin Immunol, 2007. 19(1): p. 17-23.

Santak M, Markusic M, Balija M L, Kopac S K, Jug R, et al. (2015) Accumulation of defective interfering viral particles in only a few passages in Vero cells attenuates mumps virus neurovirulence. Microbes Infect 17: 228-236.

Scott L J (2016) Tetravalent Dengue Vaccine: A Review in the Prevention of Dengue Disease. Drugs 76: 1301-1312.

Shaw, M. L., et al., Nipah virus V and W proteins have a common STAT1-binding domain yet inhibit STAT1 activation from the cytoplasmic and nuclear compartments, respectively. J Virol, 2004. 78(11): p. 5633-41.

Sim, S. and M. L. Hibberd, Genomic approaches for understanding dengue: insights from the virus, vector, and host. Genome Biol, 2016. 17: p. 38.

Sloop, K. W., M. D. Michael, and J. S. Moyers, Glucagon as a target for the treatment of Type 2 diabetes. Expert Opin Ther Targets, 2005. 9(3): p. 593-600.

Smith D R (2016) Waiting in the wings: The potential of mosquito transmitted flaviviruses to emerge. Crit Rev Microbiol: 1-18.

Stroud D A, Formosa L E, Wijeyeratne X W, Nguyen T N, Ryan M T (2013) Gene knockout using transcription activator-like effector nucleases (TALENs) reveals that human NDUFA9 protein is essential for stabilizing the junction between membrane and matrix arms of complex I. J Biol Chem 288: 1685-1690.

Suzuki R, de Borba L, Duarte dos Santos C N, Mason P W (2007) Construction of an infectious cDNA clone for a Brazilian prototype strain of dengue virus type 1: characterization of a temperature-sensitive mutation in NS1. Virology 362: 374-383.

Takizawa, T., et al., Recruitment of apoptotic cysteine proteases (caspases) in influenza virus-induced cell death. Microbiol Immunol, 1999. 43(3): p. 245-52.

Trigg, B. J. and B. J. Ferguson, Functions of DNA damage machinery in the innate immune response to DNA virus infection. Curr Opin Virol, 2015. 15: p. 56-62.

Tripp R A, Mark Tompkins S (2015) Antiviral effects of inhibiting host gene expression. Curr Top Microbiol Immunol 386: 459-477.

Tripp R A, Tompkins S M (2009) Therapeutic applications of RNAi for silencing virus replication. Methods Mol Biol 555: 43-61.

van der Sanden S M, Wu W, Dybdahl-Sissoko N, Weldon W C, Brooks P, et al. (2015) Engineering Enhanced Vaccine Cell Lines To Eradicate Vaccine-Preventable Diseases: the Polio End Game. J Virol 90: 1694-1704.

Vincent-Falquet J C, Peyron L, Souvras M, Moulin J C, Tektoff J, et al. (1989) Qualification of working cell banks for the Vero cell line to produce licensed human vaccines. Dev Biol Stand 70: 153-156.

Virk R K, Gunalan V, Tambyah P A (2016) Influenza infection in human host: challenges in making a better influenza vaccine. Expert Rev Anti Infect Ther 14: 365-375.

Wang L, Zhu L, Zhu H (2016) Efficacy of varicella (VZV) vaccination: an update for the clinician. Ther Adv Vaccines 4: 20-31.

Wearing H J, Robert M A, Christofferson R C (2016) Dengue and chikungunya: modelling the expansion of mosquito-borne viruses into naive populations. Parasitology: 1-14.

Weir J P, Gruber M F (2016) An overview of the regulation of influenza vaccines in the United States. Influenza Other Respir Viruses 10: 354-360.

Westenfeld F W, Winn W C, Jr. (1994) Use of rhesus monkey kidney cells for isolation of varicella-zoster virus. Am J Clin Pathol 102: 733-735.

Worschech, A., et al., Systemic treatment of xenografts with vaccinia virus GLV-1h68 reveals the immunologic facet of oncolytic therapy. BMC Genomics, 2009. 10: p. 301.

Wu W, Orr-Burks N, Karpilow J, Tripp R A (2017) Development of improved vaccine cell lines against rotavirus. Sci Data 4: 170021.

Zamarin, D., et al., Influenza virus PB1-F2 protein induces cell death through mitochondrial ANTS and VDAC1. PLoS Pathog, 2005. 1(1): p. e4.

Zhou H, Huang Y, Yuan S, Li Y, Wu S, et al. (2017) Sequential immunization with consensus influenza hemagglutinins raises cross-reactive neutralizing antibodies against various heterologous H A strains. Vaccine 35: 305-312.

Zhou Y, Li J X, Jin P F, Wang Y X, Zhu F C (2016) Enterovirus 71: a whole virion inactivated enterovirus 71 vaccine. Expert Rev Vaccines 15: 803-813.

What is claimed is:

1. An isolated cell or cell line comprising decreased expression of PLA2G1B and one or more of BTN2A1, CNTD2, COQ9, EMX2, EP300, FGF2, GCGR, NAT9, NDUFA9, NEU2, PYCR1, RAD51AP1, SEC61G, STRADA, SVOPL, ZFYVE9, and ZNF205.

2. The isolated cell or cell line of claim 1, comprising decreased expression of PLA2G1B and EMX2 and further comprising decreased expression of one or more of BTN2A1, CNTD2, COQ9, EP300, FGF2, GCGR, NAT9, NDUFA9, NEU2, PYCR1, RAD51AP1, SEC61G, STRADA, SVOPL, ZFYVE9, and ZNF205.

3. An isolated cell or cell line comprising decreased expression of PLA2G1 B and one or more of BTN2A1, CNTD2, ZNF205, GCGR, and EP300; and decreased expression of one or more of COQ9, NAT9, NDUFA9, NEU2, RAD51AP1, and SVOPL.

4. The isolated cell or cell line of claim 1, wherein the cell is a Madin-Darby Canine Kidney cell, Vero Cell, EB66 cell, HEp-2C cell, or Per C6 cell.

5. The isolated cell or cell line of claim 4, wherein the cell is a Vero cell and the cell further comprises decreased expression of one or more genes selected from the group consisting of BTN2A1, CNTD2, EP300, GCGR, and ZNF205.

* * * * *

UNITED STATES PATENT AND TRADEMARK OFFICE
CERTIFICATE OF CORRECTION

PATENT NO. : 11,655,471 B2
APPLICATION NO. : 16/490919
DATED : May 23, 2023
INVENTOR(S) : Ralph A Tripp It is certified that error appears in the above-identified patent and that said Letters Patent is hereby corrected as shown below:

In the Claims

In Column 86, Line 36 of Claim 3, the text, "...PLA2G1 B..." should read, --PLA2G1B--

Signed and Sealed this
Third Day of October, 2023

Katherine Kelly Vidal
*Director of the United States Patent and Trademark Office*